United States Patent
Joseph et al.

(10) Patent No.: US 12,188,099 B2
(45) Date of Patent: Jan. 7, 2025

(54) INTEGRATED PROVIRAL SEQUENCING ASSAY

(71) Applicant: UNIVERSITY OF PITTSBURGH-OF THE COMMONWEALTH SYSTEM OF HIGHER EDUCATION, Pittsburgh, PA (US)

(72) Inventors: Kevin Joseph, Pittsburgh, PA (US); John W. Mellors, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 846 days.

(21) Appl. No.: 17/413,130

(22) PCT Filed: Dec. 12, 2019

(86) PCT No.: PCT/US2019/065945
§ 371 (c)(1),
(2) Date: Jun. 11, 2021

(87) PCT Pub. No.: WO2020/123787
PCT Pub. Date: Jun. 18, 2020

(65) Prior Publication Data
US 2022/0042120 A1 Feb. 10, 2022

Related U.S. Application Data

(60) Provisional application No. 62/778,480, filed on Dec. 12, 2018.

(51) Int. Cl.
*C12Q 1/70* (2006.01)
*C12Q 1/686* (2018.01)

(52) U.S. Cl.
CPC ............. *C12Q 1/703* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 5,427,930 A | 6/1995 | Birkenmeyer et al. | |
| 5,744,311 A | 4/1998 | Frasier et al. | |
| 6,025,134 A | 2/2000 | Sooknanan | |
| 6,033,881 A | 3/2000 | Himmler et al. | |
| 2017/0039316 A1* | 2/2017 | Fofanov | G16B 30/10 |

FOREIGN PATENT DOCUMENTS

| | | |
|---|---|---|
| WO | 90/01069 | 2/1990 |
| WO | 2005/019479 | 3/2005 |
| WO | 2012/006061 | 1/2012 |
| WO | 2016/049932 | 4/2016 |

OTHER PUBLICATIONS

International Search Report and Written Opinion dated Mar. 24, 2020, from International Application No. PCT/US2019/065945, 15 pages.

Park, J.H. et al. "Effect of siRNA with an Asymmetric RNA/dTdT Overhang on RNA Interference Activity", Nucleic Acid Therapeutics, vol. 24, No. 5, 2014, 8 pages.

Leoni C, Volpicella M, De Leo F, Gallerani R, Ceci LR. Genome walking in eukaryotes. FEBS J. Nov. 2011;278(21):3953-77. doi: 10.1111/j.1742-4658.2011.08307.x. Epub Sep. 15, 2011. Review. PubMed PMID: 21848672.

Maldarelli F, Wu X, Su L, Simonetti FR, Shao W, Hill S, Spindler J, Ferris AL, Mellors JW, Kearney MF, Coffin JM, Hughes SH. HIV latency. Specific HIV integration sites are linked to clonal expansion and persistence of infected cells. Science. Jul. 11, 2014;345(6193):179-83. doi: 10.1126/science.1254194. Epub Jun. 26, 2014. PubMed PMID: 24968937; PubMed Central PMCID: PMC4262401.

Serrao E, Cherepanov P, Engelman AN. Amplification, Next-generation Sequencing, and Genomic DNA Mapping of Retroviral Integration Sites. J Vis Exp. Mar. 22, 2016;(109). doi: 10.3791/53840. PubMed PMID: 27023428; PubMed Central PMCID: PMC4829050.

* cited by examiner

*Primary Examiner* — Agnieszka Boesen
(74) *Attorney, Agent, or Firm* — Meunier Carlin & Curfman LLC

(57) ABSTRACT

Disclosed are synthetic 71 base pair, partially-double stranded DNA oligonucleotides and methods for their use in the amplification and identification or integrated proviral DNA.

15 Claims, 19 Drawing Sheets

Specification includes a Sequence Listing.

SEQ ID NO: 1 > Sense_v1.0_TA
5'OH-GATACCTTAGCGATGGACACAGTACGATACCTACTCCCTGGCGACCTGATATGATTAGCGTTGTGCCGAGCG*G*T-3'OH
CGCAACACGCTCGC C-5'P    SEQ ID NO: 2 > Antisense_v1.0_TA C3 spacers Output of sir_graph (C)
mfold_util 4.5

Created Mon Nov 12 12:49:48 2018

| Donor ID | Number of VLPAS(+) MDA wells | Number of Integration Site (+) MDA wells | Number of matching VLPAS/IS amplicons[A] | Percentage of VLPAS(+) MDA wells yielding matching IS amplicons[B] | Percentage of VLPAS(+) MDA wells yielding IS amplicons[C] | Flanking host sequence length (mean, range)[D] |
|---|---|---|---|---|---|---|
| C-02 | 19 | 17 | 14 | 73.7% | 89.5% | 430, 19-1090 |
| C-03 | 22 | 16 | 14 | 63.6% | 72.7% | 270, 18-664 |
| F-07 | 92 | 68 | 30 | 32.6% | 73.9% | 406, 18-1363 |
| K-01 | 28 | 20 | 15 | 53.6% | 71.4% | 510, 22-1137 |
| R-09 | 33 | 15 | 11 | 33.3% | 45.5% | 328, 32-923 |
| Average: | | | | 51.4% | 70.6% | 389, 22-1035 |

FIG. 11B

SEQUENCE LISTING

<160> NUMBER OF SEQ ID NOS: 115

<210> SEQ ID NO 1
<211> LENGTH: 71
<212> TYPE: DNA
<213> ORGANISM: Artificial Sequence
<220> FEATURE:
<223> OTHER INFORMATION: Synthetic construct

<400> SEQUENCE: 1
gataccttag cgatggacag tacgatacct actccctggc gacctgatat gattagcgtt    60
gtgcgagcgg t    71

<210> SEQ ID NO 2
<211> LENGTH: 14
<212> TYPE: DNA
<213> ORGANISM: Artificial Sequence
<220> FEATURE:
<223> OTHER INFORMATION: Synthetic construct

<400> SEQUENCE: 2
ccgctcgcac aacg    14

<210> SEQ ID NO 3
<211> LENGTH: 30
<212> TYPE: DNA
<213> ORGANISM: Artificial Sequence
<220> FEATURE:
<223> OTHER INFORMATION: Synthetic construct

<400> SEQUENCE: 3
gataccttag cgatggacag tacgatacct    30

<210> SEQ ID NO 4
<211> LENGTH: 30
<212> TYPE: DNA
<213> ORGANISM: Artificial Sequence
<220> FEATURE:
<223> OTHER INFORMATION: Synthetic construct

<400> SEQUENCE: 4
tagcgatgga cagtacgata cctactccct    30

<210> SEQ ID NO 5
<211> LENGTH: 31
<212> TYPE: DNA
<213> ORGANISM: Artificial Sequence
<220> FEATURE:
<223> OTHER INFORMATION: Synthetic construct

<400> SEQUENCE: 5 gataccctact ccctggcgac ctgatatgat t    31

<210> SEQ ID NO 6
<211> LENGTH: 21
<212> TYPE: DNA

<213> ORGANISM: Artificial Sequence
<220> FEATURE:
<223> OTHER INFORMATION: Synthetic construct

<400> SEQUENCE: 6
cgacctgata tgattagcgt t					21

<210> SEQ ID NO 7
<211> LENGTH: 28
<212> TYPE: DNA
<213> ORGANISM: Artificial Sequence
<220> FEATURE:
<223> OTHER INFORMATION: Synthetic construct

<400> SEQUENCE: 7
aycgttctar ytccctgctt gcccatac					28

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
cytcagcaag ccgagtcctg cgtc					24

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9
agtcagtgtg gaaaatctct ag					22

<210> SEQ ID NO 10
<211> LENGTH: 22
<212> TYPE: DNA
<213> ORGANISM: Artificial Sequence
<220> FEATURE:
<223> OTHER INFORMATION: Synthetic construct

<400> SEQUENCE: 10
gagggatctc tagttaccag ag					22

<210> SEQ ID NO 11
<211> LENGTH: 21
<212> TYPE: DNA
<213> ORGANISM: Artificial Sequence
<220> FEATURE:
<223> OTHER INFORMATION: Synthetic construct

<400> SEQUENCE: 11
gtggaaaatc tctagcagtg g					21

<210> SEQ ID NO 12
<211> LENGTH: 22
<212> TYPE: DNA
<213> ORGANISM: Artificial Sequence
<220> FEATURE:
<223> OTHER INFORMATION: Synthetic construct

<400> SEQUENCE: 12
ttaccagagt cacacaacag ac					22

<210> SEQ ID NO 13
<211> LENGTH: 18
<212> TYPE: DNA
<213> ORGANISM: Artificial Sequence
<220> FEATURE:
<223> OTHER INFORMATION: Synthetic construct

<400> SEQUENCE: 13
gggaacccac tgcttaag                                                   18

<210> SEQ ID NO 14
<211> LENGTH: 23
<212> TYPE: DNA
<213> ORGANISM: Artificial Sequence
<220> FEATURE:
<223> OTHER INFORMATION: Synthetic construct

<400> SEQUENCE: 14
ccactgctag agattttcca cac                                             23

<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
aatgatacgg cgaccaccga g                                               21

<210> SEQ ID NO 16
<211> LENGTH: 22
<212> TYPE: DNA
<213> ORGANISM: Artificial Sequence
<220> FEATURE:
<223> OTHER INFORMATION: Synthetic construct

<400> SEQUENCE: 16
caagcagaag acggcatacg ag                                              22

<210> SEQ ID NO 17
<211> LENGTH: 70
<212> TYPE: DNA
<213> ORGANISM: Artificial Sequence
<220> FEATURE:
<223> OTHER INFORMATION: Synthetic construct

<400> SEQUENCE: 17
aatgatacgg cgaccaccga gatctacact atagcctaca ctctttccct acacgacgct     60
cttccgatct                                                            70

<210> SEQ ID NO 18
<211> LENGTH: 65
<212> TYPE: DNA
<213> ORGANISM: Artificial Sequence
<220> FEATURE:
<223> OTHER INFORMATION: Synthetic construct

<400> SEQUENCE: 18
gatcggaaga gcacacgtct gaactccagt cacattactc gatctcgtat gccgtcttct     60
gcttg                                                                 65

<210> SEQ ID NO 19

```
<211> LENGTH: 22
<212> TYPE: DNA
<213> ORGANISM: Artificial Sequence
<220> FEATURE:
<223> OTHER INFORMATION: Synthetic construct

<400> SEQUENCE: 19
agtcagtgtg gaaaatctct ag                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic construct

<400> SEQUENCE: 20
gagggatctc tagttaccag ag                                              22

<210> SEQ ID NO 21
<211> LENGTH: 21
<212> TYPE: DNA
<213> ORGANISM: Artificial Sequence
<220> FEATURE:
<223> OTHER INFORMATION: Synthetic construct

<400> SEQUENCE: 21
gtggaaaatc tctagcagtg g                                               21

<210> SEQ ID NO 22
<211> LENGTH: 22
<212> TYPE: DNA
<213> ORGANISM: Artificial Sequence
<220> FEATURE:
<223> OTHER INFORMATION: Synthetic construct

<400> SEQUENCE: 22
ttaccagagt cacacaacag ac                                              22

<210> SEQ ID NO 23
<211> LENGTH: 30
<212> TYPE: DNA
<213> ORGANISM: Artificial Sequence
<220> FEATURE:
<223> OTHER INFORMATION: Synthetic construct

<400> SEQUENCE: 23
gataccttag cgatggacag tacgatacct                                      30

<210> SEQ ID NO 24
<211> LENGTH: 30
<212> TYPE: DNA
<213> ORGANISM: Artificial Sequence
<220> FEATURE:
<223> OTHER INFORMATION: Synthetic construct

<400> SEQUENCE: 24
tagcgatgga cagtacgata cctactccct                                      30

<210> SEQ ID NO 25
<211> LENGTH: 23
<212> TYPE: DNA
<213> ORGANISM: Artificial Sequence
<220> FEATURE:
<223> OTHER INFORMATION: Synthetic construct

<400> SEQUENCE: 25
```
ccgcttaata yygacgctct cgc                                              23

<210> SEQ ID NO 26
<211> LENGTH: 24
<212> TYPE: DNA
<213> ORGANISM: Artificial Sequence
<220> FEATURE:
<223> OTHER INFORMATION: Synthetic construct

<400> SEQUENCE: 26
cytcagcaag ccgagtcctg cgtc                                             24

<210> SEQ ID NO 27
<211> LENGTH: 18
<212> TYPE: DNA
<213> ORGANISM: Artificial Sequence
<220> FEATURE:
<223> OTHER INFORMATION: Synthetic construct

<400> SEQUENCE: 27
cgccactgct agagattt                                                    18

<210> SEQ ID NO 28
<211> LENGTH: 23
<212> TYPE: DNA
<213> ORGANISM: Artificial Sequence
<220> FEATURE:
<223> OTHER INFORMATION: Synthetic construct

<400> SEQUENCE: 28
ccgcttaata ctgacgctct cgc                                              23

<210> SEQ ID NO 29
<211> LENGTH: 23
<212> TYPE: DNA
<213> ORGANISM: Artificial Sequence
<220> FEATURE:
<223> OTHER INFORMATION: Synthetic construct

<400> SEQUENCE: 29
ccgcttaata ttgacgctct cgc                                              23

<210> SEQ ID NO 30
<211> LENGTH: 23
<212> TYPE: DNA
<213> ORGANISM: Artificial Sequence
<220> FEATURE:
<223> OTHER INFORMATION: Synthetic construct

<400> SEQUENCE: 30
ccgcttaata ctgacgctct ygc                                              23

<210> SEQ ID NO 31
<211> LENGTH: 23
<212> TYPE: DNA
<213> ORGANISM: Artificial Sequence
<220> FEATURE:
<223> OTHER INFORMATION: Synthetic construct

<400> SEQUENCE: 31
ccgcttaata ttgacgctct cgc                                              23

<210> SEQ ID NO 32
<211> LENGTH: 23
<212> TYPE: DNA

```
<213> ORGANISM: Artificial Sequence
<220> FEATURE:
<223> OTHER INFORMATION: Synthetic construct

<400> SEQUENCE: 32
ccgcttaata ccgacgctct cgc                                            23

<210> SEQ ID NO 33
<211> LENGTH: 23
<212> TYPE: DNA
<213> ORGANISM: Artificial Sequence
<220> FEATURE:
<223> OTHER INFORMATION: Synthetic construct

<400> SEQUENCE: 33
ccgcttaata ctgacgctct cgc                                            23

<210> SEQ ID NO 34
<211> LENGTH: 18
<212> TYPE: DNA
<213> ORGANISM: Artificial Sequence
<220> FEATURE:
<223> OTHER INFORMATION: Synthetic construct

<400> SEQUENCE: 34
gggaacccac tgcttaag                                                  18

<210> SEQ ID NO 35
<211> LENGTH: 18
<212> TYPE: DNA
<213> ORGANISM: Artificial Sequence
<220> FEATURE:
<223> OTHER INFORMATION: Synthetic construct

<400> SEQUENCE: 35
cgccactgct agagattt                                                  18

<210> SEQ ID NO 36
<211> LENGTH: 18
<212> TYPE: DNA
<213> ORGANISM: Artificial Sequence
<220> FEATURE:
<223> OTHER INFORMATION: Synthetic construct

<400> SEQUENCE: 36
ccctggccct ggtgtgta                                                  18

<210> SEQ ID NO 37
<211> LENGTH: 18
<212> TYPE: DNA
<213> ORGANISM: Artificial Sequence
<220> FEATURE:
<223> OTHER INFORMATION: Synthetic construct

<400> SEQUENCE: 37
tacacaccag ggccaggg                                                  18

<210> SEQ ID NO 38
<211> LENGTH: 18
<212> TYPE: DNA
<213> ORGANISM: Artificial Sequence
<220> FEATURE:
<223> OTHER INFORMATION: Synthetic construct

<400> SEQUENCE: 38
gggaacccac tgcttaag                                                  18
```

<210> SEQ ID NO 39
<211> LENGTH: 71
<212> TYPE: DNA
<213> ORGANISM: Artificial Sequence
<220> FEATURE:
<223> OTHER INFORMATION: Synthetic construct

<400> SEQUENCE: 39
gataccttag cgatggacag tacgatacct actccctggc gacctgatat gattagcgtt    60
gtgcgagcgg t    71

<210> SEQ ID NO 40
<211> LENGTH: 14
<212> TYPE: DNA
<213> ORGANISM: Artificial Sequence
<220> FEATURE:
<223> OTHER INFORMATION: Synthetic construct

<400> SEQUENCE: 40
ccgctcgcac aacg    14

<210> SEQ ID NO 41
<211> LENGTH: 21
<212> TYPE: DNA
<213> ORGANISM: Artificial Sequence
<220> FEATURE:
<223> OTHER INFORMATION: Synthetic construct

<400> SEQUENCE: 41
aatgatacgg cgaccaccga g    21

<210> SEQ ID NO 42
<211> LENGTH: 22
<212> TYPE: DNA
<213> ORGANISM: Artificial Sequence
<220> FEATURE:
<223> OTHER INFORMATION: Synthetic construct

<400> SEQUENCE: 42
caagcagaag acggcatacg ag    22

<210> SEQ ID NO 43
<211> LENGTH: 70
<212> TYPE: DNA
<213> ORGANISM: Artificial Sequence
<220> FEATURE:
<223> OTHER INFORMATION: Synthetic construct

<400> SEQUENCE: 43
aatgatacgg cgaccaccga gatctacact atagcctaca ctctttccct acacgacgct    60
cttccgatct    70

<210> SEQ ID NO 44
<211> LENGTH: 70
<212> TYPE: DNA
<213> ORGANISM: Artificial Sequence
<220> FEATURE:
<223> OTHER INFORMATION: Synthetic construct

<400> SEQUENCE: 44
aatgatacgg cgaccaccga gatctacaca tagaggcaca ctctttccct acacgacgct    60
cttccgatct    70

```
<210> SEQ ID NO 45
<211> LENGTH: 70
<212> TYPE: DNA
<213> ORGANISM: Artificial Sequence
<220> FEATURE:
<223> OTHER INFORMATION: Synthetic construct

<400> SEQUENCE: 45
aatgatacgg cgaccaccga gatctacacc ctatcctaca ctctttccct acacgacgct    60
cttccgatct                                                          70

<210> SEQ ID NO 46
<211> LENGTH: 70
<212> TYPE: DNA
<213> ORGANISM: Artificial Sequence
<220> FEATURE:
<223> OTHER INFORMATION: Synthetic construct

<400> SEQUENCE: 46
aatgatacgg cgaccaccga gatctacacg gctctgaaca ctctttccct acacgacgct    60
cttccgatct                                                          70

<210> SEQ ID NO 47
<211> LENGTH: 70
<212> TYPE: DNA
<213> ORGANISM: Artificial Sequence
<220> FEATURE:
<223> OTHER INFORMATION: Synthetic construct

<400> SEQUENCE: 47
aatgatacgg cgaccaccga gatctacaca ggcgaagaca ctctttccct acacgacgct    60
cttccgatct                                                          70

<210> SEQ ID NO 48
<211> LENGTH: 70
<212> TYPE: DNA
<213> ORGANISM: Artificial Sequence
<220> FEATURE:
<223> OTHER INFORMATION: Synthetic construct

<400> SEQUENCE: 48
aatgatacgg cgaccaccga gatctacact aatcttaaca ctctttccct acacgacgct    60
cttccgatct                                                          70

<210> SEQ ID NO 49
<211> LENGTH: 70
<212> TYPE: DNA
<213> ORGANISM: Artificial Sequence
<220> FEATURE:
<223> OTHER INFORMATION: Synthetic construct

<400> SEQUENCE: 49
aatgatacgg cgaccaccga gatctacacc aggacgtaca ctctttccct acacgacgct    60
cttccgatct                                                          70

<210> SEQ ID NO 50
<211> LENGTH: 70
<212> TYPE: DNA
<213> ORGANISM: Artificial Sequence
<220> FEATURE:
<223> OTHER INFORMATION: Synthetic construct

<400> SEQUENCE: 50
```
aatgatacgg cgaccaccga gatctacacg tactgacaca ctctttccct acacgacgct    60
cttccgatct                                                          70

<210> SEQ ID NO 51
<211> LENGTH: 65
<212> TYPE: DNA
<213> ORGANISM: Artificial Sequence
<220> FEATURE:
<223> OTHER INFORMATION: Synthetic construct

<400> SEQUENCE: 51
gatcggaaga gcacacgtct gaactccagt cacattactc gatctcgtat gccgtcttct    60
gcttg                                                               65

<210> SEQ ID NO 52
<211> LENGTH: 65
<212> TYPE: DNA
<213> ORGANISM: Artificial Sequence
<220> FEATURE:
<223> OTHER INFORMATION: Synthetic construct

<400> SEQUENCE: 52
gatcggaaga gcacacgtct gaactccagt cactccggag aatctcgtat gccgtcttct    60
gcttg                                                               65

<210> SEQ ID NO 53
<211> LENGTH: 65
<212> TYPE: DNA
<213> ORGANISM: Artificial Sequence
<220> FEATURE:
<223> OTHER INFORMATION: Synthetic construct

<400> SEQUENCE: 53
gatcggaaga gcacacgtct gaactccagt caccgctcat tatctcgtat gccgtcttct    60
gcttg                                                               65

<210> SEQ ID NO 54
<211> LENGTH: 65
<212> TYPE: DNA
<213> ORGANISM: Artificial Sequence
<220> FEATURE:
<223> OTHER INFORMATION: Synthetic construct

<400> SEQUENCE: 54
gatcggaaga gcacacgtct gaactccagt cacgagattc catctcgtat gccgtcttct    60
gcttg                                                               65

<210> SEQ ID NO 55
<211> LENGTH: 65
<212> TYPE: DNA
<213> ORGANISM: Artificial Sequence
<220> FEATURE:
<223> OTHER INFORMATION: Synthetic construct

<400> SEQUENCE: 55
gatcggaaga gcacacgtct gaactccagt cacattcaga atctcgtat gccgtcttct    60 gcttg                                                               65

<210> SEQ ID NO 56
<211> LENGTH: 65
<212> TYPE: DNA

<213> ORGANISM: Artificial Sequence
<220> FEATURE:
<223> OTHER INFORMATION: Synthetic construct

<400> SEQUENCE: 56
gatcggaaga gcacacgtct gaactccagt cacgaattcg tatctcgtat gccgtcttct    60
gcttg    65

<210> SEQ ID NO 57
<211> LENGTH: 65
<212> TYPE: DNA
<213> ORGANISM: Artificial Sequence
<220> FEATURE:
<223> OTHER INFORMATION: Synthetic construct

<400> SEQUENCE: 57
gatcggaaga gcacacgtct gaactccagt cacctgaagc tatctcgtat gccgtcttct    60
gcttg    65

<210> SEQ ID NO 58
<211> LENGTH: 65
<212> TYPE: DNA
<213> ORGANISM: Artificial Sequence
<220> FEATURE:
<223> OTHER INFORMATION: Synthetic construct

<400> SEQUENCE: 58
gatcggaaga gcacacgtct gaactccagt cactaatgcg catctcgtat gccgtcttct    60
gcttg    65

<210> SEQ ID NO 59
<211> LENGTH: 65
<212> TYPE: DNA
<213> ORGANISM: Artificial Sequence
<220> FEATURE:
<223> OTHER INFORMATION: Synthetic construct

<400> SEQUENCE: 59
gatcggaaga gcacacgtct gaactccagt caccggctat gatctcgtat gccgtcttct    60
gcttg    65

<210> SEQ ID NO 60
<211> LENGTH: 65
<212> TYPE: DNA
<213> ORGANISM: Artificial Sequence
<220> FEATURE:
<223> OTHER INFORMATION: Synthetic construct

<400> SEQUENCE: 60
gatcggaaga gcacacgtct gaactccagt cactccgcga atctcgtat gccgtcttct    60 gcttg    65

<210> SEQ ID NO 61
<211> LENGTH: 65
<212> TYPE: DNA
<213> ORGANISM: Artificial Sequence
<220> FEATURE:
<223> OTHER INFORMATION: Synthetic construct

<400> SEQUENCE: 61
gatcggaaga gcacacgtct gaactccagt cactctcgcg catctcgtat gccgtcttct    60
gcttg    65

<210> SEQ ID NO 62
<211> LENGTH: 65
<212> TYPE: DNA
<213> ORGANISM: Artificial Sequence
<220> FEATURE:
<223> OTHER INFORMATION: Synthetic construct

<400> SEQUENCE: 62
gatcggaaga gcacacgtct gaactccagt cacagcgata gatctcgtat gccgtcttct    60
gcttg                                                                65

<210> SEQ ID NO 63
<211> LENGTH: 10
<212> TYPE: DNA
<213> ORGANISM: Artificial Sequence
<220> FEATURE:
<223> OTHER INFORMATION: Synthetic construct

<400> SEQUENCE: 63
ctcagcctcc                                                            10

<210> SEQ ID NO 64
<211> LENGTH: 10
<212> TYPE: DNA
<213> ORGANISM: Artificial Sequence
<220> FEATURE:
<223> OTHER INFORMATION: Synthetic construct

<400> SEQUENCE: 64
cctcagcctc                                                            10

<210> SEQ ID NO 65
<211> LENGTH: 10
<212> TYPE: DNA
<213> ORGANISM: Artificial Sequence
<220> FEATURE:
<223> OTHER INFORMATION: Synthetic construct

<400> SEQUENCE: 65
gcctcagcct                                                            10

<210> SEQ ID NO 66
<211> LENGTH: 10
<212> TYPE: DNA
<213> ORGANISM: Artificial Sequence
<220> FEATURE:
<223> OTHER INFORMATION: Synthetic construct

<400> SEQUENCE: 66
gcctcccaaa                                                            10

<210> SEQ ID NO 67
<211> LENGTH: 10
<212> TYPE: DNA
<213> ORGANISM: Artificial Sequence
<220> FEATURE:
<223> OTHER INFORMATION: Synthetic construct

<400> SEQUENCE: 67
tcagcctccc                                                            10

<210> SEQ ID NO 68
<211> LENGTH: 10
<212> TYPE: DNA

```
<213> ORGANISM: Artificial Sequence
<220> FEATURE:
<223> OTHER INFORMATION: Synthetic construct

<400> SEQUENCE: 68
cctcccaaag                                                          10

<210> SEQ ID NO 69
<211> LENGTH: 10
<212> TYPE: DNA
<213> ORGANISM: Artificial Sequence
<220> FEATURE:
<223> OTHER INFORMATION: Synthetic construct

<400> SEQUENCE: 69
tttgtatttt                                                          10

<210> SEQ ID NO 70
<211> LENGTH: 10
<212> TYPE: DNA
<213> ORGANISM: Artificial Sequence
<220> FEATURE:
<223> OTHER INFORMATION: Synthetic constrcut

<400> SEQUENCE: 70
ttttgtattt                                                          10

<210> SEQ ID NO 71
<211> LENGTH: 10
<212> TYPE: DNA
<213> ORGANISM: Artificial Sequence
<220> FEATURE:
<223> OTHER INFORMATION: Synthetic construct

<400> SEQUENCE: 71
aggctggagt                                                          10

<210> SEQ ID NO 72
<211> LENGTH: 10
<212> TYPE: DNA
<213> ORGANISM: Artificial Sequence
<220> FEATURE:
<223> OTHER INFORMATION: Synthetic construct

<400> SEQUENCE: 72
gctcactgca                                                          10

<210> SEQ ID NO 73
<211> LENGTH: 10
<212> TYPE: DNA
<213> ORGANISM: Artificial Sequence
<220> FEATURE:
<223> OTHER INFORMATION: Synthetic construct

<400> SEQUENCE: 73
gtagctggga                                                          10

<210> SEQ ID NO 74
<211> LENGTH: 10
<212> TYPE: DNA
<213> ORGANISM: Artificial Sequence
<220> FEATURE:
<223> OTHER INFORMATION: Synthetic construct

<400> SEQUENCE: 74
tgcctcagcc                                                          10
```

<210> SEQ ID NO 75
<211> LENGTH: 10
<212> TYPE: DNA
<213> ORGANISM: Artificial Sequence
<220> FEATURE:
<223> OTHER INFORMATION: Synthetic construct

<400> SEQUENCE: 75
agtagctggg                                                            10

<210> SEQ ID NO 76
<211> LENGTH: 10
<212> TYPE: DNA
<213> ORGANISM: Artificial Sequence
<220> FEATURE:
<223> OTHER INFORMATION: Synthetic construct

<400> SEQUENCE: 76
caggctggag                                                            10

<210> SEQ ID NO 77
<211> LENGTH: 10
<212> TYPE: DNA
<213> ORGANISM: Artificial Sequence
<220> FEATURE:
<223> OTHER INFORMATION: Synthetic construct

<400> SEQUENCE: 77
ccaaagtgct                                                            10

<210> SEQ ID NO 78
<211> LENGTH: 10
<212> TYPE: DNA
<213> ORGANISM: Artificial Sequence
<220> FEATURE:
<223> OTHER INFORMATION: Synthetic construct

<400> SEQUENCE: 78
ctggagtgca                                                            10

<210> SEQ ID NO 79
<211> LENGTH: 10
<212> TYPE: DNA
<213> ORGANISM: Artificial Sequence
<220> FEATURE:
<223> OTHER INFORMATION: Synthetic construct

<400> SEQUENCE: 79
tgctgggatt                                                            10

<210> SEQ ID NO 80
<211> LENGTH: 10
<212> TYPE: DNA
<213> ORGANISM: Artificial Sequence
<220> FEATURE:
<223> OTHER INFORMATION: Synthetic construct

<400> SEQUENCE: 80
ggctggagtg                                                            10

<210> SEQ ID NO 81
<211> LENGTH: 10
<212> TYPE: DNA
<213> ORGANISM: Artificial Sequence
<220> FEATURE:

<223> OTHER INFORMATION: Synthetic construct

<400> SEQUENCE: 81
ctgcctcagc                                                              10

<210> SEQ ID NO 82
<211> LENGTH: 10
<212> TYPE: DNA
<213> ORGANISM: Artificial Sequence
<220> FEATURE:
<223> OTHER INFORMATION: Synthetic construct

<400> SEQUENCE: 82
gctggagtgc                                                              10

<210> SEQ ID NO 83
<211> LENGTH: 10
<212> TYPE: DNA
<213> ORGANISM: Artificial Sequence
<220> FEATURE:
<223> OTHER INFORMATION: Synthetic construct

<400> SEQUENCE: 83
aaagtgctgg                                                              10

<210> SEQ ID NO 84
<211> LENGTH: 10
<212> TYPE: DNA
<213> ORGANISM: Artificial Sequence
<220> FEATURE:
<223> OTHER INFORMATION: Synthetic construct

<400> SEQUENCE: 84
cctgcctcag                                                              10

<210> SEQ ID NO 85
<211> LENGTH: 10
<212> TYPE: DNA
<213> ORGANISM: Artificial Sequence
<220> FEATURE:
<223> OTHER INFORMATION: Synthetic construct

<400> SEQUENCE: 85
gtgctgggat                                                              10

<210> SEQ ID NO 86
<211> LENGTH: 10
<212> TYPE: DNA
<213> ORGANISM: Artificial Sequence
<220> FEATURE:
<223> OTHER INFORMATION: Synthetic construct

<400> SEQUENCE: 86
agtgctggga                                                              10

<210> SEQ ID NO 87
<211> LENGTH: 10
<212> TYPE: DNA
<213> ORGANISM: Artificial Sequence
<220> FEATURE:
<223> OTHER INFORMATION: Synthetic construct

<400> SEQUENCE: 87
aagtgctggg                                                              10

```
<210> SEQ ID NO 88
<211> LENGTH: 10
<212> TYPE: DNA
<213> ORGANISM: Artificial Sequence
<220> FEATURE:
<223> OTHER INFORMATION: Synthetic construct

<400> SEQUENCE: 88
ctcactgcaa                                                                10

<210> SEQ ID NO 89
<211> LENGTH: 10
<212> TYPE: DNA
<213> ORGANISM: Artificial Sequence
<220> FEATURE:
<223> OTHER INFORMATION: Synthetic construct

<400> SEQUENCE: 89
tcctgcctca                                                                10

<210> SEQ ID NO 90
<211> LENGTH: 10
<212> TYPE: DNA
<213> ORGANISM: Artificial Sequence
<220> FEATURE:
<223> OTHER INFORMATION: Synthetic construct

<400> SEQUENCE: 90
tggagtgcag                                                                10

<210> SEQ ID NO 91
<211> LENGTH: 10
<212> TYPE: DNA
<213> ORGANISM: Artificial Sequence
<220> FEATURE:
<223> OTHER INFORMATION: Synthetic construct

<400> SEQUENCE: 91
tctcctgcct                                                                10

<210> SEQ ID NO 92
<211> LENGTH: 10
<212> TYPE: DNA
<213> ORGANISM: Artificial Sequence
<220> FEATURE:
<223> OTHER INFORMATION: Synthetic construct

<400> SEQUENCE: 92 tttttttgaga                                                               10

<210> SEQ ID NO 93
<211> LENGTH: 10
<212> TYPE: DNA
<213> ORGANISM: Artificial Sequence
<220> FEATURE:
<223> OTHER INFORMATION: Synthetic construct

<400> SEQUENCE: 93
ttctcctgcc                                                                10

<210> SEQ ID NO 94
<211> LENGTH: 10
<212> TYPE: DNA
<213> ORGANISM: Artificial Sequence
<220> FEATURE:
<223> OTHER INFORMATION: Synthetic construct
```

```
<400> SEQUENCE: 94
attctcctgc                                                                10

<210> SEQ ID NO 95
<211> LENGTH: 10
<212> TYPE: DNA
<213> ORGANISM: Artificial Sequence
<220> FEATURE:
<223> OTHER INFORMATION: Synthetic construct

<400> SEQUENCE: 95
ggcctcccaa                                                                10

<210> SEQ ID NO 96
<211> LENGTH: 10
<212> TYPE: DNA
<213> ORGANISM: Artificial Sequence
<220> FEATURE:
<223> OTHER INFORMATION: Synthetic construct

<400> SEQUENCE: 96
tttttttgag                                                                10

<210> SEQ ID NO 97
<211> LENGTH: 10
<212> TYPE: DNA
<213> ORGANISM: Artificial Sequence
<220> FEATURE:
<223> OTHER INFORMATION: Synthetic construct

<400> SEQUENCE: 97
tttttttga                                                                 10

<210> SEQ ID NO 98
<211> LENGTH: 10
<212> TYPE: DNA
<213> ORGANISM: Artificial Sequence
<220> FEATURE:
<223> OTHER INFORMATION: Synthetic construct

<400> SEQUENCE: 98
cagcctccca                                                                10

<210> SEQ ID NO 99
<211> LENGTH: 10
<212> TYPE: DNA
<213> ORGANISM: Artificial Sequence
<220> FEATURE:
<223> OTHER INFORMATION: Synthetic construct

<400> SEQUENCE: 99
agcctcccaa                                                                10

<210> SEQ ID NO 100
<211> LENGTH: 10
<212> TYPE: DNA
<213> ORGANISM: Artificial Sequence
<220> FEATURE:
<223> OTHER INFORMATION: Synthetic construct

<400> SEQUENCE: 100
gagtagctgg                                                                10

<210> SEQ ID NO 101
<211> LENGTH: 10
```

```
<212> TYPE: DNA
<213> ORGANISM: Artificial Sequence
<220> FEATURE:
<223> OTHER INFORMATION: Synthetic construct

<400> SEQUENCE: 101
tcactgcaac                                                          10

<210> SEQ ID NO 102
<211> LENGTH: 10
<212> TYPE: DNA
<213> ORGANISM: Artificial Sequence
<220> FEATURE:
<223> OTHER INFORMATION: Synthetic construct

<400> SEQUENCE: 102
ggattacagg                                                          10

<210> SEQ ID NO 103
<211> LENGTH: 10
<212> TYPE: DNA
<213> ORGANISM: Artificial Sequence
<220> FEATURE:
<223> OTHER INFORMATION: Synthetic construct

<400> SEQUENCE: 103
ggctcactgc                                                          10

<210> SEQ ID NO 104
<211> LENGTH: 10
<212> TYPE: DNA
<213> ORGANISM: Artificial Sequence
<220> FEATURE:
<223> OTHER INFORMATION: Synthetic construct

<400> SEQUENCE: 104
actgcaacct                                                          10

<210> SEQ ID NO 105
<211> LENGTH: 10
<212> TYPE: DNA
<213> ORGANISM: Artificial Sequence
<220> FEATURE:
<223> OTHER INFORMATION: Synthetic construct

<400> SEQUENCE: 105
ctgcaacctc                                                          10

<210> SEQ ID NO 106
<211> LENGTH: 10
<212> TYPE: DNA
<213> ORGANISM: Artificial Sequence
<220> FEATURE:
<223> OTHER INFORMATION: Synthetic construct

<400> SEQUENCE: 106
cactgcaacc                                                          10

<210> SEQ ID NO 107
<211> LENGTH: 10
<212> TYPE: DNA
<213> ORGANISM: Artificial Sequence
<220> FEATURE:
<223> OTHER INFORMATION: Synthetic construct

<400> SEQUENCE: 107
```

```
taattttgt                                                              10

<210> SEQ ID NO 108
<211> LENGTH: 10
<212> TYPE: DNA
<213> ORGANISM: Artificial Sequence
<220> FEATURE:
<223> OTHER INFORMATION: Synthetic construct

<400> SEQUENCE: 108
gggattacag                                                             10

<210> SEQ ID NO 109
<211> LENGTH: 10
<212> TYPE: DNA
<213> ORGANISM: Artificial Sequence
<220> FEATURE:
<223> OTHER INFORMATION: Synthetic construct

<400> SEQUENCE: 109
gggtttcacc                                                             10

<210> SEQ ID NO 110
<211> LENGTH: 116
<212> TYPE: DNA
<213> ORGANISM: Artificial Sequence
<220> FEATURE:
<223> OTHER INFORMATION: Synthetic construct

<400> SEQUENCE: 110
ctctctgggt aaccacatgc ttaagaacaa tctatacttt aagaatctga cttactggaa      60
gggctagttt ggtcccagaa aagacaagac atccttgatt tgtgggtcta ccacac        116

<210> SEQ ID NO 111
<211> LENGTH: 63
<212> TYPE: DNA
<213> ORGANISM: Artificial Sequence
<220> FEATURE:
<223> OTHER INFORMATION: Synthetic construct

<400> SEQUENCE: 111
actggaaggg ctagtttggt cccagaaaag acaagacatc cttgatttgt gggtctacca      60
cac                                                                    63

<210> SEQ ID NO 112
<211> LENGTH: 121
<212> TYPE: DNA
<213> ORGANISM: Artificial Sequence
<220> FEATURE:
<223> OTHER INFORMATION: Synthetic construct

<400> SEQUENCE: 112
gcatttcata tccttccat gacaagtatt caggggggag cccaacaaga ttaccttact       60
ggaagggcta gtttggtccc agaaaagaca agacatcctt gatttgtggg tctaccacac    120
a                                                                    121

<210> SEQ ID NO 113
<211> LENGTH: 62
<212> TYPE: DNA
<213> ORGANISM: Artificial Sequence
<220> FEATURE:
<223> OTHER INFORMATION: Synthetic construct

<400> SEQUENCE: 113
```

```
tggaagggct agtttggtcc cagaaaagac aagacatcct tgatttgtgg gtctaccaca      60
ca                                                                    62

<210> SEQ ID NO 114
<211> LENGTH: 119
<212> TYPE: DNA
<213> ORGANISM: Artificial Sequence
<220> FEATURE:
<223> OTHER INFORMATION: Synthetic construct

<400> SEQUENCE: 114
gcccttaaga ccaatgactt acaagggagc tttagatctt agccactttt taaaagaaaa      60 gggggactg gaagggctag tttggtccca gaaaagacaa gacatccttg atttgtggg      119

<210> SEQ ID NO 115
<211> LENGTH: 51
<212> TYPE: DNA
<213> ORGANISM: Artificial Sequence
<220> FEATURE:
<223> OTHER INFORMATION: Synthetic construct

<400> SEQUENCE: 115
tggaagggct agtttggtcc cagaaaagac aagacatcct tgatttgtgg g               51
```

INTEGRATED PROVIRAL SEQUENCING ASSAY

The application is a national stage application filed under 35 U.S.C. § 371 of PCT/US2019/065945, filed on Dec. 12, 2019, which claims the benefit of U.S. Provisional Application No. 62/778,480, filed on Dec. 12, 2018, applications which are incorporated herein by reference in their entireties.

I. BACKGROUND

Many viruses while infecting a cell insert their genetic material into the host genome. This can be done as a necessary action for viral replication, as is the case for retroviruses, or to provide for viral escape of the host immune response and form a latent infection as occurs with herpesviruses. The identification and characterization of viral nucleic acid that has integrated into the host genome and the site of integration into the host genome is an important step in the detection and characterization of integrated viruses. Prior attempts to identify the presence of such rare integrations (around 1 provirus in 1000 human genomes in the case of HIV) have not been successfully amplified in a manner that provides both sufficient host and proviral DNA sequence to identify the integration site and characterize the integrated provirus including whether it is intact (i.e., absence of insertions, deletions, stop codons or other lethal change) and its phylogenetic relationship to proviruses in other cells or other individuals. What is needed are new tools and methods for the identification of integrated proviral nucleic acid that can both characterize the integrated nucleic acid and identify its location in the host genome.

II. SUMMARY

Disclosed are novel adaptor molecules and methods of their use.

In one aspect, disclosed herein are synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40).

Also disclosed herein are kits for detecting the presence of viral nucleic acid in an integrated location in the genome of a host comprising the synthetic oligonucleotide of any preceding aspect.

In one aspect disclosed herein are methods of detecting the presence and location of a viral nucleic acid integrated into the genome of a host comprising a) a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39) and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a near full length proviral amplification; and b) sequencing and aligning the amplicons generated by the first and second amplification reactions.

In one aspect, disclosed herein are methods of detecting the presence and location of a viral nucleic acid integrated into the genome of a host of any preceding aspect, the method further comprising a) performing whole genome amplification on proviral end point diluted genomic DNA from the host; b) performing a near full length proviral amplification on the DNA generated by the whole genome amplification reaction; c) construct a library of amplicons using the generated WGA DNA, from step a, which was identified to contain a provirus from step b; d) performing a viral specific nested PCR on library; and e) sequence the amplicons of step b and step d. Also disclosed are methods detecting the presence and location of a viral nucleic acid integrated into the genome of a host wherein the viral specific nested PCR of step d can comprise ligating an adaptor molecule to an unamplified genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer.

Also disclosed herein are methods of detecting the presence and location of an integrated proviral nucleic acid of any preceding aspect, wherein the viral nucleic acid is from a virus from the viral family Retroviridae (such as, for example, a lentivirus (including, but not limited to Human Immunodeficiency Virus, or deltaretrovirus), or Hepadnaviridae (such as, for example, a Hepatitis B virus), Herpesviridae (such as, for example, Herpes Simplex Virus-1, Herpes Simplex Virus-2, Varicella-zoster virus, Epstein-Barr virus, Cytomegalovirus, Human Herpes Virus 6A, Human Herpes Virus 6B, Human Herpes Virus 7, and Human Herpes Virus 8).

In one aspect, disclosed herein are methods of distinguishing a non-functional integrated sequences (i.e., a partial or mutated sequence) from a functional sequence comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length viral amplification; b) sequencing and aligning the amplicons generated by the first and second amplification reactions; and c) assembling any aligned integrated proviral sequence to a known full length viral sequence; wherein a sequence comprising truncations, mutations, deletions, or additions in the viral genome are not functional integrated viruses.

In one aspect, disclosed herein are methods of assaying the efficacy of an antiviral treatment, the method comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; and c) assembling any aligned integrated proviral sequence to a known full length viral sequence; wherein a reduction in the amount of functional integrated provirus or virus relative to a control or absence of integrated virus or provirus indicates that the anti-viral was efficacious.

Also disclosed herein are methods of diagnosing a subject with a latent viral infection, the method comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a near full length proviral amplification; b) sequencing and aligning the amplicons generated by the first and second amplification reactions; and c) aligning any aligned integrated proviral sequence to a known full viral sequence; wherein the identification of a viral or proviral sequence absent any truncations, mutations, deletions, or additions in the viral genome indicates a latent viral infection.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 4:
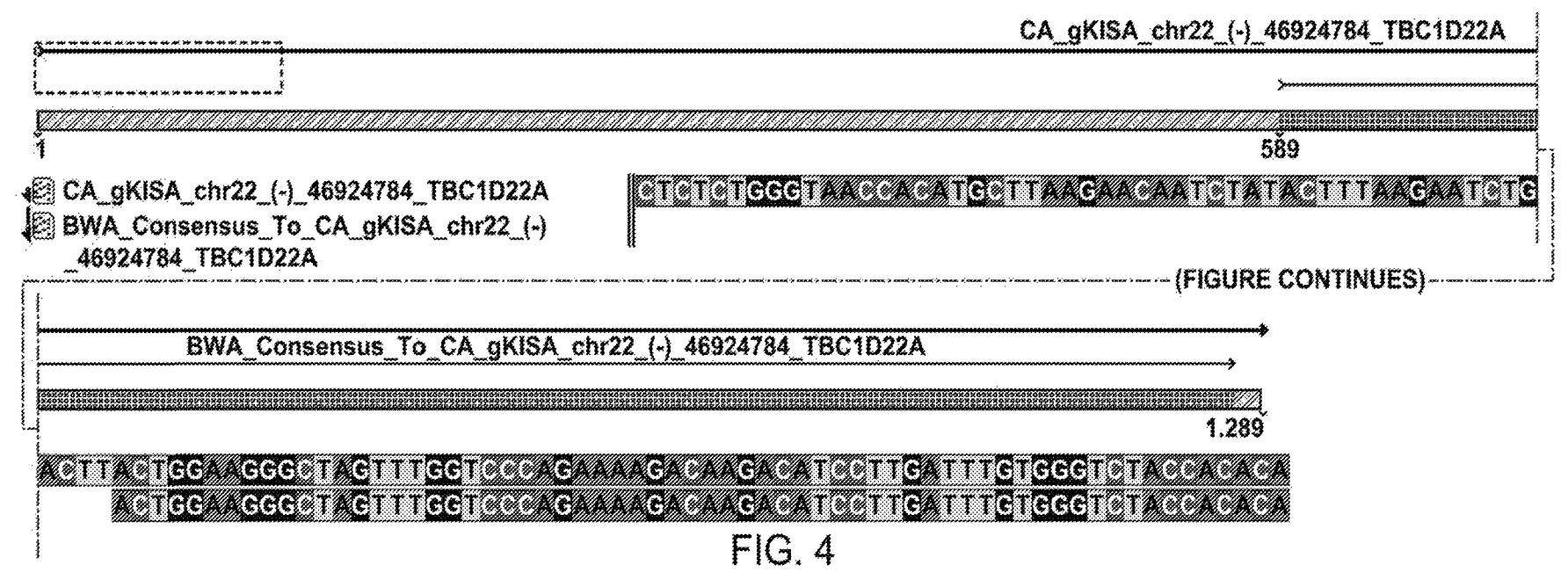

FIG. 4 shows the first example of the integrated viral sequencing assay (IVSA) consisting of overlapping near-full length viral genomic sequences with the additional viral sequences and the host integration site needed to characterize a full-length viral sequence and its integration site in the human genome from donor CA. FIG. 4 specifically shows the 5' LTR from near-full length HIV proviral amplicon (SEQ ID NO: 110) and integration site amplicon (SEQ ID NO: 111). This also shows the alignment of the protruding host sequence and 5' LTR aligned against the LTR sequence generated from the larger proviral amplicon.

Figure 5:
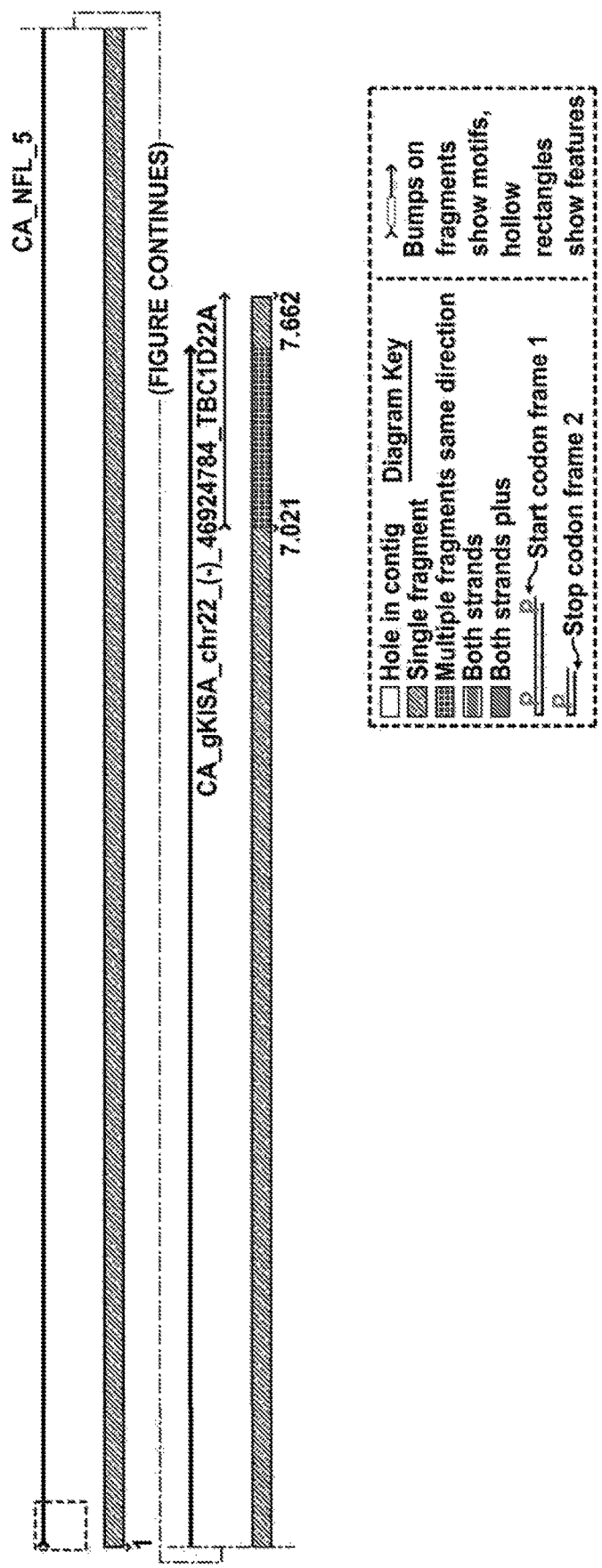

FIG. 5 shows the first example of integrated viral sequences aligned from donor CA. FIG. 5 shows the alignment of the proviral amplicon with integration site amplicon below, CA_NFL5 is large proviral amplicon sequence.

Figure 6:
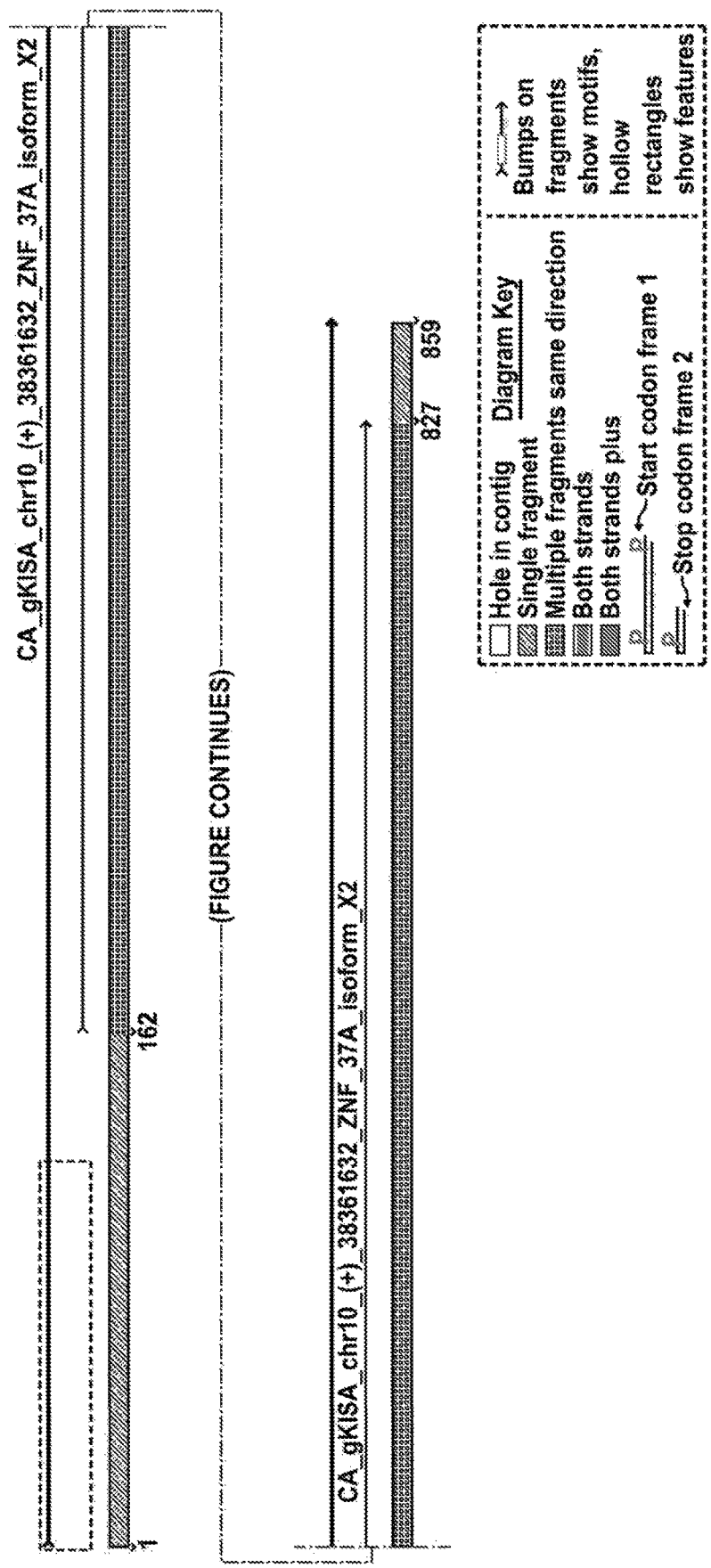

FIG. 6 shows the second example of the IVSA from donor CA. FIG. 6 shows the alignment of the protruding host sequence and 5' LTR (SEQ ID NO: 113) aligned against the LTR sequence generated from the larger proviral amplicon (SEQ ID NO: 112).

Figure 7:
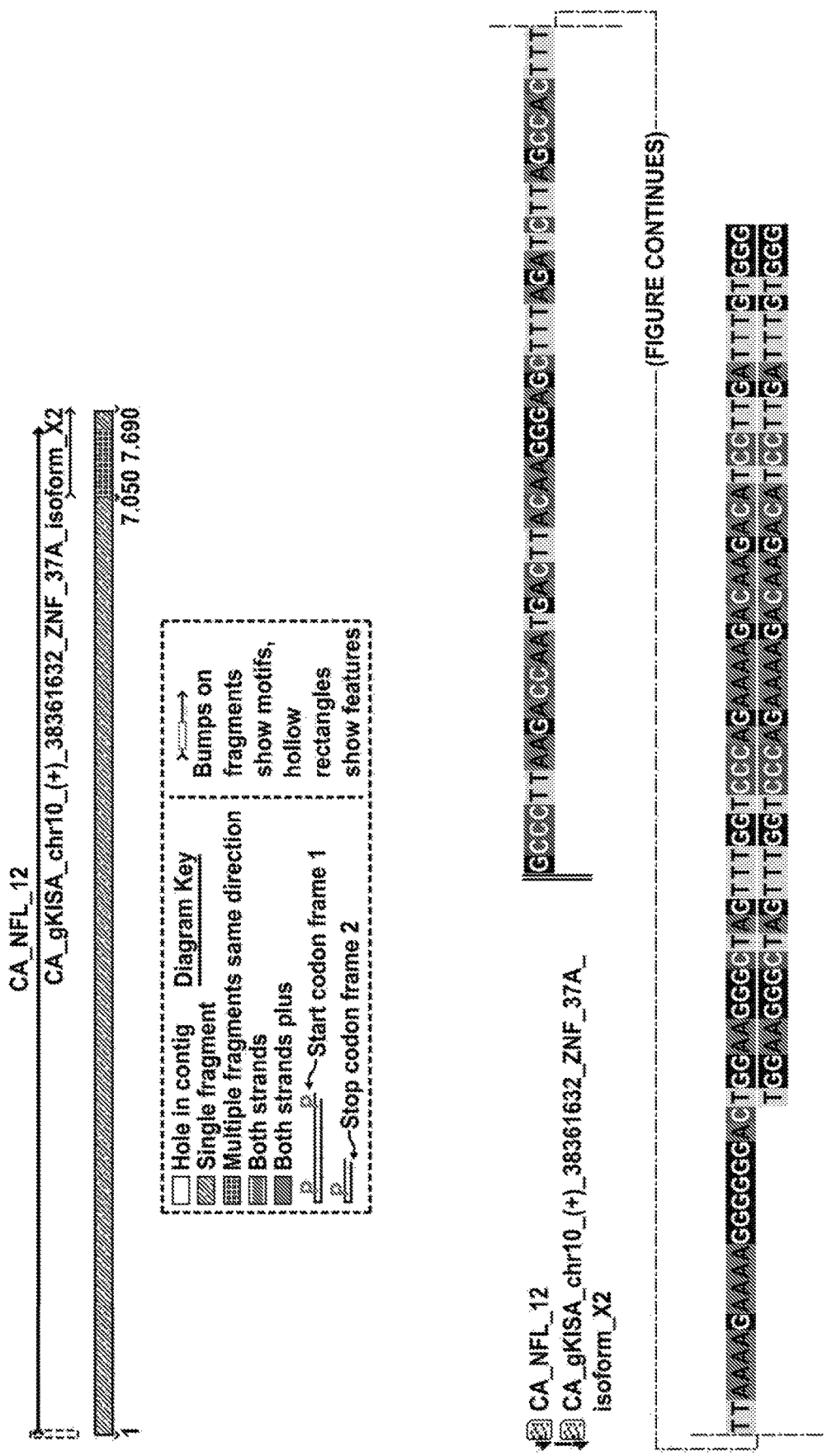

FIG. 7 shows the second example of integrated viral sequences aligned from donors CA. FIG. 7 shows the alignment of the NFLPAS amplicon (SEQ ID NO: 114) with integration site amplicon below (SEQ ID NO: 115), CA_NFL12 is large proviral sequence. The host sequence was removed to demonstrate that the two separate amplicons align perfectly.

Figure 8:
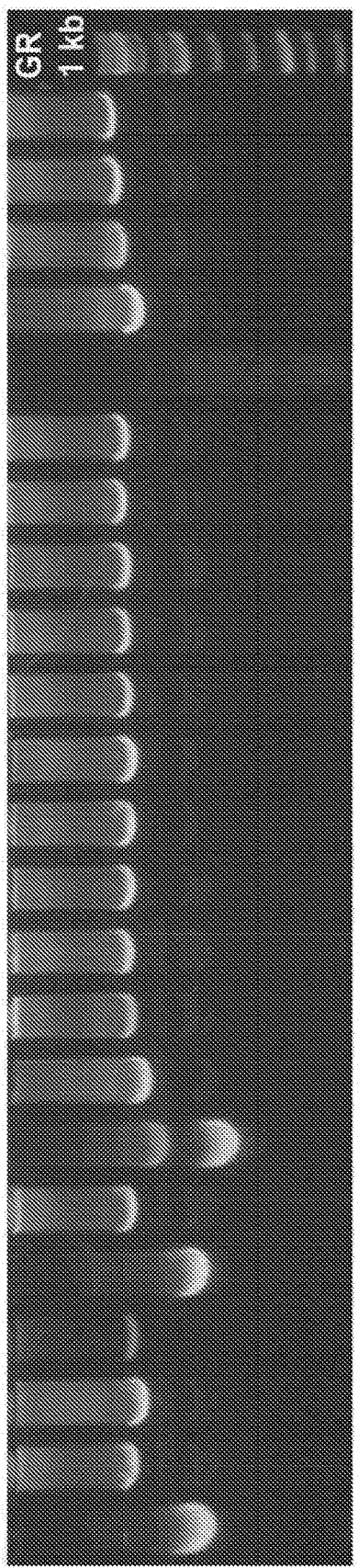

FIG. 8 shows a 0.8% sodium borate gel showing variable length proviral amplicons.

Figure 9:
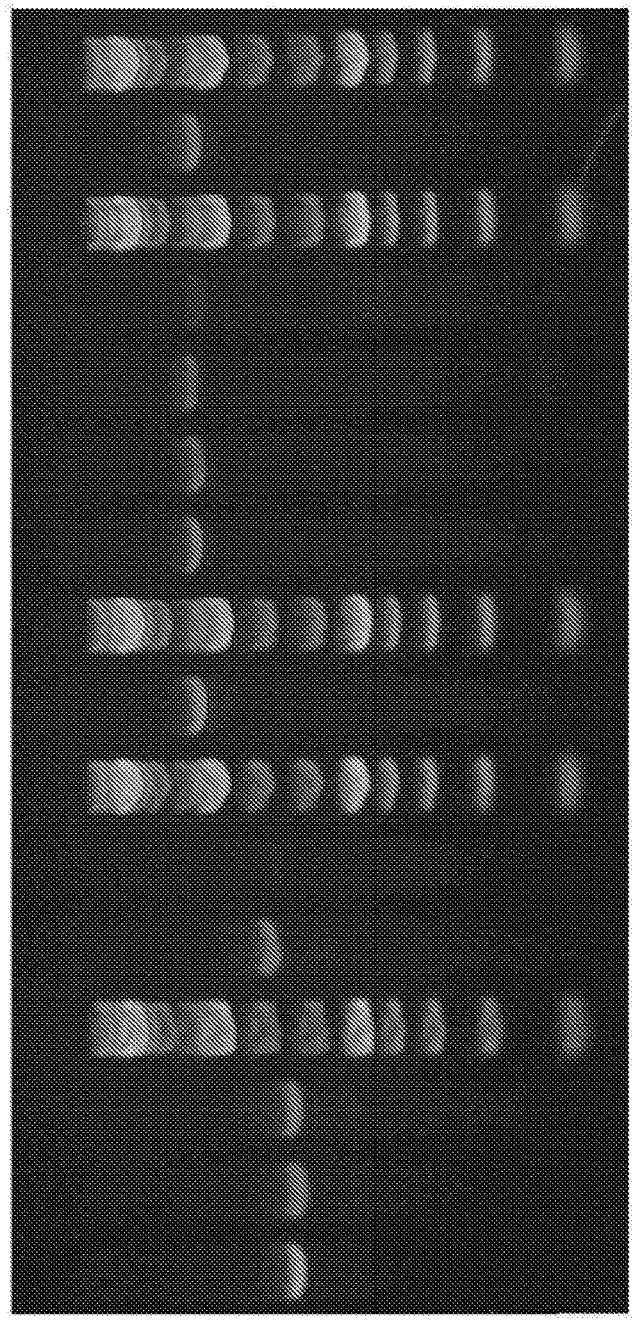

FIG. 9 shows a 0.8% sodium borate gel showing host-virus junction enriched amplicons.

Figure 10:
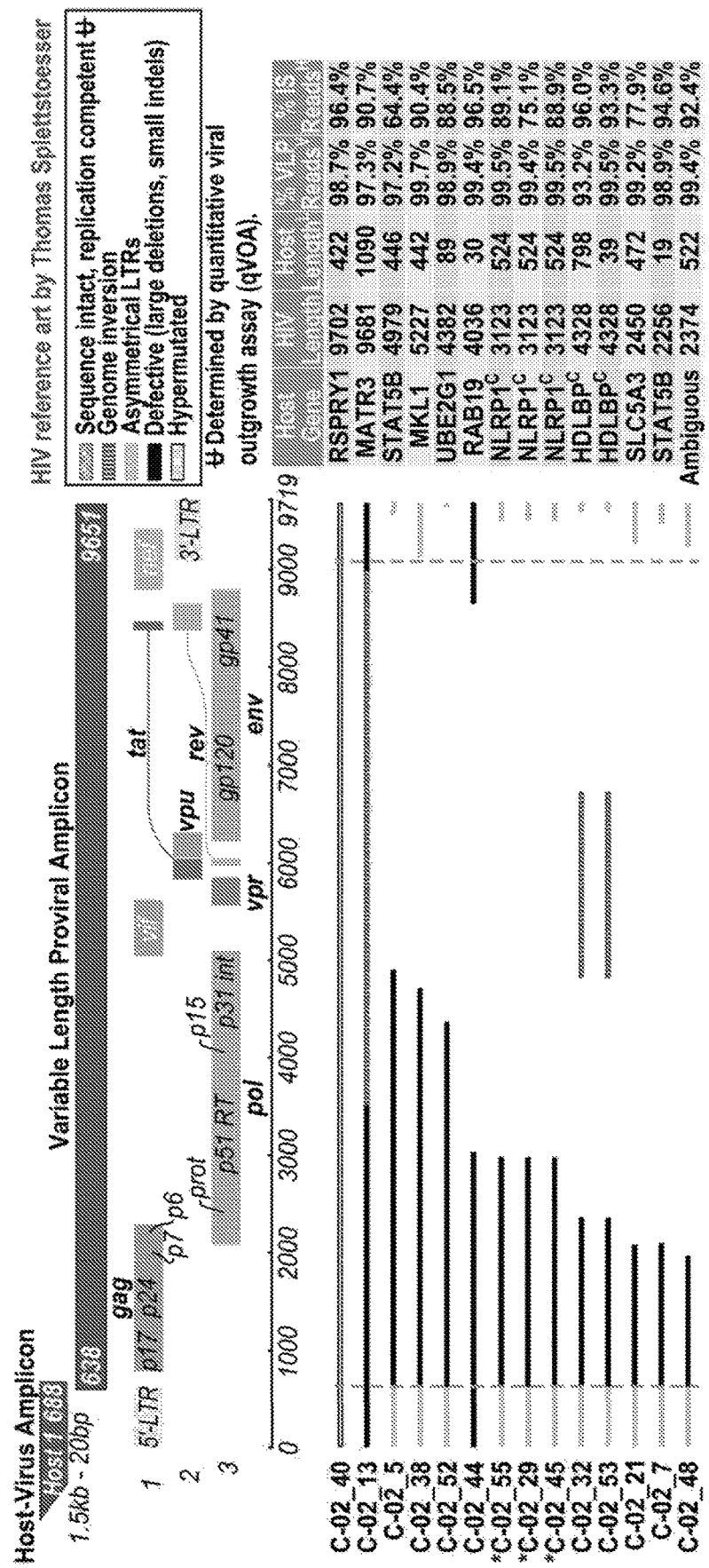
Figure 10:
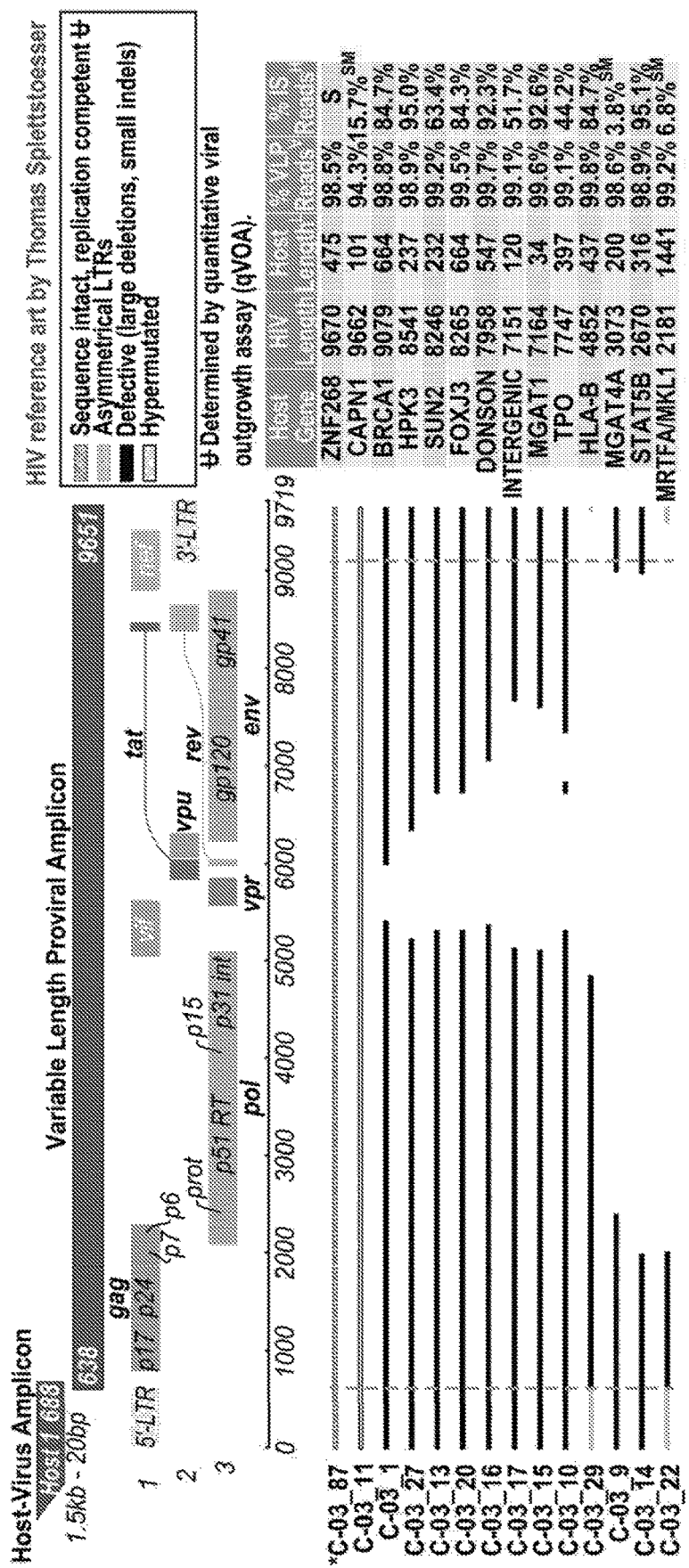
Figure 10:
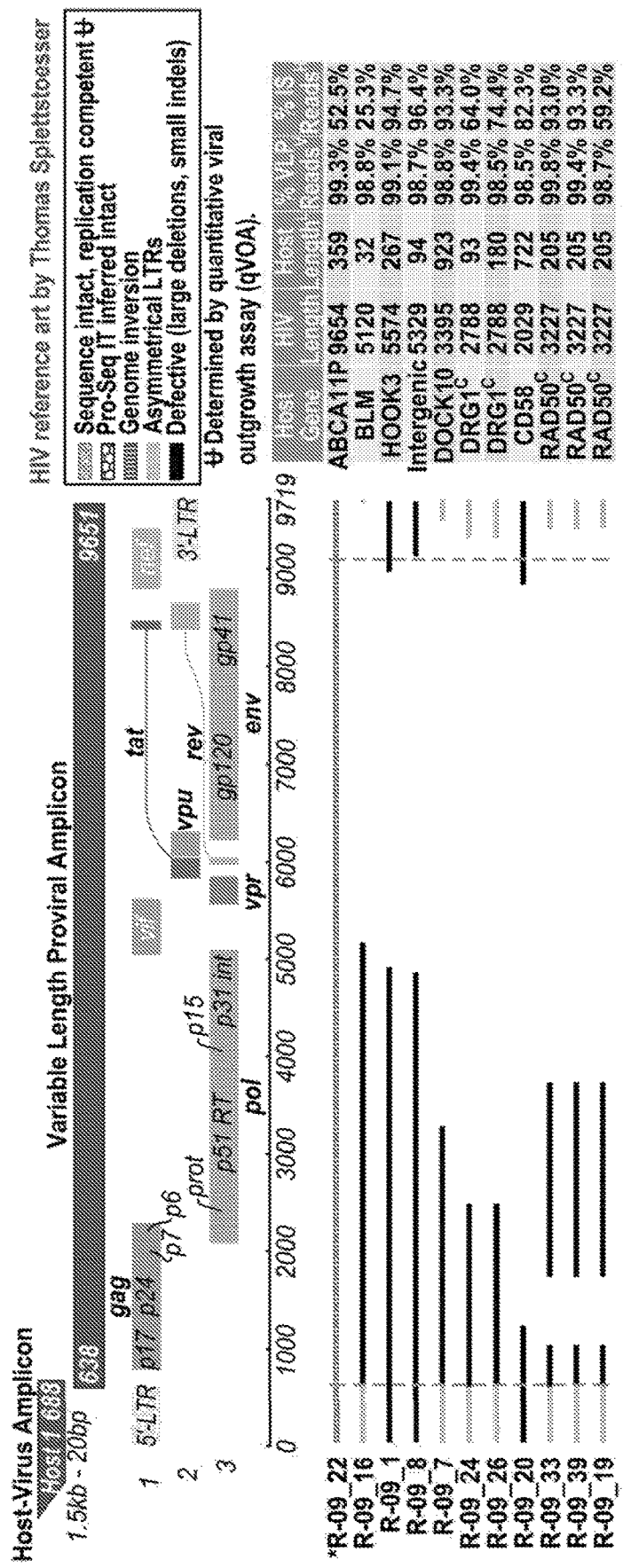
Figure 10:
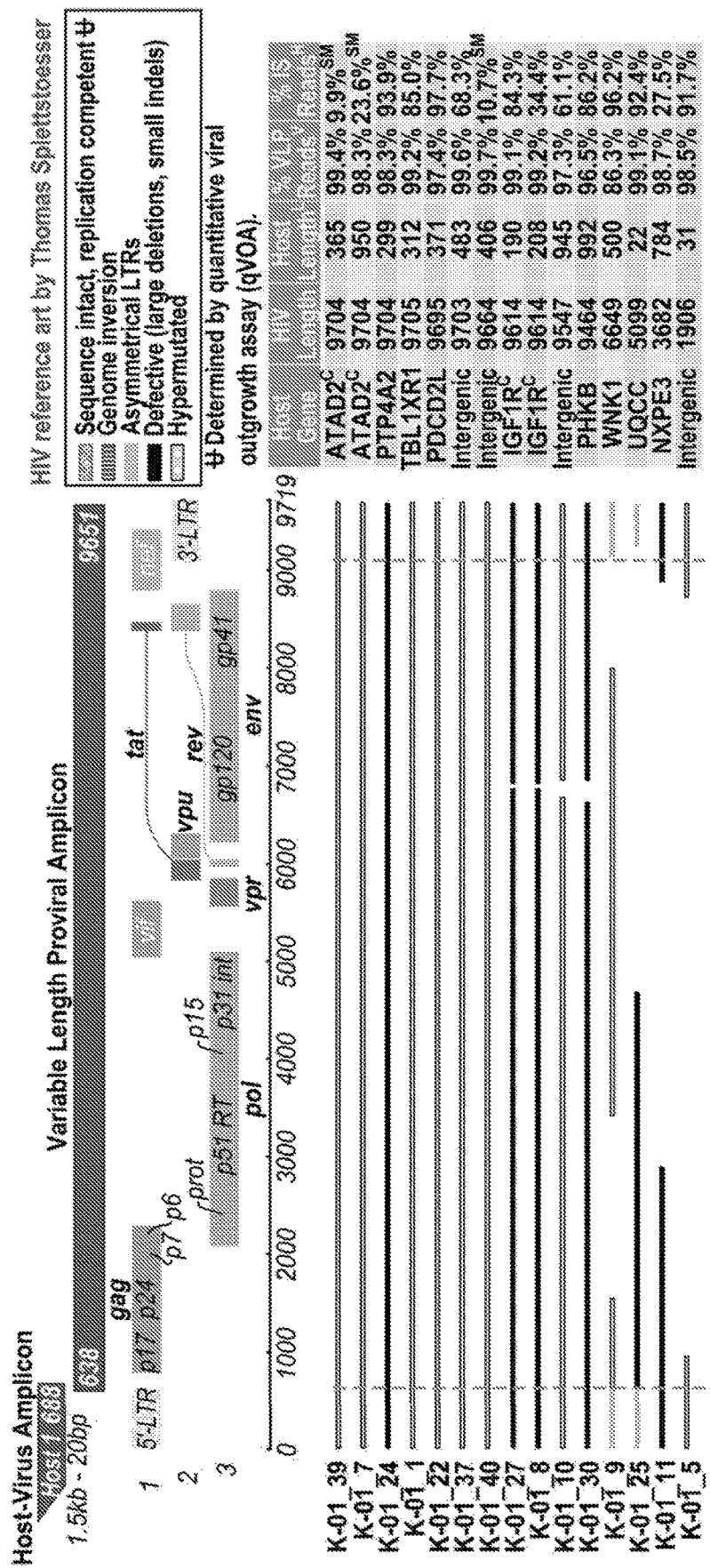
Figure 10:
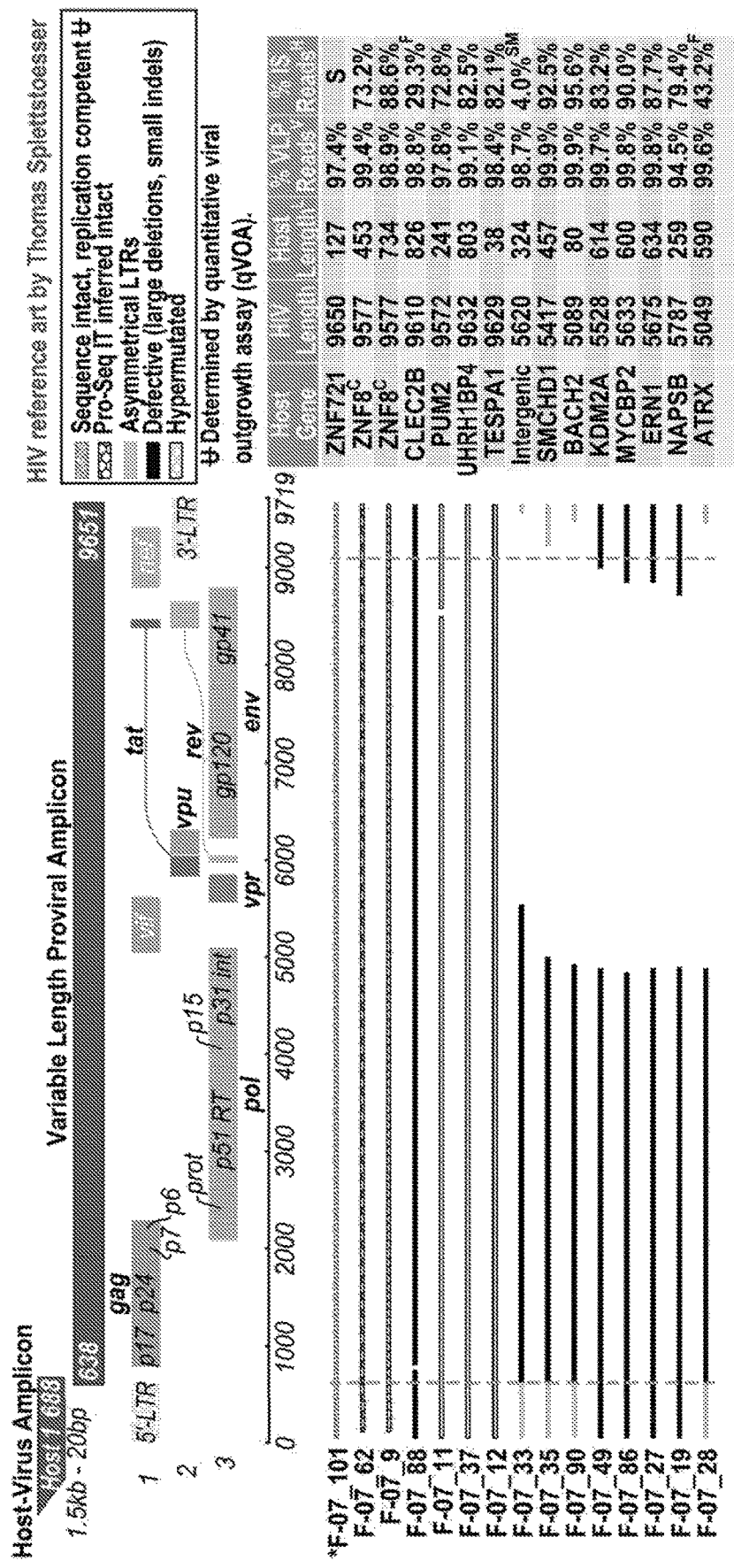
Figure 10:
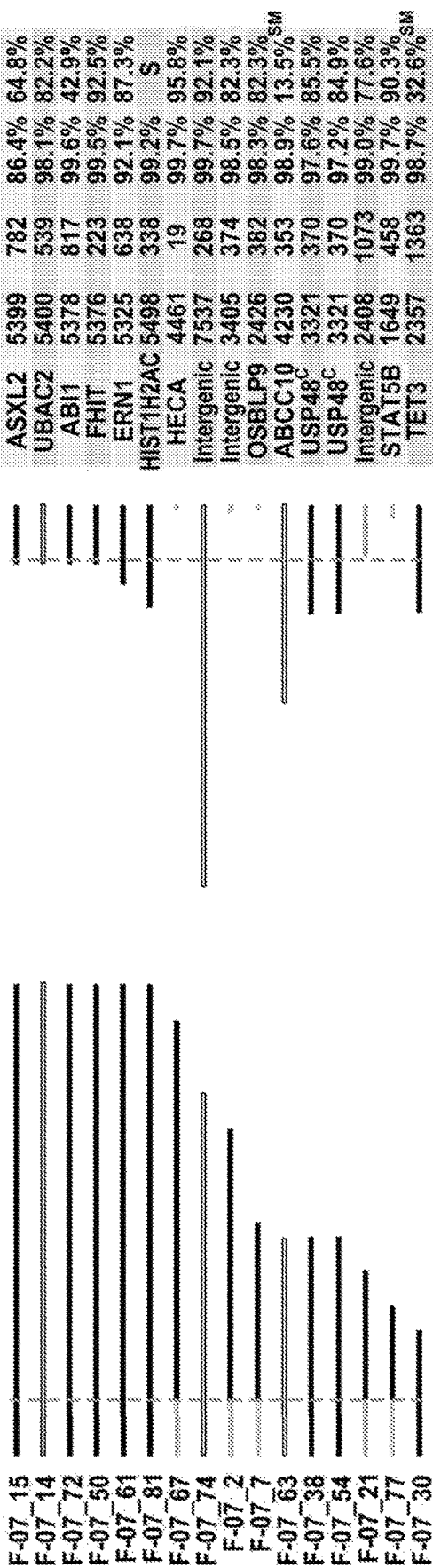

FIG. 10 shows donor-specific virograms depicting assembled proviruses containing matching variable length provirus and integration site amplicons. Alignment of consensus assemblies was performed using MUSCLE. Each row of the table corresponds to the provirus to the left. Blue dashed lines denote LTR borders. *, denotes proviruses with sequence identity validated using gene-specific integration site PCR from unamplified genomic DNA. $^C$, denotes clonally expanded proviruses. $^L$, denotes length of amplified flanking host sequence. $^V$, denotes the percentage of total reads utilized during assembly of variable length provirus amplicon (VLPAS). $^H$, denotes the percentage of total reads utilized during assembly of host-virus junction containing amplicon (IS). $^S$, denotes integration sites sequenced by dideoxy-sequencing only. $^{SM}$, denotes amplicons in which 10 ng of a smear with no defined amplicon band by agarose gel analysis was sequenced.

Figure 11A:
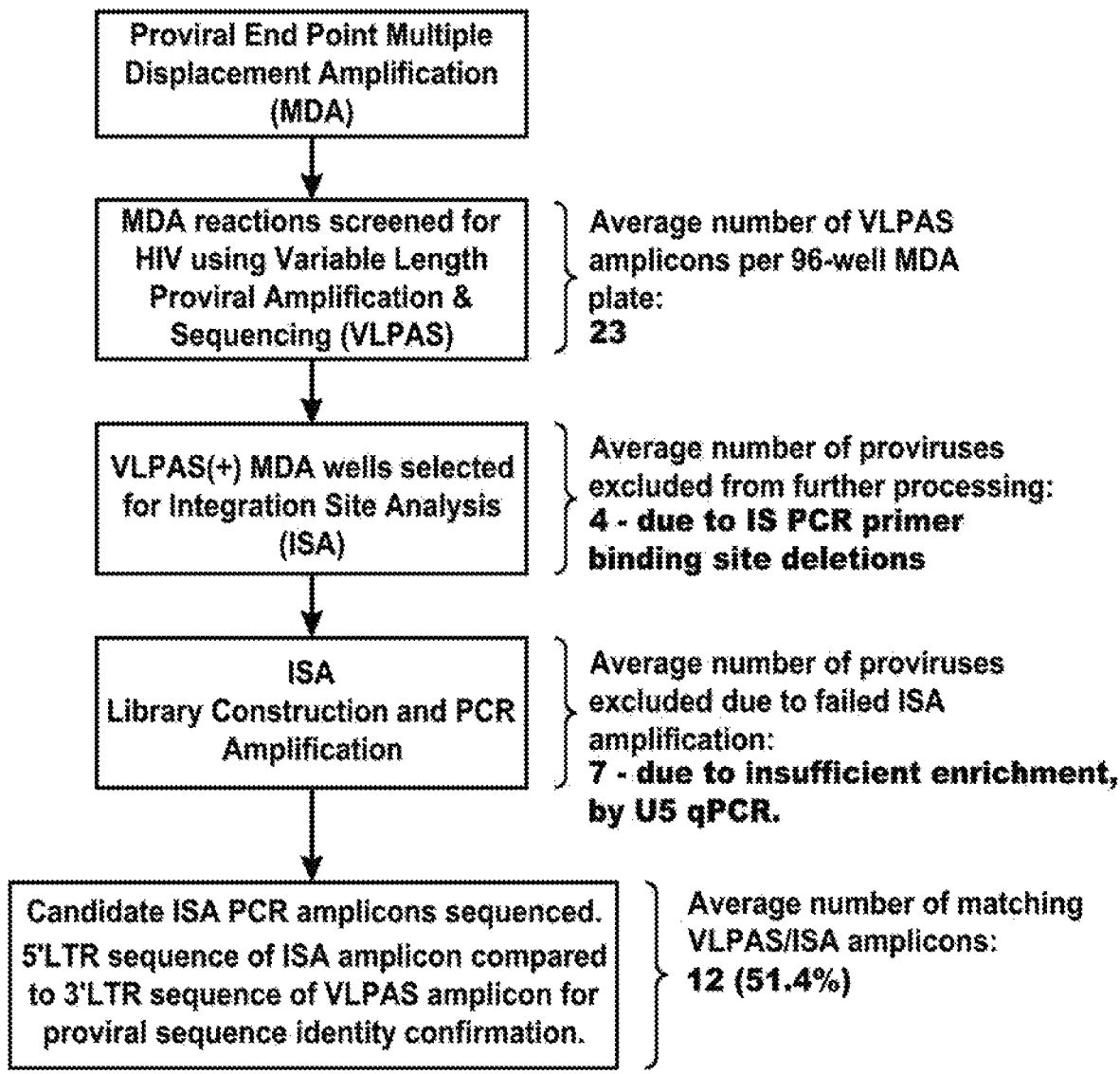

FIGS. 11A and 11B show the overall (11A) and donor-specific (11B) proviral enrichment efficiencies. $^A$ Number of MDA wells that produced VLPAS and IS amplicons that did not have 5'/3'-LTR sequence identity issues. $^B$ Percentage of MDA wells that produced VLPAS and IS amplicons that did not have 5'/3'-LTR sequence identity issues. $^C$ Percentage of MDA wells that produced VLPAS and IS amplicons that both did and did not have 5'/3'-LTR sequence identity issues. D Mean and range length of 5' flanking host gene sequence upstream of integration site enriched and sequenced in base pairs.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

3' end: The end of a nucleic acid molecule that does not have a nucleotide bound to it 3' of the terminal residue.

5' end: The end of a nucleic acid sequence where the 5' position of the terminal residue is not bound by a nucleotide.

Amplification: A technique that increases the number of copies of a nucleic acid molecule (such as an RNA or DNA). An example of amplification is polymerase chain reaction (PCR), in which a sample is contacted with a pair of oligonucleotide primers under conditions that allow for the hybridization of the primers to a nucleic acid template in the sample. The primers are extended under suitable conditions (e.g., in the presence of a polymerase enzyme and dNTPs), dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences in a single reaction.

Biological sample: A sample of biological material obtained from a subject. Biological samples include all clinical samples useful for detection of disease or infection (e.g. a viral infection such as a HIV infection) in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchial alveolar lavage, semen, cerebrospinal fluid (CSF), etc.), tissue biopsies or autopsies, fine-needle aspirates, and/or tissue sections. In a particular example, a biological sample is obtained from a subject having, suspected of having or at risk of having HIV infection.

Complementary. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In particular examples disclosed herein, the complementary sequence is complementary at a labeled nucleotide, and at each nucleotide immediately flanking the labeled nucleotide.

Consists of or consists essentially of: with regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Contacting: Placement in direct physical association, for example solid, liquid or gaseous forms. Contacting includes, for example, direct physical association of fully- and partially-solvated molecules.

Control: A sample or standard used for comparison with an experimental sample. In some embodiments, the control is a sample obtained from a healthy patient, or a sample from a subject with HIV. In some embodiments, the control is a sample including HIV nucleic acid. In other embodiments, the control is a biological sample obtained from a patient diagnosed with HIV. In still other embodiments, the control is a historical control or standard reference value or range of values (such as a previously tested control sample, such as a group of HIV patients with known prognosis or outcome, or group of samples that represent baseline or normal values, such as the presence or absence of HIV in a biological sample.

In some embodiments, the results of an IPSA assay performed on a test sample using primer sets as described herein can be compared with a standard control (such as a standard curve) generated using an IPSA assay with the same primer sets that is performed on a mixture of target nucleic acid molecules comprising a pre-selected proportion of mutant and wildtype alleles to detect the presence (or proportion) of a particular allele in the test sample.

Ct (threshold cycle): The PCR cycle number at which the fluorescence emission (dRn) exceeds a chosen threshold, which is typically 10 times the standard deviation of the baseline (this threshold level can, however, be changed if desired). The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(1/slope)}$, for example. The efficiency of the PCR should be 90-100% meaning doubling of the amplicon at each cycle. This corresponds to a slope of −3.1 to −3.6 in the Ct vs. log-template amount standard curve.

Detecting: To identify the existence, presence, or fact of something. General methods of detecting are known to the skilled artisan and may be supplemented with the protocols and reagents disclosed herein. For example, included herein are methods of detecting an integrated virus (such as, for example, HIV) in a biological sample, including detecting a particular HIV allele in a biological sample, such as a drug resistant allele or the presence of integrated virus following anti-viral treatment to monitor the efficacy of said treatment. Detection can include a physical readout, such as fluorescence or a reaction output, or the results of PCR (such as qPCR) assay.

Detectable marker: A detectable molecule (also known as a label) that is conjugated directly or indirectly to a second molecule, such as a nucleic acid molecule, to facilitate detection of the second molecule. The person of ordinary skill in the art is familiar with detectable markers for labeling nucleic acid molecules and their use. For example, the detectable marker can be capable of detection by ELISA, spectrophotometry, flow cytometry, or microscopy. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with qPCR, such as multiplex qPCR. Various methods of labeling nucleic acid molecules are known in the art and may be used.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Human Immunodeficiency Virus (HIV): A retrovirus that causes immunosuppression in humans (HIV disease) and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

Isolated: An "isolated" biological component (such as a nucleic acid molecule or protein) has been substantially separated or purified away from other biological components in the cell of the organism in which the component naturally occurs. The term "isolated" does not require absolute purity. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Mismatch nucleotide: a nucleotide that is not complementary to the corresponding nucleotide of the opposite polynucleotide strand.

Multiplex qPCR: Amplification and detection of multiple nucleic acid species in a single qPCR reaction. By multiplexing, multiple target nucleic acids can be amplified in single tube. In some examples, multiplex PCR permits the simultaneous detection of the multiple HIV alleles, such as a drug-resistant allele and a non-drug resistant allele, or multiple drug resistant alleles.

Nucleic acid: A deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a probe or primer. In another particular example, a nucleic acid molecule is a double stranded (ds) nucleic acid, such as a target nucleic acid. Examples of modified nucleic acids are those with altered sugar moieties, such as a locked nucleic acid (LNA).

Nucleotide: The fundamental unit of nucleic acid molecules. A nucleotide includes a nitrogen-containing base attached to a pentose monosaccharide with one, two, or three phosphate groups attached by ester linkages to the saccharide moiety. The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, as known in the art. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine. Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences." Unless denoted otherwise, whenever a polynucleotide sequence is represented, it will be understood that the nucleotides are in 5' to 3' orientation from left to right.

Oligonucleotide probes and primers: A probe includes an isolated nucleic acid (usually of 100 or fewer nucleotide residues) attached to a detectable label or reporter molecule, which is used to detect a complementary target nucleic acid molecule by hybridization and detection of the label or reporter. Isolated oligonucleotide probes (which as defined herein also include the complementary sequence and corresponding RNA sequences) are of use for detection of HIV sequences. Typically, probes are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length. For example, a probe can be about 10-100 nucleotides in length, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50 or 25-80 nucleotides in length.

"Primers" are nucleic acid molecules, usually DNA oligonucleotides of about 10-50 nucleotides in length (longer lengths are also possible). "Primers" are a capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation. Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length.

"Probes" are molecules capable of interacting with a target nucleic acid, typically in a sequence specific manner, for example through hybridization. The hybridization of nucleic acids is well understood in the art and discussed herein. Typically, a probe can be made from any combination of nucleotides or nucleotide derivatives or analogs available in the art. Probes and primers can also be of a maximum length, for example no more than 15, 25, 25, 40, 50, 75 or 100 nucleotides in length.

Primers may be annealed to a complementary target DNA strand by nucleic acid hybridization to form a hybrid between the primer and the target DNA strand, and then extended along the target DNA strand by a DNA polymerase enzyme. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides. In some embodiments, probes and primers are used in combination in a qPCR reaction.

Plus Primer: An oligonucleotide primer for use in allele-specific PCR. A plus primer includes a locked nucleic acid at the 3' position that is complementary to a mutant allele of a target nucleic acid, and a mismatch nucleotide at the −1 position from the 3' end that is not complementary to the target nucleic acid molecule.

Primer pair: Two primers (one "forward" and one "reverse") that can be used for amplification of a nucleic acid sequence, for example by polymerase chain reaction (PCR) or other in vitro nucleic-acid amplification methods. The forward and reverse primers of a primer pair do not hybridize to overlapping complementary sequences on the target nucleic acid sequence.

Proof-Reading Polymerase: A polymerase enzyme with 3' to 5' exonuclease activity. A Non-limiting example of a proof-reading polymerase include Phusion DNA polymerase, Platinum SuperFi DNA Polymerase, Ranger Polymerase. Proof-reading polymerases with 3' to 5' exonuclease activity are known to the person of ordinary skill in the art and are commercially available, for example, from New England Biolabs, Ipswich, MA.

Real-Time PCR (qPCR): A method for detecting and measuring products generated during each cycle of a PCR, which are proportionate to the amount of template nucleic acid prior to the start of PCR. The information obtained, such as an amplification curve, can be used to determine the presence of a target nucleic acid (such as a HIV nucleic acid or polymorphism thereof) and/or quantitate the initial amounts of a target nucleic acid sequence. Exemplary procedures for qPCR can be found in "Quantitation of DNA/RNA Using Real-Time PCR Detection" published by Perkin Elmer Applied Biosystems (1999); PCR Protocols (Academic Press, New York, 1989); A-Z of Quantitative PCR, Bustin (ed.), International University Line, La Jolla, CA, 2004; and Quantitative Real-Time PCR in Applied Microbiology, Filion (Ed), Caister Academic Press, 2012.

In some examples, the amount of amplified target nucleic acid (for example a HIV nucleic acid) is detected using a labeled probe, such as a probe labeled with a fluorophore, for example a TAQMAN® probe. In other examples, the amount of amplified target nucleic acid (for example a HIV nucleic acid) is detected using a DNA intercalating dye. The increase in fluorescence emission is measured in real-time, during the course of the qPCR. This increase in fluorescence emission is directly related to the increase in target nucleic acid amplification. In some examples, the change in fluorescence (Delta Rn; dRn; ∆Rn) is calculated using the equation $dRn=Rn^+ - Rn^-$, with $Rn^+$ being the fluorescence emission of the product at each time point and $Rn^-$ being the fluorescence emission of the baseline. The dRn values are plotted against cycle number, resulting in amplification plots for each sample. The threshold cycle (Ct) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(1/slope)}$, for example. The efficiency of the PCR should be 90-100% meaning doubling of the amplicon at each cycle. This corresponds to a slope of −3.1 to −3.6 in the Ct vs. log-template amount standard curve.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sensitivity and specificity: Statistical measurements of the performance of a binary classification test. Sensitivity measures the proportion of actual positives which are correctly identified (e.g., the percentage of samples that are identified as including nucleic acid from a particular virus). Specificity measures the proportion of negatives which are correctly identified (e.g., the percentage of samples that are identified as not including nucleic acid from a particular virus).

Sequence identity: The similarity between two nucleic acid sequences is expressed in terms of the similarity between the sequences, otherwise referred to as sequence identity.

Sequence identity is frequently measured in terms of percentage identity, similarity, or homology; a higher percentage identity indicates a higher degree of sequence similarity. The NCBI Basic Local Alignment Search Tool (BLAST), Altschul et al, J. Mol. Biol. 215:403-10, 1990, is available from several sources, including the National Center for Biotechnology Information (NCBI, Bethesda, MD), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, Hybridization With Nucleic Acid Probes, Part I: Theory and Nucleic Acid Preparation, Laboratory Techniques in Biochemistry and Molecular Biology, Elsevier Science Ltd., 1993.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Subject: Any mammal, such as humans, non-human primates, pigs, sheep, horses, dogs, cats, cows, rodents and the like. In two non-limiting examples, a subject is a human subject or a murine subject. Thus, the term "subject" includes both human and veterinary subjects. An immunocompromised subject is a subject with a suppressed immune system, such as a subject with HIV.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. In some examples, a target nucleic acid includes a region of the HIV genome that includes an allele specific mutation that results in drug resistance. Purification or isolation of the target nucleic acid molecule, if needed, can be conducted by methods known to those in the art, such as by using a commercially available purification kit or the like.

Under conditions sufficient for: A phrase that is used to describe any environment that permits a desired activity. In one example the desired activity is amplification of a nucleic acid molecule.

Wild-type: The genotype or phenotype that is most prevalent in nature. The naturally occurring, non-mutated version of a nucleic acid sequence. Among multiple alleles, the allele with the greatest frequency within the population is usually the wild-type. The term "native" can be used as a synonym for "wild-type."

Throughout this application, various publications are referenced. The disclosures of these publications in their entireties are hereby incorporated by reference into this application in order to more fully describe the state of the art to which this pertains.

The references disclosed are also individually and specifically incorporated by reference herein for the material contained in them that is discussed in the sentence in which the reference is relied upon.

B. Integrated Proviral Sequencing Assay

Figure 1:
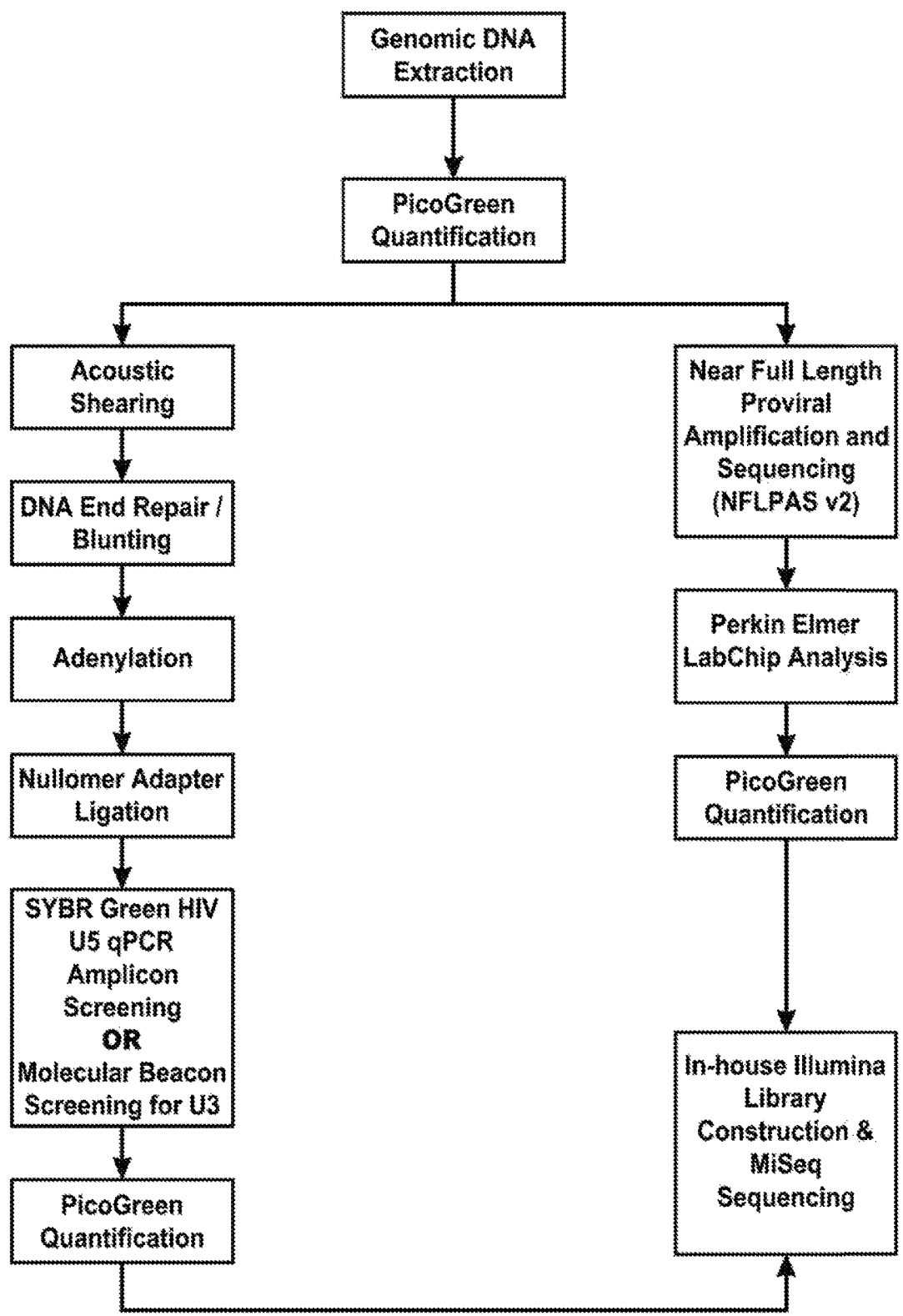
FIG. 1 shows a schematic of the Integrated Proviral Sequencing Assay.
Figures 1, 2:
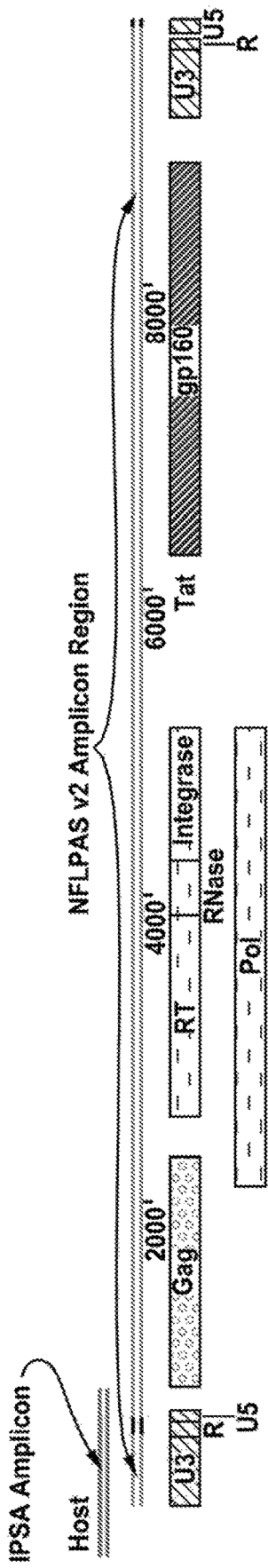
FIG. 2 shows a schematic of the 71-base pair, partially-double stranded DNA oligonucleotide comprising a 3'dT overhang and showing stem-loops formed by the adapter molecule.
Figure 2:
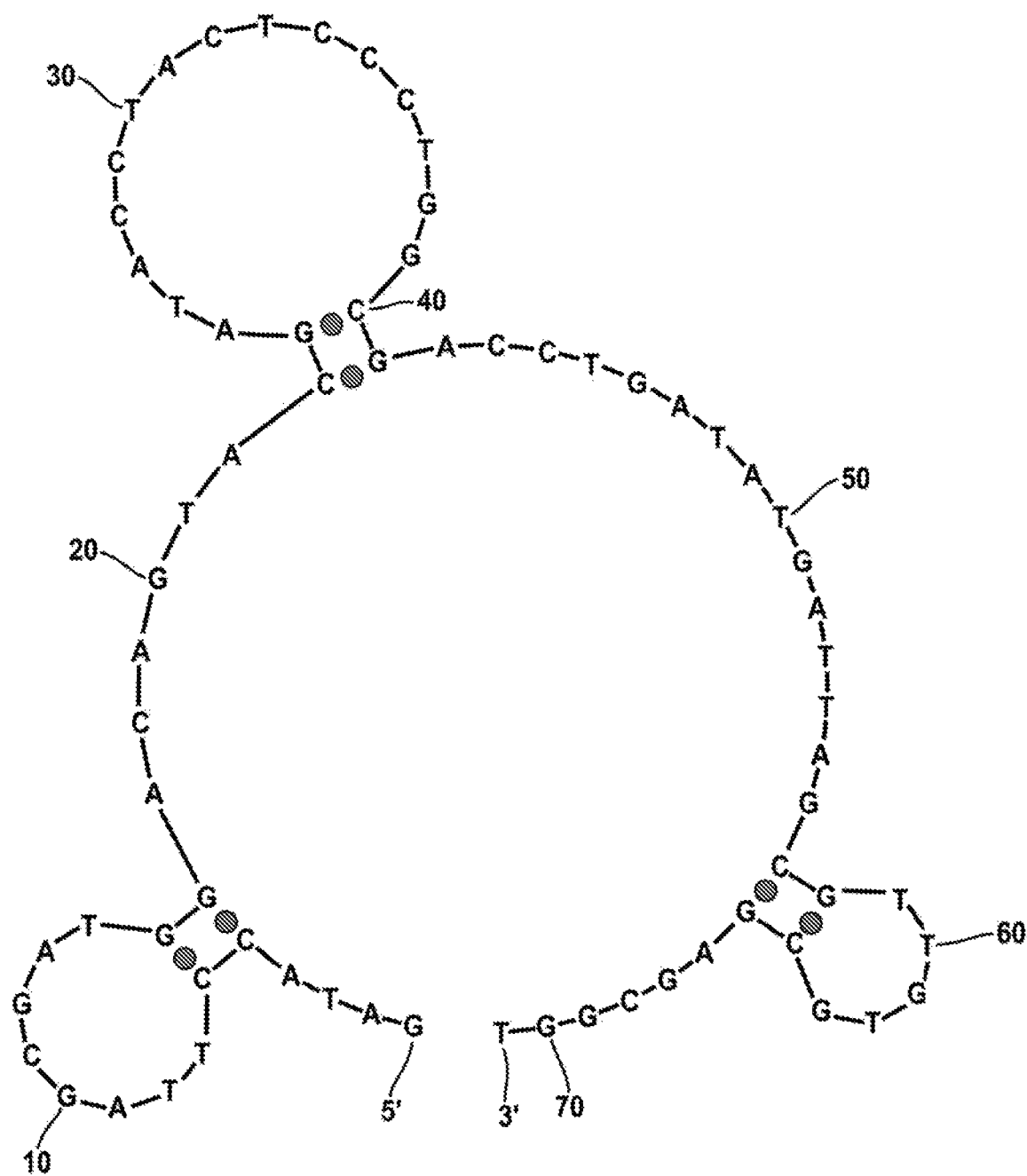

The Integrated Proviral Sequencing Assay (IPSA) is a significant technological advancement that allows rapid amplification and identification of rare sites in the human genome of integration of viruses such as retroviruses (for example human immunodeficiency virus type 1 or 2 (HIV-1 or 2), or other viral DNA genomes (hepatitis B virus or human herpes virus type 6), in diverse locations in the human genome. In addition to identifying the sites of viral integration, the entire viral genome can be amplified and sequenced. These amplifications are performed at proviral end point dilutions, allowing sequencing and detection of individual proviral species. IPSA has undergone extensive development and optimization overcoming short-comings of previous methods. Specifically, the DNA linker used in IPSA is comprised of a 71-base pair, partially-double stranded DNA oligo utilizing a 3' dT overhang for dA ligation. It contains a 15-base pair antisense strand with a 5' P and two terminal 3' C3 spacers on the antisense strand to prevent non-specific extension. This adapter molecule is shown in FIG. 2. Blocking of the 3' end of the truncated antisense strand allows linker primer site regeneration only when there is internal priming of the viral genome downstream of the linker. Accordingly, in one aspect, disclosed herein are synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40).

Figure 3:
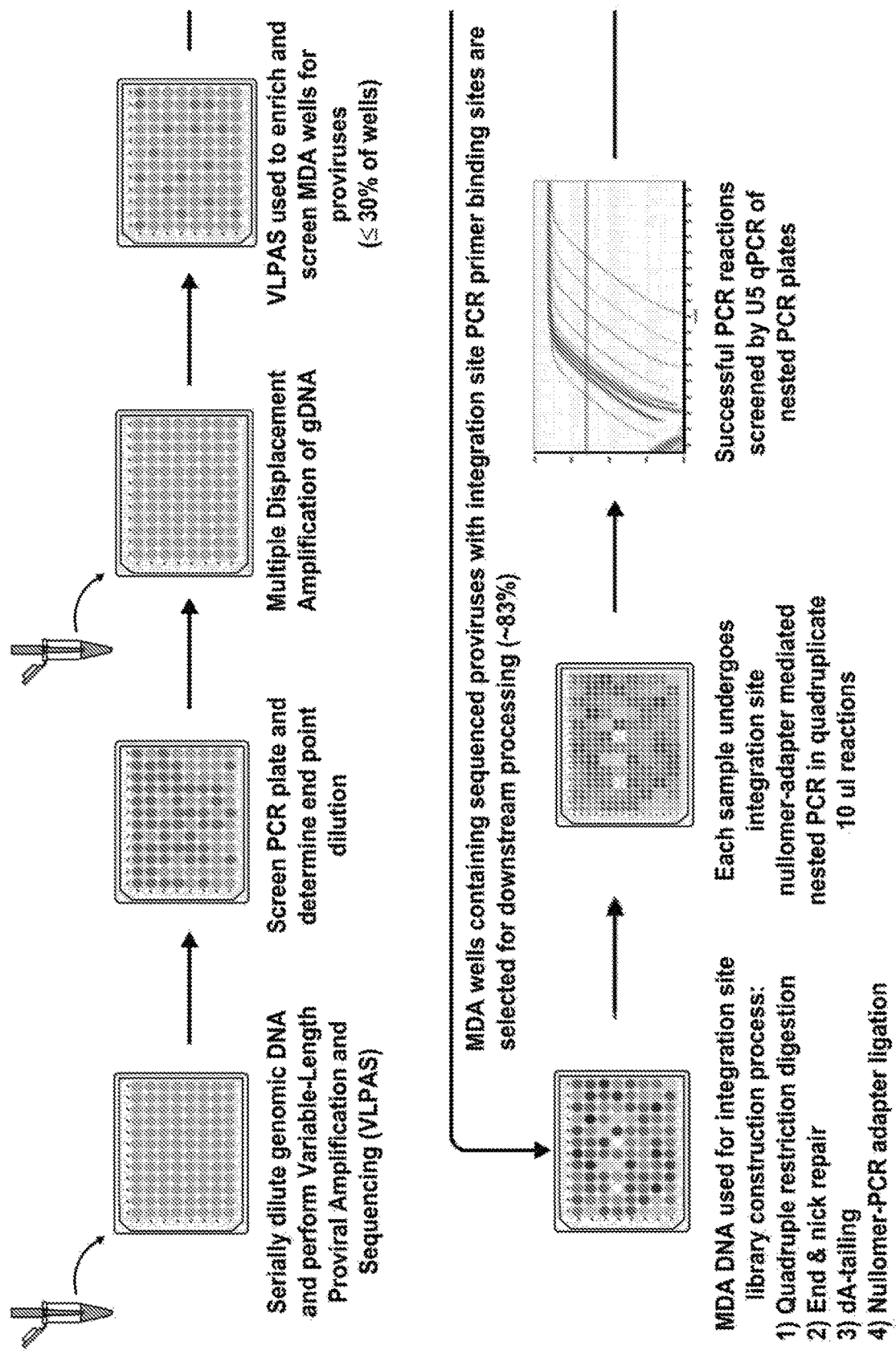
FIG. 3 shows schematic representation of an auxiliary workflow utilizing multiple displacement amplification (MDA), a subtype of WGA, for the methods of detecting integrated proviral DNA from a single end-point diluted genomic DNA aliquot.
Figure 3:
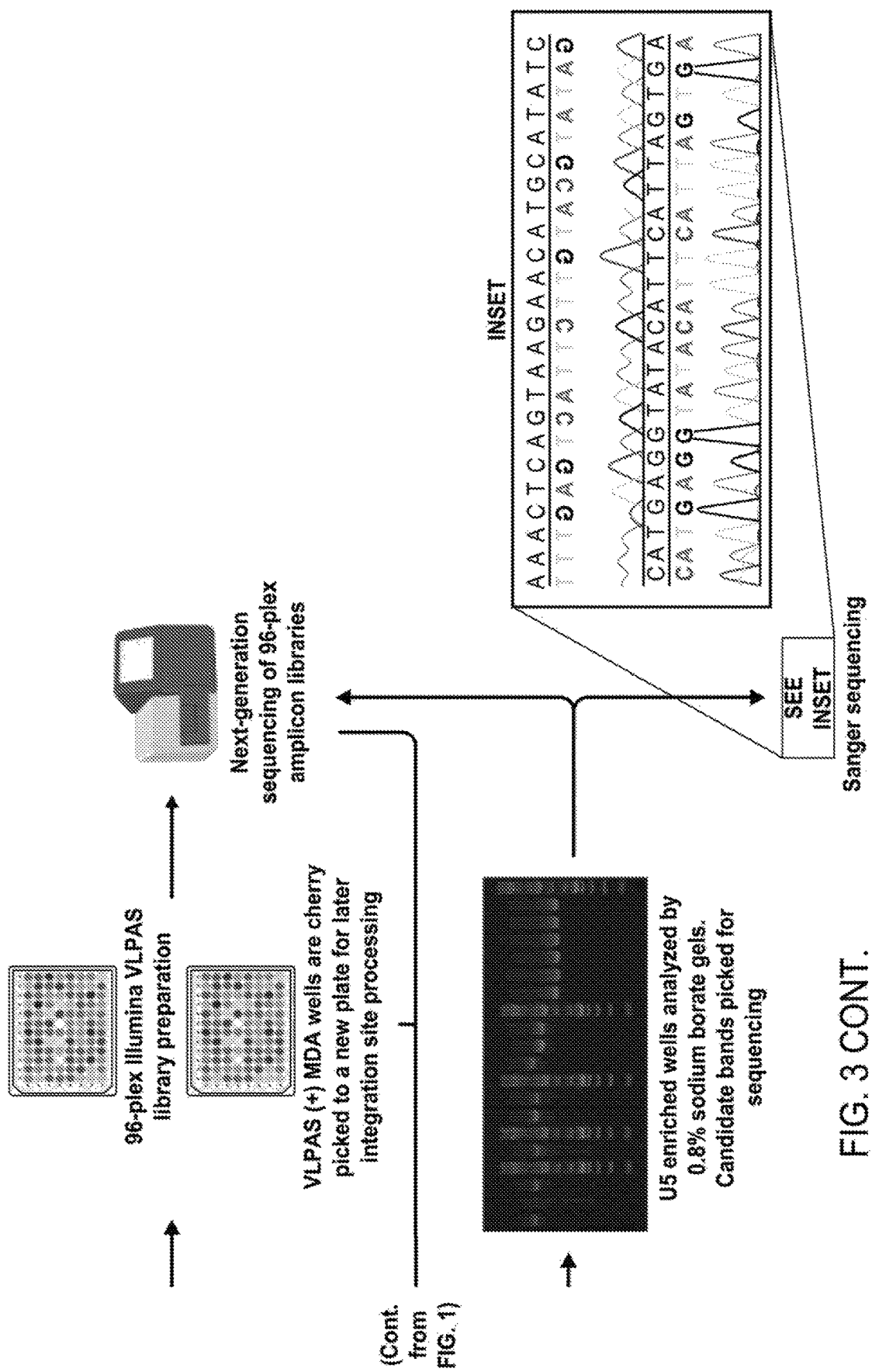

As noted above, the disclosed adapter molecules can be used to not only detect the presence of viral nucleic acid integrated into a host genome, but also identify the location of the integrated proviral nucleic acid within the genome. The final output of the IPSA is complete sequencing of integrated retroviruses or other integrated proviral genomes from the 5' to the 3' integration site along with any necessary flanking host sequences to pinpoint its location in the human genome (such as, for example, SEQ ID NOs: 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, and/or 109). Previously such rare integrations (around 1 provirus in 1000 human genomes or more in the case of HIV) have not been successfully amplified in a manner that provides both sufficient host and proviral DNA sequence to identify the integration and characterize the integrated provirus including whether it is intact (i.e., absence of insertions, deletions, stop codons or other lethal change) and its phylogenetic relationship to proviruses in other cells or other individuals. This new approach improves PCR specificity to between 1:1,000,000,000 and 1:3,200,000,000 when paired with nested PCR techniques and overcomes the barrier of non-specific PCR amplification of human DNA sequences without the desired target. Thus, greater sensitivity and specificity are achieved while enabling the ability to determine if the integrated sequence is function and where integration occurred. Accordingly, in one aspect disclosed herein are methods of detecting the presence and location of a viral nucleic acid integrated into the genome of a host comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; and b) sequencing and aligning (i.e., assembling) the amplicons generated by the first and second amplification reactions. This iteration of IPSA is shown in FIG. 1. In one aspect, it is understood and herein contemplated that by taking advantage of the power of whole genome amplification (WGA), the method can be made even more sensitive as the WGA can be used to amplify viral or proviral end-point diluted aliquots of the host genome thousands of times copying the integration site with it. For example, the method of detecting the presence and location of a viral nucleic acid integrated into the genome of a host can further comprise a method as shown in FIG. 3 Specifically, the method of detecting the presence and location of a viral nucleic acid integrated into the genome of a host can further comprise a) performing whole genome amplification (WGA) on a proviral end-point diluted genomic DNA fragment from the host; b) performing a nested near full length proviral amplification on the amplicons generated by the whole genome amplification reaction; c) construct a library of amplicons using the generated WGA DNA, from step a, which was identified to contain a provirus from step b; d) performing a viral specific nested PCR on library; and e) sequencing the amplicons of step b and step d. In one aspect, the method can further comprise screening the WGA reaction amplicons for proviruses before constructing a library of amplicons for integration site amplification. It is understood and herein contemplated that the viral specific nested PCR of step d can comprise ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer. While possible to perform WGA on a single copy of a host genome, the method often starts with between 70 and 350 human genome equivalents. Accordingly, disclosed herein are methods of detecting the presence and location of a viral nucleic acid integrated into the genome of a host comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; and b) sequencing and aligning (i.e., assembling) the amplicons generated by the first and second amplification reactions; said method further comprising a) performing whole genome amplification (WGA) on a proviral end-point diluted genomic DNA fragment from the host; b) performing a nested near full length proviral amplification on the amplicons generated by the whole genome amplification reaction; c) construct a library of amplicons using the generated WGA DNA, from step a, which was identified to contain a provirus from step b; d) performing a viral specific nested PCR on library; and e) sequencing the amplicons of step b and step d.

In addition, during IPSA development it became obvious that secondary structures within the retroviral long-terminal repeats (LTRs) reduced the efficiency of repair, ligation, and PCR amplification. Each step of constructing adapter-ligated IPSA samples has been optimized to alleviate issues caused by secondary LTR structures and to reduce PCR artifacts associated with such structures. For example, as noted above, to remove bias in captured integration sites, an acoustic shearing instrument can be used to obtain a tight distribution of DNA fragment sizes to improve PCR efficiency and to provide sufficient host/proviral sequence for analysis. Also, a second step for IPSA is parallel second amplification of the integrated proviral genome. The products of the first step (host virus junction) and the second step (viral genome) have sufficient sequence overlap such they can be aligned and assembled into a complete host virus-host sequence and a determination can be made as to whether the viral genome is intact (absence of insertions, deletions, stop codons or other inactivating mutations). The latter step is important because a large fraction of integrated retroviral or other viral genomes are not intact (defective) and thus are not a source of infectious virus that can cause relapse of the infection. Identifying the location of intact viral genomes in the human genome is critical to targeting their elimination or permanent silencing.

The sequencing and aligning of amplicons performed in the disclosed methods can be accomplished by any means known in the art including Maxam-Gilbert sequencing, Sanger sequencing as well as next generation sequencing (NGS) methods, including, but not limited to sequencing by synthesis, pyrosequencing, ion torrent sequencing, single-molecule real-time sequencing, sequencing by ligation, nanopore sequencing, combinatorial probe anchor synthesis.

It is understood and herein contemplated that the DNA fragments for the first amplification can be created by shearing genomic nucleic acid obtained from the host. Shearing can be accomplished by any means known in the art including, but not limited to enzymatic shearing, adaptive focused acoustic shearing, sonication, nebulization, chemical shearing, hydrodynamic shearing, point-sink shearing, and centrifugation. As used herein, "enzymatic shearing" refers to enzyme-based fragmentation of DNA by the simultaneous cleavage of both strands, or by generation of nicks on each strand of dsDNA to produce dsDNA breaks. Enzymes suitable for enzymatic shearing include, but are not limited to restriction enzymes, fragmentase, DNAse 1, T7 endonuclease 1, and transposase. "Adaptive Focused Acoustic shearing" methods refers to the use of short wavelength acoustic energy which focuses transmission of high-frequency acoustic energy on the DNA sample and can be performed isothermally. The transducer is bowl shaped so that waves converge at the target of interest. Sonication is another method of shearing which is distinguished from acoustic sharing by using specialized sonicators which subject DNA to longer wavelength, unfocused acoustic energy, and requires cooling periods between sonication bursts. Nebulization uses compressed air to force DNA through a small hole in a nebulizer unit, and the fragmented, aerosolized DNA is collected. DNA fragment size is determined by the pressure used. Hydrodynamic shearing, uses a syringe pump to create hydrodynamic shear forces by moving DNA through a tube with a tight constriction, such that the DNA breaks, with the size of the constriction and the flow rate of the liquid determining the DNA fragment size. As noted above, DNA can also be sheared by the use of centrifugal force to move DNA through a hole of a specific size. The rate of centrifugation determines the degree of DNA fragmentation. Similarly, needle shearing creates shearing forces by passing DNA through a small gauge needle. It is understood and herein contemplated that the shearing method selected can depend on the desired fragment size, fragment end shape (blunt ended, staggered, having a particular overhang, or following a particular nucleic acid) and uniformity as well as cost and time constraints, for example, adaptive focused acoustic shearing can generate fragment sizes from 150 base pairs (bp) to 5 kilo bp (kbp), the size of which can be controlled during the shearing and targeted to suit the sequencing method used. Accordingly, disclosed herein are methods of detecting the presence and location of a viral nucleic acid integrated into the genome of a host, wherein the genomic nucleic acid is sheared (such as, for example, shearing by adaptive focused acoustic shearing) prior to ligation of the adaptor molecule.

As noted above, the disclosed methods of detecting the presence and location of a viral nucleic acid integrated into the genome of a host comprise the use of the disclosed adaptor molecule comprising a synthetic 71-base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40). This adapter molecule which is used by IPSA (i.e., the methods of detecting an integrated virus in a host genome) further improves on partially double-stranded adapter design by incorporating 11 bp patterns that do not exist within the human genome. As a result, little to no off-target amplification occurs as a result of the PCR primers or linkers. This approach further improves specificity of the nested PCR step of the assay. The linker also includes 3 internal priming sites for subsequent rounds of nested PCR, and a dideoxy sequencing primer site to sequence the amplified material.

It is understood and herein contemplated that the disclosed methods of detecting the presence and location of an integrated proviral nucleic acid can be used to detect the presence and location of any virus that can integrate into the host genome including, but not limited to viruses of the family Retroviridae, Hepadnaviridae, and Herpesviridae. Thus, in one aspect, disclosed herein are methods of detecting the presence and location of an integrated proviral nucleic acid, wherein the viral nucleic acid is from a virus from the viral family Retroviridae (such as, for example, a lentivirus (including, but not limited to Human Immunodeficiency Virus, or deltaretrovirus), or Hepadnaviridae (such as, for example, a Hepatitis B virus), Herpesviridae (such as, for example, Herpes Simplex Virus-1, Herpes Simplex Virus-2, Varicella-zoster virus, Epstein-Barr virus, Cytomegalovirus, Human Herpes Virus 6A, Human Herpes Virus 6B, Human Herpes Virus 7, and Human Herpes Virus 8). It is further understood and herein contemplated that the disclosed methods of detecting viral or proviral DNA integrated into the host genome can be used to diagnose the host subject with a latent, viral infection. Thus, in one aspect, disclosed herein are methods of diagnosing a subject with a latent viral infection the method comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang as (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; and c) assembling any aligned integrated proviral sequence to a known full viral sequence; wherein the identification of a viral or proviral sequence absent any truncations, mutations, deletions, or additions in the viral genome indicates a latent viral infection.

Because the disclosed methods can diagnose a latent viral infection, such methods can comprise a key aspect to a treatment regimen that includes first detecting a latent viral infection and then treating the infection with a suitable antiviral. The decision how to treat a subject exposed to a virus that can integrate into the host genome, but otherwise presenting no symptoms of infection can be critical to the early treatment or management of the viral infection. Prior to the disclosed methods, detection of integrated virus was difficult at best, and even when viral DNA was detected, the methods could not distinguish integrated from unintegrated proviral genomes and the location of the integrated genome. Thus, the specific type of treatment related to the proviral integration site or targeting of specific integration sites to affect the persistence of HIV could not be accomplished. The disclosed methods can fill in this knowledge deficit. Thus, in one aspect disclosed herein are methods of treating a latent viral infection in a subject comprising detecting the presence of a viral or proviral nucleic acid integrated in the host genome said method comprising a) performing a first amplification reaction and a second amplification reaction on host genomic DNA; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39) and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; c) assembled any aligned integrated proviral sequence to a known full viral sequence; wherein the identification of a viral or proviral sequence absent any truncations, mutations, deletions, or additions in the viral genome indicates a latent viral infection; and d) treating the subject with a suitable antiviral for the detected infection. In some instances, the antiviral can target specific viral or proviral genomes in specific locations in the human genome.

As noted above, the disclosed methods not only provide for the detection of integrated proviral or proviral sequences in a host genome, but because the methods can detect the entire integrated sequences and its location, the methods provide for the ability to distinguish a non-functional integrated sequences (i.e., a partial or mutated sequence) from a functional sequence. Accordingly, in one aspect, disclosed herein are methods of detecting a functional or non-functional viral or proviral sequence integrated into the genome of a subject comprising performing any of the integrated proviral detection methods disclosed herein. Specifically, disclosed herein are methods of distinguishing a non-functional integrated sequences (i.e., a partial or mutated sequence) from a functional sequence comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; and c) assembling integrated proviral sequence to a known full viral sequence; wherein a sequence comprising truncations, mutations, deletions, or additions in the viral genome are not functional integrated viruses. Alternatively, the method of distinguishing a non-functional integrated sequences (i.e., a partial or mutated sequence) from a functional sequence can further comprise a) performing whole genome amplification (WGA) on a proviral end-point diluted genomic DNA aliquot from the host; b) performing a nested near full length proviral amplification on the amplicons generated by the whole genome amplification reaction; c) construct a library of amplicons using the generated WGA DNA, from step a, which was identified to contain a provirus from step b; d) performing a viral specific nested PCR on library; and e) sequencing the amplicons of step b and step d; and f) assembling any aligned integrated proviral sequence to a known full viral sequence; wherein a sequence comprising truncations, mutations, deletions, or additions in the viral genome are not functional integrated viruses.

It is understood and herein contemplated that the disclosed methods of detecting integrated virus can be used to determine the efficacy of an antiviral used to prevent, inhibit, or treat and infection with a virus that can integrate into the host genome (such as, for example, a virus from the viral family Retroviridae (such as, for example, a lentivirus (including, but not limited to Human Immunodeficiency Virus, or deltaretrovirus), or Hepadnaviridae (such as, for example, a Hepatitis B virus), Herpesviridae (such as, for example, Herpes Simplex Virus-1, Herpes Simplex Virus-2, Varicella-zoster virus, Epstein-Barr virus, Cytomegalovirus, Human Herpes Virus 6A, Human Herpes Virus 6B, Human Herpes Virus 7, and Human Herpes Virus 8). The detection of reduced or no functional integrated virus in the host genome would indicate that the antiviral treatment was efficacious. Thus, disclosed herein are methods of assaying the efficacy of an antiviral treatment, the method comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; and c) assembling any aligned integrated proviral sequence to a known full viral sequence; wherein a reduction in the amount of functional integrated virus or provirus relative to a control or absence of integrated virus or provirus indicates that the anti-viral was efficacious. In some aspects, it is understood and herein contemplated that the detection entire integrated proviral genome and integration site can be enhanced by using whole genome amplification in addition to the disclosed methods. Thus, in one aspect, disclosed herein are methods of assaying the efficacy of an antiviral treatment, the method comprising a) performing whole genome amplification (WGA) on a proviral end-point diluted genomic DNA aliquot from the host; b) performing a nested near full length proviral amplification on the amplicons generated by the whole genome amplification reaction; c) construct a library of amplicons using the generated WGA DNA, from step a, which was identified to contain a provirus from step b; d) performing a viral specific nested PCR on library; and e) sequencing the amplicons of step b and step d; and f) assembling any aligned integrated proviral sequence to a known full viral sequence; wherein a reduction in the amount of functional integrated virus or provirus relative to a control or absence of integrated virus or provirus indicates that the anti-viral was efficacious.

Because the disclosed methods of detecting identify the site of viral or proviral integration, the disclosed methods can be used to identify targets for antiviral therapies involving CRISPR-Cas9 to target viral and/or proviral regulatory genes and disrupt their activity. Accordingly, disclosed herein are methods of identifying targets for an antiviral therapy against a virus that integrates in a host genome, the method comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40); wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; wherein the sequencing alignment provides both the identification of functional integrated proviral or proviral DNA and the location of the integration in the host genome.

Also disclosed herein are kits that are drawn to reagents that can be used in practicing the methods disclosed herein. In one aspect disclosed herein are kits for detecting the presence of viral nucleic acid in an integrated into the genome of a host comprising a synthetic 71 base pair, partially-double stranded DNA oligonucleotide comprising a 3'dT overhang (such as for example, partially-double stranded DNA oligonucleotide comprising a 3'dT overhang as set forth in SEQ ID NO: 1 and/or SEQ ID NO: 39), and 15 base pair antisense strand with a 5'P and two terminal 3' C3 spacers on the antisense strand (such as, for example, a 15 base pair antisense strand with a 5'P and two terminal 3' C3 spacers on the antisense strand as set forth in SEQ ID NO: 2 and/or SEQ ID NO: 40). The kits can include any reagent or combination of reagent discussed herein or that would be understood to be required or beneficial in the practice of the disclosed methods. For example, the kits could include adapter specific primers and/or viral specific primers to perform the amplification reactions discussed in certain embodiments of the methods, as well as the buffers and enzymes required to use the primers as intended.

C. Examples

The following examples are put forth so as to provide those of ordinary skill in the art with a complete disclosure and description of how the compounds, compositions, articles, devices and/or methods claimed herein are made and evaluated and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: IPSA Library Construction

Samples from three donor (CA, TR, and RM) were obtained from individuals with integrated HIV infection.

a) Acoustic Shearing, Blunting, and dA Tailing

Samples were normalized to 5 ng/ul and 200 ul of sample was dispensed into a Clear miniTUBE. Place the miniTUBE in the water bath to chill for at least 5 minutes. Once water bath is cooled to 7 C, start the shearing protocol. After protocol completed, the sample was removed from the miniTUBE and dispensed into a well of a 96-well plate. 2 ul were sequestered for LabChip analysis later.

Once the mean fragment size of approximately 1.6 kb or less was attained, end repair and blunting was performed on the nucleic acid fragments using an end repair master mix comprising a polynucleotide kinase (such as T4 polynucleotide kinase (PNK), a ligase (such as, for example *E. coli* ligase), a DNA polymerase (such as, for example, T4 DNA polymerase), and a 3'-5' exonuclease. 25 ul of cold master mix were pipetted into the purified fragmented sample wells and mixed. Samples were incubated at 20 C for 20 minutes followed by ramping to 4 C for hold. Within 10 minutes, samples were ramped down and 2 ul of 0.5M EDTA was added to stop the reaction. Mix reaction volume thoroughly.

Samples were purified by performing a 1× solid phase reversible immobilization (SPRI) purification. To perform the SPRI purification, 52 ul of KAPA PureBeads or AmpureXP was added and mixed. Samples were incubated for 5 minutes, then the plate was placed on 96-well plate magnet for 2 minutes.

100 ul of supernatant was removed and discard from the sample wells. Next, 200 ul of 80% EtOH was added, incubated for 30 seconds. EtOH was then removed, and a second EtOH wash performed. EtOH was then removed and the plates dried. Samples were then removed from the magnet, and 30 ul of 5 mM Tris-HCl, pH 8.0 dispensed into the wells. Samples were resuspended thoroughly, ensuring the side of well has no beads left on it, before moving on to mix next column, placed on magnet, and incubated for 2 minutes.

To dA tail the fragmented samples, a master mix comprising Klenow (exonuclease minus) was added to the sample wells and incubated at 37 C for 30 minutes. The samples were ramped to 4 C and held.

b) Adapter Ligation.

6.2 ul of preannealed adapter with 5'P and 2 C3 spacers was added into the sample wells and mixed thoroughly. Next 20 ul of master mix was transferred into the samples wells and incubated in a thermocycler at 20 C for 4 hrs, followed by 16 C incubation overnight. After ligation, a 0.6×SPRI purification was performed, including two EtOH washes as above, and samples eluted in 100 ul of 5 mM Tris-HCl, pH 8.0.

2. Example 2: Adapter-Mediated PCR

To perform PCR on the samples, a PCR master mixed was created as set forth in Table 1 comprising primers to the adapter and to the HIV provirus (such as, for example forward primers SEQ ID NO: 3 (Adapter outer forward primer) and SEQ ID NO: 4 (Adapter middle forward primer) and reverse primers 892 (SEQ ID NO: 7) and 688 (SEQ ID NO: 8)). 8 ul of the PCR master mix was combined with 2 ul of diluted library and PCR performed. The PCR master mix comprised

TABLE 1

PCR Master mix

| Reagent | Final Concentration | Vol. per reaction (uL) |
|---|---|---|
| Molecular-grade water | | 2.4 |
| 5x SuperFi Buffer | 1x | 2 |
| dNTP (10 mM) | 200 nM | 0.2 |
| PCR 1: Nullomer Outer primer (10 uM) | 250 nM | 0.25 |
| PCR 2: Nullomer Inner primer (10 uM) | | |
| PCR 1: HIV Outer primer (10 uM) | 250 nM | 0.25 |
| PCR 2: HIV Inner primer (10 uM) | | |
| Bovine Thrombin (1 mg/mL) | 84 ug/mL | 0.84 |
| Betaine (5M) | 0.9M | 1.8 |
| ET SSB (500 ng/uL) | 8 ng/uL | 0.16 |
| Platinum SuperFi DNA Polymerase (2 U/uL) | 0.02 U/uL | 0.1 |
| | Total Volume (uL): | 10 |
| | Mastermix per reaction (uL): | 8 |

PCR I was performed by incubating at 95 C for 2 min, followed by 98 C for 10 s, ramping to 66.5 C for 120 s, and repeating for 39 cycles. After PCR I, samples are ramped down to 66.5 C for 240 s and held at 10 C where they were diluted 1:9. PCR II was performed the same as PCR I. Following PCR II, reactions were diluted 1:5 and screened for positive HIV containing amplicons. To perform screening of the samples a KAPA SYBR qPCR master mix was created as shown in Table 2. Samples were combined with the master mix at a final dilution of 1:1500 and qPCR run.

TABLE 2

KAPA SYBR qPCR master mix

| | 1 rxn | 9 rxn | 1/2 plate | 1 plate | 2 plate | 3 plate | 4 plate | 8 plate |
|---|---|---|---|---|---|---|---|---|
| 2x KAPA qPCR mix | 5 | 45 | 262.5 | 525 | 1050 | 1600 | 2100 | 4000 |
| SubB 522+ Forward Primer (SEQ ID NO: 13) (50 uM) | 0.05 | 0.45 | 2.625 | 5.25 | 10.5 | 16 | 21 | 40 |
| SubB 616− Reverse Primer (SEQ ID NO: 14) (50 uM) | 0.05 | 0.45 | 2.625 | 5.25 | 10.5 | 16 | 21 | 40 |
| H2O | 2.9 | 26.1 | 152.25 | 304.5 | 609 | 928 | 1218 | 2320 |
| Total Vol | 10 | 72 | 420 | 840 | 1680 | 3360 | 6720 | 13440 | qPCR was performed by incubating at 95 C for 3 min, followed by 95 C for 15 s, ramping to 57 C for 20 s, and ramping again to 72 C for 10 s for the fluorescence to be read and then repeating for 24 cycles. Following the qPCR, enriched PCR wells (qPCR Ct<16) were analyzed on agarose gel or LabChip 12K chip. 1×SPRI purification (45 ul of SPRI), bind 5 minutes, 2×200 ul 80% EtOH wash, dry 3.5 minutes, elute in 30 ul of 5 mM Tris-HCl, pH 8.0, was performed. Typically, gKISA amplicons perform well with 35-40 ng/reaction at GeneWiz for Sanger Sequencing using the HIV LTR primers 623−, 522+, 107+, and 90− sequencing or in Illumina MiSeq sequencing.

3. Example 3: Near Full Length Viral Amplification and Sequencing

Concurrently with the adapter-mediated PCR, a Near-Full Length Viral Amplification and Sequencing (NFL-PAS) nested PCR was run on the biological samples from subject CA, RM, and TR. Genomic DNA samples from each subject were combined with the nested PCR reaction mix as indicated in Table 3 which show the master mix for each of PCR 1 and PCR II reactions which differ only by the primers being used.

TABLE 3

NFL-PAS PCR master mix

| Reagent | 1 Plates | 2 Plates | 3 Plates | 4 Plates |
|---|---|---|---|---|
| 2x Ranger Mix | 500 ul | 1000 ul | 1500 ul | 2000 ul |
| Nuclease Free Water | 220 ul | 440 ul | 660 ul | 880 ul |
| 10 uM Forward Primer (NFL_OuterF_Phu (SEQ ID NO: 9) for PCR I, NFL_InnerF_Phu (SEQ ID NO: 11) for PCR II) | 40 ul | 80 ul | 120 ul | 160 ul |
| 10 uM Reverse Primer (NFL_OuterR_Phu (SEQ ID NO: 10) for PCR I, NFL_InnerR_Phu (SEQ ID NO: 12) for PCR II) | 40 ul | 80 ul | 120 ul | 160 ul |

PCR reaction I was run, followed by a 1:9 dilution before seeding PCR II. For each PCR reaction, PCR was performed by incubating at 95 C for 3 min, followed by 98 C for 10 s, ramping to 57 C for 10 min, and repeating the 10 s incubation at 98 C and the 10 min at 57 C for 29 cycles. Before ramp down a 10 C hold, a final extension for 10 min at 57 C was performed.

At this point, the amplicons from gKISA and NFL-PAS were then sequenced using Illumina library construction and MiSeq sequencing

4. Example 4: Illumina Library Construction a) Pre-Flight PicoGreen

Depending on the degree of need to conserve input DNA, you can perform PicoGreen in duplicate with 1 ul or 2 ul of sample per replicate. When using 1 ul replicates, dispense 99 ul of 1×TE buffer into each well of a black 96-well Costar plate where sample will be quantified. Final dilution factor for downstream concentration calculation is 1:100. When using 2 ul replicates, dispense 98 ul of 1×TE buffer into each well of the black 96-well Costar plate where sample will be quantified. Final dilution factor for downstream concentration calculation is 1:50.

To quantify the DNA, dispense 50 ul of 1×TE buffer into standard wells and 100 ul of 1×TE Buffer into plate blank wells. Thoroughly mix the samples if they were not recently solid phase reversible immobilization (SPRI) purified, and spin them down >1,000 RCF for <30 secs. 1 or 2 ul of sample is dispensed into each sample well carefully with a multichannel and mixed before blowing out remaining liquid.

Calculate the amount of PicoGreen Needed by first determining the total volume as follows:

Total Volume: # of standards+plate blanks [18 total]+[number of samples×2]+dead volume [5]×100.

Next, divide the total volume by 200 to find the 200× Pico Reagent needed.

Dilute the calculated amount of Picogreen stock into calculated Total Volume amount of 1×TE buffer. Dispense 100 ul of working solution in each well to be assayed and pipette mix.

5. Example 5: DNA Shearing a) Enzymatic Shearing 2 ul of 10×dsDNA Fragmentase buffer was dispensed into each sample (18 ul total volume), and allowed to chill on ice. Then 2 ul of dsDNA Fragmentase was added carefully and thoroughly mixed. Start the thermal appropriate cycler protocol for your sample and allow to cool to 0° C. Samples spun briefly in plate spinner (<10 sec total).

NFLPAS fragmentation protocol (9-10 kb) incubate samples at 37° C. for 16 minutes and immediately place on freezing cold ice block & add 5 ul of 0.5M EDTA. Mix reaction well.

Medium-sized amplicon Fragmentation protocol (4 kb-6 kb): incubate at 37° C. for 8 minutes and immediately place on freezing cold ice block & add 5 ul of 0.5M EDTA. Mix reaction well.

KISA Protocol (800 bp to 1.5 kb): incubate samples at 37° C. for 3.5 minutes and immediately place on freezing cold ice block & add 5 ul of 0.5M EDTA. Mix reaction well. Once the nucleic acid has been shorn, perform a 1×SPRI purification.

b) Focused Acoustic Shearing

After normalizing the samples to 15 ng/ul, carefully dispense 200 ul of sample into a Clear miniTUBE. Place the first miniTUBE in the water bath to chill for at least 5 minutes. Once water bath is cooled to 7 C, start the appropriate protocol. After protocol completes, carefully remove the sample from the miniTUBE and dispense across a column of a 96-well plate (25 ul per column). The last well will be a bit short, just dilute up to 25 ul with 5 mM Tris-HCl, pH 8. Once fragment size is 1.6 kb or less move to end repair.

6. Example 6: End Repair/Blunting

Prepare a master mix comprising a polynucleotide kinase (such as T4 polynucleotide kinase (PNK), a ligase (such as, for example *E. coli* ligase), a DNA polymerase (such as, for example, T4 DNA polymerase), and a 3'-5' exonuclease (such as, for example, large Klenow fragment) on ice, such as exemplified in Table 1 and mix thoroughly.

Dispense 25 ul of cold master mix into the purified fragmented sample wells and mix. Place on the thermal cycler and incubate at 20 C for 30 minutes. Ramp to 12 C for hold. Within 10 minutes, spike 2 ul of 0.5M EDTA to stop the reaction. Mix reaction volume thoroughly. Perform a 1×SPRI purification. Following purification, add an adenosine to the 3' end of the sense and anti-sense strands of the blunt ended fragments (i.e., dA Tailing).

7. Example 7: Adapter Ligation

To ligate the adapters for the TruSeq Dual Indexed Illumina adapter ligation, a buffer master mix was prepared comprising a DNA ligase (such as, for example, T4 DNA ligase) on ice without TruSeq Dual Indexed Illumina adapter (P5 as set for the in SEQ ID NO: 17 and P7 as set forth in SEQ ID NO: 18). 5 ul of adapters were added to the DNA, and mixed, followed by addition of 20 ul of mastermix. Reaction was mixed thoroughly.

Place on the thermal cycler and Incubate at 16 C for 30 minutes. Ramp to 4 C for hold. After ligation, perform a 0.8×SPRI purification followed by a two-sided SPRI Size Selection.

8. Example 8: Post Library Construction PCR

Following library construction, PCR was performed on the library using the Illumina P5 and P7 primers, (SEQ ID NOs: 15 and 16, respectively).

TABLE 4

| Post Library Construction master mix | | | | | |
|---|---|---|---|---|---|
| | 1 rxn | 9 rxn | 18 rxn | 50 rxn | 105 rxn |
| 5x Buffer | 10 | 90 | 180 | 500 | 1050 |
| dNTP (10 mM) | 1 | 9 | 18 | 50 | 105 |
| P5 Primer (SEQ ID NO: 15) (10 uM) | 1.25 | 11.25 | 22.5 | 62.5 | 131.25 |
| P7 Primer (SEQ ID NO: 16) (10 uM) | 1.25 | 11.25 | 22.5 | 62.5 | 131.25 |
| H2O | 6 | 54 | 108 | 300 | 630 |
| Platinum SuperFi DNA Polymerase | 0.5 | 4.5 | 9 | 25 | 52.5 |

Add 20 ul of PCR master mix to adapter ligated, purified libraries.

PCR master mix was dispensed into each adapter ligated, purified library. Samples were then placed on a thermal cycler and run Post-LC 12×PCR which comprised heating the samples to 95 C for 3 min, ramping to 98 C for 15 s, ramping to 65 C for 20 s, and ramping again to 72 C for 30 s. The cycle is then repeated an additional 11 times after which 1×SPRI purification was performed followed by POST library construction bioanalysis and sequencing on a MiSeq sequencer.

9. Example 9: Results

FIGS. 4 and 5 show sequencing alignment following Illumina sequencing for sample 1 and FIGS. 6 and 7 show sequencing alignment following Illumina sequencing for sample 2, each sample from subject CA. Results were displayed for the near-full length proviral amplicon consensus sequence (as generated by BWA-MEM using MiSeq data) and the overlapping integration site containing amplicon (with the host still attached) (FIGS. 4 and 5). The data demonstrates the capture of the full-length integrated provirus (integration site, all of 5'LTR, and most of 3' LTR U5 (which is covered by 5'LTR U5 sequence). Additionally, a paired end set of FASTQ files were generated for the second sample from the MiSeq during sequencing of the near-full length proviral amplicon (FIGS. 6 and 7). The CA_NFL_#.TXT file pertains to the near-full length proviral consensus amplicon sequence, and the other .TXT file (CA_gKISA . . . .TXT) is the integration site containing proviral Sanger sequence consensus, but with the integration site trimmed off for ease of alignment and proviral sequence matching purposes.

10. Example 10: PCR Duplex Oligonucleotide Adapter Annealing

A tabletop heat block should be pre-heated to 95° C. Each strand of the duplex oligo should be resuspended to 100 uM with 10 mM Tris-HCl, 1 mM EDTA, and 50 mM NaCl, pH 8.0. Each strand should be mixed at a 1:1 ratio in a microcentrifuge tube, and denatured for 5 minutes on the block. After 5 minutes, the heat block should be turned off but the oligo tube allowed to cool to room temperature gradually while remaining in the heat block.

11. Example 11: Hg19 Specific antiHIV Random Decamer Primer Preparation

The hg19_specific random decamer oligos were synthesized at IDT by their custom oligo team with desalted purity and were pooled equimolar post-synthesis. Oligos were received lyophilized and resuspended in 5 mM Tris-HCl, pH 8.0, aliquoted into 500 uL tubes, and frozen at −20° C.

12. Example 12: DNA Extraction TIMING: ~4 Hours

Thaw cryo-preserved cells on ice and dilute $1.25 \times 10^6$ cells up to 750 uL in cold RPMI (no phenol red). Invert tube to mix. Cells are pelleted by centrifugation at 500×g for 15 mins at 4° C. Remove supernatant with a transfer pipette carefully and discard in 10% bleach. Add 600 uL of Viral Lysis Buffer to cell pellet and then vortex for 3-4 seconds Pulse spin sample tube to collect liquid at the bottom and incubate for 10 minutes at room temperature. Add 600 uL of room temperature 100% isopropanol to the sample tube. Invert tube 30 times to mix. Centrifuged at 21,100×g for 20 mins at 10° C. Remove supernatant from the sample tube with a transfer pipette without disturbing DNA pellet. Add 1 mL of 70% ice cold ethanol to the sample and mix by inversion 30 times. Centrifuged at 21,100×g for 20 mins at 10° C. Remove supernatant from the sample tube with a transfer pipette without disturbing the DNA pellet. Repeat ethanol wash twice more. After the third ethanol wash supernatant is removed, centrifuge sample tube again at 21,100×g for 5 mins at 10° C. Remove supernatant with a 200 uL micropipette or equivalent without disturbing DNA pellet. Sample tube is spun once more at 21,100×g for 1 min at 10° C. Remove residual ethanol with a 20 uL micropipette. The DNA pellet is air dried for 15 mins at room temperature, during which the pellet may change from white to a more translucent white. Add 200 uL of ice cold 5 mM Tris-HCl, pH 8.0, to the tube and incubate without mixing for ≥5 mins. Carefully pipette mix the sample until the DNA pellet is thoroughly resuspended.

13. Example 13: Determination of Proviral End Point Dilution for Extracted Genomic DNA—TIMING: ~12 Hours (5.5 hr PCR1, Overnight PCR2)

In the clean room, prepare the PCR1 and PCR2 VLPAS mastermix according to Table 5, adding reagents in the order shown.

TABLE 5

| VLPAS mastermix. | | |
| --- | --- | --- |
| Reagent | Final Concentration | Volume per reaction (uL) |
| Molecular-grade water | | 4.2 |
| 2x Ranger master mix | 1X | 5 |
| PCR1: VLPAS Outer FWD primer (10 uM) | 400 nM | 0.4 |
| PCR2: VLPAS Inner FWD primer (10 uM) | | |

TABLE 5-continued

| VLPAS mastermix. | | |
| --- | --- | --- |
| Reagent | Final Concentration | Volume per reaction (uL) |
| PCR1: VLPAS Outer REV primer (10 uM) | 400 nM | 0.4 |
| PCR2: VLPAS Inner REV primer (10 uM) | | |
| Total Volume (uL): | | 10 |
| Mastermix per reaction (uL): | | 8 |

Dispense 8 uL of PCR mastermixes into each well of respective 96-well PCR 1 and 2 plates. Dispense 2 uL of molecular-grade water into plate wells C12 and D12 as no-template PCR controls. Transfer the mastermix plates into the PCR amplification room and keep at 4° C. until use. Within a dead air hood (when possible), serially dilute gDNA across adjacent wells of a PCR strip tube as follows using 5 mM Tris-HCl, pH 8.0 as a diluent: 4.3 uL of gDNA is mixed thoroughly in 34.7 uL of diluent (1:9), then 13 uL of 1:9 gDNA is mixed thoroughly in 26 ul of diluent (1:27). This is repeated twice more for a final dilution of 1:243 (or more if necessary for specific samples). Using a multichannel pipette, dispense 2 ul of diluted gDNA across all columns of the prepared PCR 1 mastermix plate (except for NTC wells C12 and D12). Centrifuge at 1,000×g for 1 minute at room temperature. Place the plate on a thermal cycler and run the following program: 1) 95° C. for 3 mins, 2) 98° C. for 10 secs, 3) 57° C. for 10 mins, 4) Steps 2-3 repeated 29×, 5) 57° C. for 10 mins, 10° C. hold. Centrifuge at 1,000×g for 1 minute at room temperature. Dilute the PCR1 plate wells with 80 uL of room temperature 5 mM Tris-HCl, pH 8.0. Mix by pipetting. Transfer 2 uL of the diluted PCR 1 plate to respective wells of the PCR 2 mastermix plate. Centrifuged at 1,000×g for 1 minute at room temperature, and placed on a thermal cycler using the following protocol: 1) 95° C. for 3 mins, 2) 98° C. for 10 secs, 3) 57° C. for 10 mins, 4) Steps 2-3 repeated 29×, 5) 57° C. for 10 mins, 10° C. hold. Centrifuged at 1,000×g for 1 minute at room temperature. Dilute the PCR2 plate wells with 40 uL of room temperature 5 mM Tris-HCl, pH 8.0. Mix by pipetting. Dilute gel red nucleic acid stain to 1× with 5 mM Tris-HCl, pH 8.0, and dispense 15 uL of the 1× solution into each well of the top half of a 96-well PCR plate. Add 5 uL of the diluted PCR 2 wells into the respective wells of the gel red plate. Place the plate on a transluminator and visualize under 300 nm UV light. The corresponding row in which ~30% of PCR reactions glow red is determined to be the proviral end point dilution. For new donors or unfamiliar samples, it is recommended to visualize the end point PCR products by 0.8% sodium borate agarose gel for 15-30 minutes at 250V, or an equivalent DNA analysis method.

14. Example 14: Multiple Displacement Amplification (MDA)—TIMING: 21 hrs (Overnight)

Prior to beginning, the following solutions are made and frozen for future use at −20° C.: Denature stock: 1.5M KOH, 37.5 mM EDTA, in molecular-grade water; Neutralization stock: 0.6M Tris-HCl (pH 7.5), 0.4M HCl, in molecular-grade water. (Stable for 6 months); Trehalose stock: 1.5M trehalose in molecular-grade water. (Stable for 6 months, may require heating at 60° C. during preparation); and 10×Phi29 buffer: 100 mM Tris-HCl, pH 7.5, 100 mM MgCl$_2$, 100 mM (NH$_4$)$_2$SO$_4$, 40 mM DTT, in molecular-grade water. In a clean room, prepare the denature and neutralization working solutions, and Phi29 mastermix according to Table 6, adding reagents in the order shown.

TABLE 6

MDA mastermix

Denature Working Solution

| Reagent | Final Concentration | Vol. per reaction (uL) |
|---|---|---|
| Denature stock | 400 mM | 0.53 |
| Molecular-grade water | — | 1.47 |
| Total Volume per reaction (uL): | | 2 |

Neutralization Working Solution

| Reagent | Final Concentration | Vol. per reaction (uL) |
|---|---|---|
| Neutralization stock | — | 1 |
| Trehalose stock | 250 mM | 1 |
| Total Volume per reaction (uL): | | 2 |

Phi29 Mastermix

| Reagent | Final Concentration | Vol. per reaction (uL) |
|---|---|---|
| Molecular-grade water | | 4.33 |
| 10X Phi29 Buffer | 1X | 2.5 |
| DTT (1M) | 6 mM | 0.05 |
| BSA (20 mg/mL) | 100 ng/uL | 0.13 |
| dNTPs ( 100 mM) | 3 mM | 0.75 |
| Trehalose (1.5M) | 600 mM | 9.00 |
| Random nonanner primer (1 mM) | 20 uM | 0.50 |
| Hg19_antiHIV_random decanner primers (1 mM) | 40 uM | 1.00 |
| Phi29 polymerase | 0.3 U/uL | 0.75 |
| Total Volume (uL): | | 25 |
| Mastermix per reaction (uL): | | 19 |

Dispense D-solution, N-solution, and phi29 mastermix across PCR strip tubes to aid in downstream reagent transfer. Dilute extracted gDNA with limited freeze thaws to the determined proviral end point to a final volume of 210 uL, using a minimum of 4 uL of gDNA stock sample and molecular-grade water as the diluent. Using a multichannel pipette for the following steps, reverse pipette 2 uL of gDNA to each well of a new 96-well plate (water used for wells G12 and H12 as MDA NTC). Dispense 2 uL of D-solution into each sample well without mixing. After all wells receive D-solution, seal the plate tightly and plate vortex it on medium for 10 seconds. Then centrifuge the plate for 1 minute at 1,000×g at room temperature. Incubate for 2 minutes and 50 seconds at room temperature, after which the plate is unsealed and placed on a 96-well ice-cold block. Dispense 2 uL of N-solution into each sample well without mixing. After all wells receive N-solution, seal the plate tightly and plate vortex it on medium for 10 seconds. Then centrifuge the plate for 1 minute at 1,000×g at room temperature. Incubate the plate on the cold block for 60 seconds, after which 19 uL of Phi29 mastermix is transferred to each well of the sample plate without mixing. Seal the sample plate tightly and mix thoroughly but gently by vigorous plate inversion. The phi29 mastermix is viscous and so proper mixing is critical. Centrifuge at 1,000×g for 1 min at room temperature, and placed on a thermal cycler using the following protocol: 1) 40° C. for 20 hours, 2) 65° C. for 10 mins, 3) 10° C. hold. After protocol completion, centrifuge at 1,000×g for 1 min at room temperature, and either stored at 4° C. short-term or stored at −20° C. long-term.

15. Example 15: Post MDA Purification—TIMING: 30 Mins

Warm KAPA Pure Beads up to room temperature before use and then mix thoroughly by vortexing for ≥30 secs._Dispense 20 uL of KAPA Pure Beads into the MDA sample plate and mix thoroughly by pipetting. Incubate for DNA binding for 5 mins at room temperature. Place plate on a 96-well side magnet for 2 mins, and then carefully remove the supernatant. Add 100 uL of fresh 80% ethanol into each well of the MDA plate and incubate on the magnet for ≥30 secs. Carefully remove the ethanol and discard. Ensure all ethanol is removed and air dry for ~1 min. Remove plate from the magnet and add 40 uL of 5 mM Tris-HCl (pH 8.0) to each well and pipette mix thoroughly. Incubate the plate at 37° C. for 5 mins for DNA elution. Place the plate on the magnet for 2 mins, and transfer the supernatant (pure DNA) to a clean 96-well PCR plate. The purified MDA DNA can be stored long term at −20° C. but care should be taken not to excessively freeze thaw it.

16. Example 16: Screening of Purified MDA Wells for HIV Proviruses (Variable Length Proviral Amplification and Sequencing, VLPAS)—TIMING: 12 Hrs (5.5 hr PCR1, Overnight PCR2)

In the clean room, prepare the PCR1 and PCR2 VLPAS mastermix according to Table 5, adding reagents in the order shown. Dispense 8 uL of PCR mastermixes into each well of respective 96-well PCR 1 and 2 plates. Dispense 2 uL of molecular-grade water into well H12 of the PCR plate as a PCR NTC. Transfer the mastermix plates into the PCR amplification room and keep at 4° C. until use. Dilute 2 ul of each MDA well with 8 ul of room temperature 5 mM Tris-HCl, pH 8.0, pipette mix, and transfer 2 ul to respective wells of the PCR 1 mastermix plate. Centrifuge at 1,000×g for 1 minute at room temperature, and placed on a thermal cycler using the following protocol: 1) 95° C. for 3 mins, 2) 98° C. for 10 secs, 3) 57° C. for 10 mins, 4) Steps 2-3 repeated 29×, 5) 57° C. for 10 mins, 10° C. hold. Centrifuge at 1,000×g for 1 minute at room temperature. Dilute each well of the PCR 1 plate with 80 uL of room temperature 5 mM Tris-HCl, pH 8.0 and pipette mix. Transfer 2 uL of the diluted PCR 1 plate to respective wells of the PCR 2 mastermix plate. Centrifuge at 1,000×g for 1 minute at room temperature, and place on a thermal cycler using the following protocol: 1) 95° C. for 3 mins, 2) 98° C. for 10 secs, 3) 57° C. for 10 mins, 4) Steps 2-3 repeated 29×, 5) 57° C. for 10 mins, 10° C. hold. Centrifuge at 1,000×g for 1 minute at room temperature. Dilute each well of the PCR 2 plate with 40 uL of room temperature 5 mM Tris-HCl, pH 8.0 and pipette mix. Dilute Gel red nucleic acid stain to 1× with 5 mM Tris-HCl, pH 8.0, and dispense 15 uL of the 1× solution into each well of a 96-well PCR plate. Transfer 5 uL of the diluted PCR 2 wells into the respective wells of the gel red plate. Place the plate on a transluminator and visualize under 300 nm UV light. Wells fluorescing orange/red indicate DNA amplification. Fluorescing wells are analyzed by 0.8% sodium borate agarose gel electrophoresis @ 250V for 20 mins.

17. Example 17: Post-VLPAS Amplicon Purification—TIMING: 30 Mins

Cherry pick VLPAS destined for sequencing to a new 96-well plate. Warm KAPA Pure Beads up to room temperature before use and then mix thoroughly by vortexing for ≥30 secs. Dispense 36 uL of KAPA Pure Beads into the MDA sample plate and mix thoroughly by pipetting. Incubate for DNA binding for 5 mins at room temperature. Place plate on a 96-well side magnet for 2 mins, and then carefully remove the supernatant. Add 200 uL of fresh 80% ethanol into each well of the MDA plate and incubate on the magnet for ≥30 secs. Carefully remove the ethanol and discard. Repeat once more for a second wash. Ensure all ethanol is removed and air dry for ~2.5 min Remove plate from the magnet and add 40 uL of 5 mM Tris-HCl (pH 8.0) to each well and pipette mix thoroughly. Incubate the plate at room temperature for 5 mins for DNA elution. Place the plate on the magnet for 2 mins, and transfer the supernatant (pure DNA) to a clean 96-well PCR plate. The purified VLPAS amplicons can be stored long term at −20° C.

18. Example 18: Integration Site Library Construction (Part 1: Restriction Digestion and Purification)—TIMING: 2 Hrs Remove KAPA Pure Beads from fridge to allow warming during the restriction digestion step. MDA wells that produced a VLPAS amplicon selected for sequencing are cherry picked to a new 96-well plate. Quantify and normalize cherry picked MDA wells to 50 ng/uL using the Quant-iT dsDNA PicoGreen kit, following the manufacturer's instructions. Transfer 20.25 uL of normalized MDA DNA to separate wells of a new 96-well plate. In the amplification room (inside a dead air hood when possible), prepare the restriction digestion mastermix according to Table 7, adding reagents in the order shown.

TABLE 7

ISA Restriction digestion mastermix.

| Reagent | Final Concentration | Vol. per reaction (uL) |
|---|---|---|
| 10X CutSmart Buffer |  | 2.5 |
| EcoRI-HF (20 U/uL) | 0.45 U/ul | 0.56 |
| BamHI-HF (20 U/uL) | 0.45 U/ul | 0.56 |
| NcoI-HF (20 U/uL) | 0.45 U/ul | 0.56 |
| BstZ17I-HF (20 U/uL) | 0.45 U/ul | 0.56 |
| Total Volume (uL): |  | 25 |
| Mastermix per reaction (uL): |  | 4.75 |

Add 4.75 uL of restriction digestion mastermix to each well of normalized MDA DNA. Mix by pipetting. Centrifuge plate at 1,000×g for 1 min at room temperature. Incubate at 37° C. for 1.5 hrs. Centrifuge plate at 1,000×g for 1 min at room temperature. Dilute sample wells with 25 uL of 5 mM Tris-HCl, pH 8.0. Add 30 uL of KAPA Pure Beads to the sample. Pipette mix well. Incubate for 7 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 2.5 mins. Add 25 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

19. Example 19: Integration Site Library Construction (Part 2: End/Nick Repair and Purification)—TIMING: 1 hr In the amplification room (inside a dead air hood when possible), prepare the end repair mastermix according to Table 8, adding reagents in the order shown.

TABLE 8

ISA End & nick repair mastermix

| Reagent | Final Concentration | Vol. per reaction (uL) |
|---|---|---|
| Molecular-grade water |  | 13.83 |
| Tris-HCl (1M, pH 8.0) | 30 mM | 1.5 |
| NaCl (1M) | 50 mM | 2.5 |
| MgCl$_2$ (0.5M) | 10 mM | 1 |
| DTT (100 mM) | 5 mM | 2.5 |
| dNTPs (10 mM) | 100 nM | 0.5 |
| BSA (20 mg/mL) | 100 ng/uL | 0.25 |
| NAD$^+$ (5 mM) | 30 uM | 0.3 |
| Triton-X-100 (2%) | 0.025% | 0.625 |
| Klenow Large Fragment (5 U/uL) | 0.05 U/uL | 0.5 |
| T4 DNA Polymerase (3 U/uL) | 0.03 U/uL | 0.5 |
| E. coli Ligase (10 U/uL) | 0.2 U/uL | 1 |
| Total Volume (uL): |  | 50 |
| Mastermix per reaction (uL): |  | 25 |

Add 25 uL of cold end repair mastermix to purified fragmented sample wells. Pipette mix well. Centrifuge plate at 1,000×g for 1 min at room temperature. Place plate on thermal cycler and run the following program: 1) 20° C. for 30 mins, 2) 4° C. hold. Centrifuge plate at 1,000×g for 1 min at room temperature. Place plate on a cold block and add 2 uL of 0.5M EDTA to each sample well to stop the reaction. Mix by pipetting. Add 52 uL of KAPA Pure Beads and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 2.5 mins. Add 30 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

20. Example 20: Integration Site Library Construction (Part 3: dA Tailing)—TIMING: 30 Mins In the amplification room (inside a dead air hood when possible), prepare the dA-tailing mastermix according to Table 9 in the order shown.

TABLE 9

ISA dA-Tailing mastermix

| Reagent | Final Concentration | Vol. per reaction (uL) |
|---|---|---|
| Molecular-grade water |  | 9.4 |
| Tris-HCl (1M, pH 8.0) | 15 mM | 0.75 |
| NaCl (1M) | 50 mM | 2.5 |
| MgCl$_2$ (0.5M) | 10 mM | 1 |
| DTT (100 mM) | 5 mM | 2.5 |
| dATP (10 mM) | 100 nM | 0.5 |

TABLE 9-continued

ISA dA-Tailing mastermix

| Reagent | Final Concentration | Vol. per reaction (uL) |
|---|---|---|
| BSA (20 mg/mL) | 100 ng/uL | 0.25 |
| Triton-X-100 (2%) | 0.025% | 0.625 |
| Klenow Exo - (5 U/uL) | 0.25 U/uL | 2.5 |
| | Total Volume (uL): | 50 |
| | Mastermix per reaction (uL): | 20 |

Add 20 uL of cold dA-tailing mastermix to each end repaired sample. Mix by pipetting. Centrifuge plate at 1,000×g for 1 min at room temperature. Place plate on thermal cycler and run following program: 1) 37° C. for 30 mins, 2) 4° C. hold.

21. Example 21: Integration Site Library Construction (Part 4: Nullomer Adapter Ligation and Purification)—TIMING: ~10 Mins Hands on/Overnight Incubation In the amplification room (inside a dead air hood when possible), prepare the ligation mastermix according to Table 10, adding reagents in the order shown.

TABLE 10

ISA Nullomer Adapter Ligation

| Reagent | Final Concentration | Vol. per reaction (uL) |
|---|---|---|
| Molecular-grade water | | 2.05 |
| MgCl$_2$ (100 mM) | 10 mM | 2.5 |
| DTT (1M) | 10 mM | 0.5 |
| ATP (100 mM) | 1.33 mM | 1 |
| PEG 6000 (50%) | 7.5% | 11.25 |
| T4 DNA Ligase (2000 U/uL) | 40 U/uL | 1.5 |
| | Total Volume (uL): | 75 |
| | Mastermix per reaction (uL): | 18.8 |

Add 6.2 uL of annealed Nullomer adapter (50 uM) to each sample well. Mix by pipetting. Add 18.8 uL of ligase mastermix to each sample well. Mix carefully by pipetting >30 times. Centrifuge plate at 1,000×g for 5 secs at room temperature. Place plate on thermal cycler and run the following program: 1) 20° C. for 4 hrs, 2) 16° C. for 4 hrs, 3) 4° C. hold overnight. Centrifuge plate at 1,000×g for 1 min at room temperature.

22. Example 22: Integration Site Library Construction (Part 5: Nullomer-Ligation Purification)—TIMING: ~30 Mins Add 45 uL of KAPA Pure Beads and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 3 mins Add 50 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

23. Example 23: Integration Site Library Construction (Part 6: Nullomer-Mediated Integration Site Nested PCR)—TIMING: 4 Hrs In the clean room, prepare the PCR1 and PCR2 mastermix according to Table 11, adding reagents in the order shown.

TABLE 11

ISA Nullomer-mediated PCR1 and PCR2 mastermix.

| Reagent | Final Concentration | Vol. per reaction (uL) |
|---|---|---|
| Molecular-grade water | | 2.4 |
| 5x SuperFi Buffer | 1x | 2 |
| dNTP (10 mM) | 200 nM | 0.2 |
| PCR 1: Nullomer Outer primer (10 uM) | 250 nM | 0.25 |
| PCR 2: Nullomer Inner primer (10 uM) | | |
| PCR 1: HIV Outer primer (10 uM) | 250 nM | 0.25 |
| PCR 2: HIV Inner primer (10 uM) | | |
| Bovine Thrombin (1 mg/mL) | 84 ug/mL | 0.84 |
| Betaine (5M) | 0.9M | 1.8 |
| ET SSB (500 ng/uL) | 8 ng/uL | 0.16 |
| Platinum SuperFi DNA Polymerase (2U/uL) | 0.02 U/uL | 0.1 |
| | Total Volume (uL): | 10 |
| | Mastermix per reaction (uL): | 8 |

Dispense 8 uL of mastermix to each well of separate 96-well or 384-well PCR1 and PCR2 plates. Add 2 uL of molecular grade water to: 1) wells G12 and H12 of the 96-well plate OR 2) wells O24 and P24 of a 384-well plate. Transfer plates to the amplification room and store at 4° C. Dilute 3 uL of pure Nullomer-ligated samples in 12 uL of 5 mM Tris-HCl, pH 8.0. Mix well by pipetting. Seed 2 uL of diluted sample in quadruplicate into separate wells of the PCR plate. Centrifuge plate at 1,000×g for 1 min at room temperature. Place plate on thermal cycler and run the following program: 1) 95° C. for 2 mins, 2) 98° C. for 10 secs, 3) 66.5° C. for 2 mins, 4) Steps 2-3 repeated 39×, 5) 66.5° C. for 4 mins, 6) 10° C. hold. Centrifuge plate at 1,000×g for 1 min at room temperature. Add 80 uL of 5 mM Tris-HCl, pH 8.0, to each PCR1 well. Mix by pipetting. Transfer 2 uL of each diluted PCR1 to their respective well in the PCR2 mastermix plate. Centrifuge plate at 1,000×g for 1 min at room temperature. Place plate on thermal cycler and run the following program: 1) 95° C. for 2 mins, 2) 98° C. for 10 secs, 3) 66.5° C. for 2 mins, 4) Steps 2-3 repeated 39×, 5) 66.5° C. for 4 mins, 6) 10° C. hold. Centrifuge plate at 1,000×g for 1 min at room temperature. Add 40 uL of 5 mM Tris-HCl, pH 8.0, to each PCR2 well. Mix by pipetting.

24. Example 24: Integration Site Library Construction (Part 7: EvaGreen qPCR Amplicon Detection)—TIMING: ~1.5 hr In the clean room, prepare the HIV U5 EvaGreen qPCR mastermix according to Table 12, adding reagents in the order shown.

TABLE 12

ISA U5 EvaGreen qPCR mastermix.

| Reagent | Final Concentration | Vol. per reaction (uL) |
|---|---|---|
| Molecular-grade water | | 4.6 |
| 10X ThermoPol Buffer | 1x | 1 |
| MgSO$_4$ (50 mM) | 1.5 mM | 0.3 |

TABLE 12-continued

ISA U5 EvaGreen qPCR mastermix.

| Reagent | Final Concentration | Vol. per reaction (uL) |
|---|---|---|
| dNTPs (10 mM) | 0.4 mM | 0.4 |
| US FWD primer (50 uM) | 250 nM | 0.05 |
| US REV primer (50 uM) | 250 nM | 0.05 |
| 20X EvaGreen dye | 1x | 0.5 |
| ROX Passive dye (2.5 uM) | 0.05 uM | 0.02 |
| BSA (20 mg/mL) | 100 ng/uL | 0.05 |
| HotStart Taq (5 U/uL) | 0.025 U/uL | 0.05 |
| Total Volume (uL): | | 10 |
| Mastermix per reaction (uL): | | 7 |

Dispense 7 uL of mastermix to each well of a 96-well or 384-well plate. Transfer plate to amplification room and store at 4° C. Transfer 2 uL of 1:5 diluted nullomer-PCR2 wells into a new plate containing 16 uL of 5 mM Tris-HCl, pH 8.0, in each well. Mix by pipetting. Transfer 4 uL of the 1:45 dilution plate wells into a new plate containing 94 uL of 5 mM Tris-HCl, pH 8.0. Mix by pipetting. Transfer 3 uL of the 1:1,000 diluted nullomer-PCR2 plate into the qPCR mastermix plate. Mix by pipetting. Transfer 3 uL of positive control amplicon into qPCR well H12 or P24. Centrifuge the qPCR plate at 1,000×g for 1 min at room temperature. Place the plate on a qPCR machine and run the following program: 1) 95° C. for 3 mins, 2) 95° C. for 15 secs, 3) 57° C. for 20 secs, 4) 72° C. for 20 secs (Read fluorescence), 5) Steps 2 through 4 repeated 29×, 6) Melt curve. Analyze Nullomer-PCR2 wells with Ct's<25 and melt curves similar to positive control (typically ~81.0° C.) by 0.8% sodium borate gel analysis at 250V for 20 mins.

25. Example 25: Integration Site Library Construction (Part 8: Integration Site Amplicon Purification)—TIMING: ~30 Mins Add 45 uL of KAPA Pure Beads and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 2.5 mins. Add 30 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

26. Example 26: In-House Illumina Library Construction (Part 1: Preflight DNA Normalization)—TIMING: Variable Normalize DNA amplicons for sequencing to 3 ng/uL using 5 mM Tris-HCl, pH 8.0. Dispense 16 uL of normalized amplicons to new wells of a 96-well plate.

27. Example 27: In-House Illumina Library Construction (Part 2: Fragmentation and Purification)—TIMING: ~50 Mins Thaw the dsDNA fragmentase buffer at room temperature, and return to ice before using for >3 mins. Dispense 2 uL of 10× dsDNA Fragmentase buffer into each sample carefully. Pipette mix 15 uL with a multichannel pipette at least 5× times to thoroughly mix the buffer with sample. Vortex the dsDNA Fragmentase enzyme for 3 seconds prior to use. Flash spin briefly in a minicentrifuge. Dispense 2 ul of enzyme into each sample well. Pipette mix 2× in each well to rinse enzyme from tips. Pipette mix 16 ul at least 7× times while keeping samples on cold block. Quickly centrifuge the fragmentation plate at 500×g for 3 secs. Place fragmentation plate on thermal cycler (pre-chilled to 0° C.) and incubate at 37° C. for either 1) 13 mins for VLPAS amplicons OR 2) 4 mins for integration site amplicons. Immediately place on freezing cold ice block & add 5 ul of 0.5M EDTA. Mix reaction well. Pipette mix. Dilute sample plate wells with 15 uL of 5 mM Tris-HCl, pH 8.0. Add 40 uL of KAPA Pure Beads and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 3 mins. Add 25 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

28. Example 28: In-House Illumina Library Construction (Part 3: End/Nick Repair and Purification)—TIMING: ~1 hr Prepare the Illumina End/Nick repair mastermix according to Table 13, adding reagents in the order shown.

TABLE 13

Illumina Library Construction End/Nick Repair mastermix.

| Reagent | Final Concentration | Vol. per reaction (uL) |
|---|---|---|
| Molecular-grade water | | 12.8 |
| Tris-HCl (pH 8.0) | 30 mM | 1.5 |
| NaCl (1M) | 50 mM | 2.5 |
| $MgCl_2$ (0.5M) | 10 mM | 1 |
| DTT (100 mM) | 5 mM | 2.5 |
| dNTP (10 mM) | 0.1 mM | 0.5 |
| BSA (20 mg/mL) | 100 ng/uL | 0.25 |
| $NAD^+$(5 mM) | 30 uM | 0.3 |
| Triton-X-100 (2%) | 0.025% | 0.625 |
| Large Klenow Fragment (5 U/uL) | 0.05 U/uL | 0.5 |
| T4 DNA Polymerase (3 U/uL) | 0.03 U/uL | 0.5 |
| T4 Polynucleotide Kinase (10 U/uL) | 0.2 U/uL | 1 |
| E. coli Ligase (10 U/uL) | 0.2 U/uL | 1 |
| Total Volume (uL): | | 50 |
| Mastermix per reaction (uL): | | 25 |

Dispense 25 uL of cold End/Nick repair mastermix into the purified fragmented samples. Pipette mix well. Centrifuge the plate at 1,000×g at room temperature for 1 min. Place the plate on the thermal cycler and run the following program: 1) 20° C. for 30 mins, 2) 12° C. hold. Add 50 uL of KAPA Pure Beads and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 3 mins. Add 30 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

29. Example 29: In-House Illumina Library Construction (Part 4: dA-Tailing)—TIMING: ~50 Mins Prepare the Illumina dA-Tailing mastermix according to Table 14, adding reagents in the order shown.

TABLE 14

Illumina Library Construction dA-Tailing mastermix.

| Reagent | Final Concentration | Vol. per reaction (uL) |
|---|---|---|
| Molecular-grade water | | 10.38 |
| Tris-HCl (pH 8.0) | 15 mM | 0.75 |
| NaCl (1M) | 50 mM | 2.5 |
| MgCl$_2$ (0.5M) | 10 mM | 1 |
| DTT (100 mM) | 5 mM | 2.5 |
| dATP (10 mM) | 0.1 mM | 0.5 |
| BSA (20 mg/mL) | 100 ng/uL | 0.25 |
| Triton-X-100 (2%) | 0.025% | 0.625 |
| Klenow Exo- (5 U/uL) | 0.15 U/uL | 1.5 |
| Total Volume (uL): | | 50 |
| Mastermix per reaction (uL): | | 20 |

Dispense 20 uL of cold End/Nick repair mastermix into the purified fragmented samples. Pipette mix well. Centrifuge the plate at 1,000×g at room temperature for 1 min. Incubate at 37° C. for 45 mins, followed by a 4° C. hold. Proceed directly to Part 5: Adapter Ligation.

30. Example 30: In-House Illumina Library Construction (Part 5: Adapter Ligation and Purification)—TIMING: ~1.5 Hrs Prepare the Illumina Ligation mastermix according to Table 15, adding reagents in the order shown.

TABLE 15

Illumina Library Construction Ligation mastermix.

| Reagent | Final Concentration | Vol. per reaction (uL) |
|---|---|---|
| Molecular-grade water | | 4.25 |
| MgCl$_2$ (100 mM) | 10 mM | 2.5 |
| DTT (1M) | 10 mM | 0.5 |
| ATP (100 mM) | 1.3 mM | 1 |
| PEG 6000 (50%) | 7.5% | 11.25 |
| T4 DNA Ligase (2000 U/uL) | 13.3 U/uL | 0.5 |
| Total Volume (uL): | | 75 |
| Mastermix per reaction (uL): | | 20 |

Add 5 uL of Illumina sequencing adapter (1 uM) to each sample well. Mix by pipetting. Add 20 uL of cold ligation mastermix to each sample well carefully. Mix thoroughly by pipetting. Centrifuge the plate at 1,000×g at room temperature for 1 min. Incubate at 16° C. for 30 mins, then place at 4° C. until purification. Centrifuge the plate at 1,000×g at room temperature for 1 min. Dilute ligation plate with 35 uL of 5 mM Tris-HCl, pH 8.0. Add 88 uL of KAPA Pure Beads and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 3 mins. Add 50 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate. Add 30 uL of KAPA Pure Beads and mix thoroughly by pipetting. Incubate for 5 minutes at room temperature. Place plate on magnet for 2 mins to separate beads. Carefully transfer the supernatant to a clean 96-well plate. Discard the plate with leftover beads. Add 10 uL of KAPA Pure Beads to the transferred supernatant and mix thoroughly by pipetting. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 3 mins. Add 30 uL of 5 mM Tris-HCl, pH 8.0, to each well and pipette mix thoroughly. Incubate plate for 5 mins at room temperature. Place plate on magnet for 2 mins to separate beads. Transfer supernatant (pure DNA) to clean wells of a 96-well plate.

31. Example 31: In-House Illumina Library Construction (Part 6: Illumina PCR and Purification)—TIMING: ~1 hr In a clean room, prepare the Illumina PCR mastermix according to Table 16, adding reagents in the order shown.

TABLE 16

Illumina Library Construction PCR mastermix.

| Reagent | Final Concentration | Vol. per reaction (uL) |
|---|---|---|
| Molecular-grade water | | 6 |
| 5x SuperFi Buffer | 1x | 10 |
| dNTPs (10 mM) | 0.2 mM | 1 |
| P5 primer (10 uM) | 250 nM | 1.25 |
| P7 primer (10 uM) | 250 nM | 1.25 |
| Platinum SuperFi DNA Polymerase (2 U/uL) | 0.02 U/uL | 0.5 |
| Total Volume (uL): | | 50 |
| Mastermix per reaction (uL): | | 20 |

Dispense 20 uL of PCR mastermix into all wells of a 96-well of 384-well plate. Transfer the plate to the amplification room and store at 4° C. Transfer 30 uL of ligated purified libraries to the PCR mastermix plate. Mix by pipetting. Centrifuge the plate at 1,000×g for 1 min at room temperature. Place the plate on a thermal cycler and run the following program: 1) 95° C. for 3 mins, 2) 98° C. for 15 secs, 3) 65° C. for 20 secs, 4) 72° C. for 30 secs, 5) Steps 2 through 4 repeated 11×, 6) 72° C. for 90 secs, 7) 10° C. hold. Centrifuge the plate at 1,000×g for 1 min at room temperature. Add 50 uL of KAPA Pure Beads to PCR reactions and mix thoroughly by pipetting. Incubate for 5 minutes at room temperature. Place plate on magnet for 2 mins to separate beads. Carefully remove and discard supernatant. Add 200 uL of fresh 80% ethanol to the sample wells. Incubate plate on magnet for ≥30 secs. Remove and discard supernatant. After the second ethanol wash, ensure all ethanol is removed from bottom of well with a pipette. Air dry for 3 mins. Add 30 uL of 5 mM Tris-HCl, pH 8.0, to each well and pipette mix thoroughly. Incubate plate for 5 mins

32. Example 32: In-House Illumina Library Construction (Part 7: Post-PCR Quantification and Normalization)—TIMING: ~Variable Quantify and normalize purified libraries to 6.5 ng/uL in 20 uL of 5 mM Tris-HCl, pH 8.0, using the Quant-iT dsDNA PicoGreen kit following the manufacturer's instructions. Using a multichannel pipette, transfer 10 uL from each plate column of normalized libraries into a strip tube. Combine and transfer the pooled libraries from the strip tube wells into a microcentrifuge tube. Add 0.8× the volume of the pooled libraries of KAPA Pure Beads into the pool tube. Mix well by pipetting. Incubate for 5 minutes at room temperature. Place tube on magnet for 5 mins to separate beads or until sample is clear. Carefully remove and discard supernatant. Add 1,000 uL of fresh 80% ethanol to the sample wells. Incubate tube on magnet for ≥30 secs. Remove and discard supernatant. After the second ethanol wash, ensure all ethanol is removed from bottom of well with a pipette. Air dry for 5-8 mins. Add 30 uL of 5 mM Tris-HCl, pH 8.0, to the tube and vortex. Incubate tube for 5 mins at room temperature. Place tube on magnet for 2 mins to separate beads. Transfer supernatant (pure DNA libraries) to a clean strip tube well.

33. Example 33: In-House Illumina Library Construction (Part 8: Sage Blue Pippin Size Selection)—TIMING: ~45 Mins Add 10 uL of the Blue Pippin loading solution with internal standards to the 30 uL of purified pooled libraries. Mix well by pipetting. Set up and run the Blue Pippin instrument according to the manufacturer's instructions for 0.75% Agarose cassettes with internal 51 standards, using a Broad collection setting targeting 300 to 600 bp fragments (target 450 bp). After separation, add an equal volume of KAPA Pure Beads to the Sage purified pooled sample. Incubate for 5 minutes at room temperature. Place tube on magnet for 5 mins to separate beads or until sample is clear. Carefully remove and discard supernatant. Add 1,000 uL of fresh 80% ethanol to the sample wells. Incubate tube on magnet for ≥30 secs. Remove and discard supernatant. After the second ethanol wash, ensure all ethanol is removed from bottom of well with a pipette. Air dry for 3.5 mins. Add 30 uL of 5 mM Tris-HCl, pH 8.0, to the tube and vortex. Incubate tube for 5 mins at room temperature. Place tube on magnet for 2 mins to separate beads. Transfer supernatant (pure DNA libraries) to a clean microcentrifuge tube.

34. Example 34: Quantification and Bioanalysis of Purified, Size Selected, and Pooled Amplicon Libraries—TIMING: ~30 Mins to 1 hr Using your preferred method, assess the mean fragment size of the pooled purified library. It is highly suggested to use a Perkin Elmer LabChip or an equivalent bioanalyzer, and not agarose gel electrophoresis. Quantify the pooled purified sample using either a commercial Illumina SYBR Green qPCR kit or the Quant-iT dsDNA PicoGreen assay in quadruplicate. Calculate the molarity of the pooled purified sample using the following equation:

$$(ng/uL/(660 * Mean\ Frag\ Size)) * 10^6 = nM$$

Carefully create a 2 nM stock of the sample using at least 5 uL of purified pooled sample for dilution.

35. Example 35: Sample and PhiX Control Preparation—TIMING: ~12 Mins

Dilute a 2N NaOH stock to 0.2N (20 ul of 2N NaOH into 180 ul of molecular-grade H2O). Vortex thoroughly. Thoroughly mix your 2 nM pooled library by vortexing. Dispense 5 ul of 2 nM pooled library into a microcentrifuge tube, then add 5 ul of 0.2N NaOH to the library. Cap and vortex vigorously. Flash spin in a minicentrifuge. Incubate for 5 mins at room temperature. Dispense 5 ul of 200 mM Tris-HCl, pH 7.0, into the denatured sample. Immediately add 985 ul of ice-cold HT1 buffer. Mix by vortexing for >7 secs. Dilute 525 ul of 10 pM denatured library into 225 ul of HT1 buffer. Mix by vortexing for >7 secs and place on ice. Vortex and spin down the PhiX control. Dispense 2 ul of PhiX Control (10 nM) into a microcentrifuge tube. Dispense 3 ul of 10 mM Tris-HCl (pH 8.5)/0.1% Tween 20 into the microcentrifuge tube. Mix by pipetting. Dispense 5 ul of 0.2N NaOH into the diluted PhiX tube. Vortex thoroughly and flash spin in a minicentrifuge. Incubate for 5 mins at room temperature. Dispense 5 ul of 200 mM Tris-HCl, pH 7.0 into denatured PhiX library Immediately dilute the denatured PhiX library with 985 ul of ice-cold HT1 buffer. Vortex thoroughly. In a new microcentrifuge tube, carefully mix 375 ul of PhiX (20 pM) with 225 ul of cold HT1 buffer. Finally, combine 510 ul of denatured 7 pM pooled library with 90 ul of 12.5 pM denatured PhiX control. Vortex thoroughly, spin down, and keep on ice until ready to load MiSeq.

36. Example 36: Illumina MiSeq Loading—TIMING: ~15 Mins

Using the Illumina Experiment Manager, create a sample sheet using the Illumina TruSeq dual index barcodes utilized. Load the MiSeq using a 500 cycle v2 nano reagent kit as the manufacturer recommends, using a dual index, paired end 250×250 cycle sequencing run.

37. Example 37: Efficient High-Throughput Sequencing of Variable and Near Full Length Integrated HIV-1 Proviruses Efforts to cure HIV-1 infection will require a better understanding of the proviral reservoir that persists despite current antiretroviral therapies, but current methods are expensive due to current technological limitations and inefficient sequencing (>98% loss of reads). Intact HIV proviruses integrated in the human genome allow persistence of long-term infection, despite long-term suppressive ART. These proviral DNA targets are rare (1 in 1,000 CD4+ T cells), and their rarity makes efficient and high-throughput amplification across unknown host-virus junctions difficult for single copy targets. Current methods are very costly and discard >98% of sequencing reads as background, and also cannot pair proviruses with integration sites efficiently. These limitations have inhibited in-depth characterization of the proviral reservoir that needs to be targeted to achieve a cure of HIV-1 infection or determine if an intervention has worked. This improved workflow allows for enrichment and high-plexity sequencing of a single-genome, variable and near-full length HIV proviruses and their integration sites, in which >88% of sequencing reads are utilized during assembly.

a) Results

Proviral DNA amplified varies due to deletions, indels, and other genomic defects, but all of individual provirus is amplified except the 5'LTR and 69 bp of the 3'LTR U5 (FIG. 8). Proviral DNA from MDA wells containing proviruses undergo nullomer adapter ligation, followed host-virus PCR, amplifying a portion of Psi and all of the 5'LTR, and variable lengths of 5' flanking host sequence. Shown above are PCR replicates of 4 different MDA wells separated by GeneRuler 1 kb+ ladders (FIG. 9). Average success rate of 71% for enriching integration sites from MDA wells containing proviruses without PBS deletions. >90% of sequencing reads are utilized for both proviral and integration site consensus sequence assembly. Amplification of proviruses in one variable length amplicon by priming within U5 allows for dynamic mapping of indels, genome inversions, and other major defects, and amplifies all but 69 bp of the 3' LTR of both variable and full-length integrated provirus. For the host-virus amplicon, priming within gag leader provides reverse directionality and sequencing of the entire 5LTR and variable amounts of flanking host sequence (FIGS. 10A, 10B, 10C, 10D, and 10E). The validity of the assay has been confirmed by sequence identity with deleted and full-length proviruses amplified directly from PBMCs using host sequences flanking the integrated provirus. The overall percent efficiency of enriching integration sites from VLPAS(+) MDA wells across five subtype B donors was 70.6%±15.8% (FIGS. 11A and 11B).

b) Discussion

Across 5 donors, an average of 70.6%±15.8% of MDA wells containing proviruses successfully had their integration sites amplified and sequenced. The very high level of specificity provided during nullomer-mediated host-virus PCR allows high levels of multiplexing during NGS sequencing, dramatically reducing the cost of sequencing integration sites. It is not uncommon with previous technologies for only a few samples to be loaded onto a MiSeq for integration site sequencing. We have accomplished 96-plexing on MiSeq v2 nano kits, the smallest MiSeq reagent kit available. The ability to enrich up to 1.5 kb of flanking host sequence allows for unequivocal calling of integration sites even within ambiguous genomic regions. Lastly, sequencing all but 69 bp of integrated proviruses allows for characterization of clonally expanded proviruses with significantly improved ability to map genomic defects (like major deletions) including those in the 5' and 3' LTRs that would otherwise be unidentifiable by overlapping proviral amplicon methods. The method provides an efficient and high-throughput means of sequencing single genome integrated HIV proviruses and can be used to provide in-depth characterization of proviral reservoirs that need to be targeted to achieve a cure of HIV-1 infection. Additionally, this method can be used to assess the effect of clinical interventions on the proviral reservoir, a crucial metric for assessing drug efficacy, etc.

c) Methods

Genomic DNA from blood mononuclear cells is extracted, serially diluted, and used for PCR to identify the proviral end point dilution. End point diluted gDNA is amplified using multiple displacement isothermal amplification. MDA wells are screened for proviruses using variable-length proviral PCR. MDA wells with proviruses are selected for integration site DNA preparation and PCR. Amplicons can be sequenced by dideoxy sequencing (Sanger) or NGS (see FIG. 3).

Nullomers can be used to enhance specificity of linker-mediated PCR (LM-PCR). The Nullomer adapter is a partially dsDNA 71-mer oligonucleotide comprised of sequences absent in the human and HIV genomes. This drastically reduces unintended mis-priming from adapter primers in either genomes, which inhibits traditional LM-PCR. Nullomer ligated fragments are not amplifiable until the adapter is regenerated during PCR using HIV-specific reverse primers.

D. References

Leoni C, Volpicella M, De Leo F, Gallerani R, Ceci L R. Genome walking in eukaryotes. FEBS J. 2011 November; 278(21):3953-77. doi: 10.1111/j.1742-4658.2011.08307.x. Epub 2011 Sep. 15. Review. PubMed PMID: 21848672.

Maldarelli F, Wu X, Su L, Simonetti F R, Shao W, Hill S, Spindler J, Ferris A L, Mellors J W, Kearney M F, Coffin J M, Hughes S H. HIV latency. Specific HIV integration sites are linked to clonal expansion and persistence of infected cells. Science. 2014 Jul. 11; 345(6193):179-83. doi: 10.1126/science.1254194. Epub 2014 Jun. 26. PubMed PMID: 24968937; PubMed Central PMCID: PMC4262401.

Serrao E, Cherepanov P, Engelman A N. Amplification, Next-generation Sequencing, and Genomic DNA Mapping of Retroviral Integration Sites. J Vis Exp. 2016 Mar. 22; (109). doi: 10.3791/53840. PubMed PMID: 27023428; PubMed Central PMCID: PMC4829050.

E. Sequences

```
SEQ ID NO: 1 > Sense_v1.0_TA
GATACCTTAGCGATGGACAGTACGATACCTACTCCCTGGCGACCTGATATGATTAGC
GTTGTGCGAGCG*G*T SEQ ID NO: 2 > Antisense_v1.0_TA
/5Phos/CCGCTCGCACAACG/iSpC3/C/3SpC3/

SEQ ID NO: 3 Outer PCR
5'-GATACCTTAGCGATGGACAGTACGATAC*C*T

SEQ ID NO: 4 Middle PCR
5'-TAGCGATGGACAGTACGATACCTACTCC*C*T

SEQ ID NO: 5 Inner PCR
5'-GATACCTACTCCCTGGCGACCTGATATGA*T*T

SEQ ID NO: 6 Seq Primer
5'-CGACCTGATATGATTAGCGTT
```

| E. Sequences |
|---|

SEQ ID NO: 7 892-_v2
5'-AYCGTTCTARYTCCCTGCTTGCCCAT*A*C

SEQ ID NO: 8 688-_v2.1
5'-CYTCAGCAAGCCGAGTCCTGCG*T*C

SEQ ID NO: 9 NFL_v2_OuterFWD_Phusion
5'-AGTCAGTGTGGAAAATCTCT*A*G

SEQ ID NO: 10 NFL_v2_OuterREV_Phusion
5'-GAGGGATCTCTAGTTACCAG*A*G

SEQ ID NO: 11 NFL_v2_InnerFWD_Phusion
5'-GTGGAAAATCTCTAGCAGT*G*G

SEQ ID NO: 12 NFL_v2_InnerREV_Phusion
5'-TTACCAGAGTCACACAACAG*A*C

SEQ ID NO: 13 U5_qPCR_FWD_522+ screening for LTR
5'-GGGAACCCACTGCTTAAG

SEQ ID NO: 14 U5_qPCR_REV_616- screening for LTR
5'-CCACTGCTAGAGATTTTCCACAC

SEQ ID NO: 15 ILMN P5 PCR Primer
5'-AATGATACGGCGACCACCGA*G

SEQ ID NO: 16 ILMN P7 PCR Primer
5'-CAAGCAGAAGACGGCATACGA*G

SEQ ID NO: 17 P5 Adapter
AATGATACGGCGACCACCGAGATCTACACTATAGCCTACACTCTTTCCCTACACGAC
GCTCTTCCGATC*T SEQ ID NO: 18 P7 Adapter
/5Phos/GATCGGAAGAGCACACGTCTGAACTCCAGTCACATTACTCGATCTCGTATGC
CGTCTTCTGCTTG
* = phosphorothioate bonds
/3SpC3/ = C3 spacer
/5Phos/ = 5' phosphate SEQ ID NO: 19 VLPAS PCR primers VLPAS_OuterFWD
AGT CAG TGT GGA AAA TCT CT*A *G SEQ ID NO: 20 VLPAS PCR primers VLPAS_OuterREV
GAG GGA TCT CTA GTT ACC AG*A *G SEQ ID NO: 21 VLPAS PCR primers VLPAS_InnerFWD
GTG GAA AAT CTC TAG CAG T*G*G SEQ ID NO: 22 VLPAS PCR primers VLPAS_InnerREV
TTA CCA GAG TCA CAC AAC AG*A *C SEQ ID NO: 23 HIV-1 subtype B universal Nullomer-mediated PCR primers
Nullomer_v2_OuterFWD
GAT ACC TTA GCG ATG GAC AGT ACG ATA C*C*T SEQ ID NO: 24 HIV-1 subtype B universal Nullomer-mediated PCR primers
Nullomer_v2_InnerFWD
TAG CGA TGG ACA GTA CGA TAC CTA CTC C*C*T SEQ ID NO: 25 HIV-1 subtype B universal Nullomer-mediated PCR primers
HIV_OuterREV_UNV
CCG CTT AAT AYY GAC GCT CTC *G*C
(1$^{st}$ Y: 75% C. 25% T, 2$^{nd}$ Y: 75% T, 25% C)

SEQ ID NO: 26 HIV-1 subtype B universal Nullomer-mediated PCR primers
HIV_InnerREV_UNV
CYT CAG CAA GCC GAG TCC TGC G*T*C
(Y: 90% T, 10% C)

SEQ ID NO: 27 HIV-1 Subtype-B US qPCR primers, (OH'S-3'OH), standard desalting
OK HIV_623_REV
CGC CAC TGC TAG AGA TTT

E. Sequences

SEQ ID NO: 28 HIV-1 Subtype B-donor specific Nullomer-mediated PCR primers, HIV_OuterREV_C-03
CCG CTT AAT ACT GAC GCT CTC *G*C SEQ ID NO: 29 HIV-1 Subtype B-donor specific Nullomer-mediated PCR primers, HIV_OuterREV_F-07
CCG CTT AAT ATT GAC GCT CTC *G*C SEQ ID NO: 30 HIV-1 Subtype B-donor specific Nullomer-mediated PCR primers, HIV_OuterREV_K-01_C-02
CCG CTT AAT ACT GAC GCT CTY *G*C SEQ ID NO: 31 HIV-1 Subtype B-donor specific Nullomer-mediated PCR primers, HIV_OuterREV_R-09_TT
CCG CTT AAT ATT GAC GCT CTC *G*C SEQ ID NO: 32 HIV-1 Subtype B-donor specific Nullomer-mediated PCR primers, HIV_OuterREV_R-09_CC
CCG CTT AAT ACC GAC GCT CTC *G*C SEQ ID NO: 33 HIV-1 Subtype B-donor specific Nullomer-mediated PCR primers, HIV_OuterREV_R-09_CT
CCG CTT AAT ACT GAC GCT CTC *G*C SEQ ID NO: 34 HIV-1 Subtype-B 5'LTR and host junction dideoxy sequencing primers HIV_522_FWD
GGG AAC CCA CTG CTT AAG SEQ ID NO: 35 HIV-1 Subtype-B 5'LTR and host junction dideoxy sequencing primers HIV_623_REV
CGC CAC TGC TAG AGA TTT SEQ ID NO: 36 HIV-1 Subtype-B 5'LTR and host junction dideoxy sequencing primers HIV_90_REV
CCC TGG CCC TGG TGT GTA SEQ ID NO: 37 HIV-1 Subtype-B 5'LTR and host junction dideoxy sequencing primers HIV_107_FWD
TAC ACA CCA GGG CCA GGG SEQ ID NO: 38 HIV-1 Subtype-B U5 qPCR primers, (OH'5-3'OH), standard desalting OK HIV_522_FWD
GGG AAC CCA CTG CTT AAG SEQ ID NO: 39: Nullomer dsDNA Adapter Oligonucleotides, Nullomer_v2_Sense_v1.0_TA
GATACCTTAGCGATGGACAGTACGATACCTACTCCCTGGCGACCTGATATGATTAGCGTTGTGCGAGCG*G*T SEQ ID NO: 40 Nullomer dsDNA Adapter Oligonucleotides, Nullomer_v2_Antisense_v1.0_TA
/5Phos/CCGCTCGCACAACG/iSpC3/C/3SpC3/

SEQ ID NO: 41: Illumina Library Construction PCR primers ILMN P5 PCR Primer
AAT GAT ACG GCG ACC ACC GA*G SEQ ID NO: 42 Illumina Library Construction PCR primers ILMN P7 PCR Primer
CAA GCA GAA GAC GGC ATA CGA *G SEQ ID NO: 43 Illumina Library Construction Sequencing Adapters D501
AATGATACGGCGACCACCGAGATCTACACTATAGCCTACACTCTTTCCCTACACGACGCTCTTCCGATC*T SEQ ID NO: 44 Illumina Library Construction Sequencing Adapters D502
AATGATACGGCGACCACCGAGATCTACACATAGAGGCACACTCTTTCCCTACACGACGCTCTTCCGATC*T SEQ ID NO: 45 Illumina Library Construction Sequencing Adapters D503
AATGATACGGCGACCACCGAGATCTACACCCTATCCTACACTCTTTCCCTACACGACGCTCTTCCGATC*T SEQ ID NO: 46 Illumina Library Construction Sequencing Adapters D504
AATGATACGGCGACCACCGAGATCTACACGGCTCTGAACACTCTTTCCCTACACGACGCTCTTCCGATC*T

| E. Sequences |
| --- |
| SEQ ID NO: 47 Illumina Library Construction Sequencing Adapters D505<br>AATGATACGGCGACCACCGAGATCTACACAGGCGAAGACACTCTTTCCCTACACGA<br>CGCTCTTCCGATC*T<br><br>SEQ ID NO: 48 Illumina Library Construction Sequencing Adapters D506<br>AATGATACGGCGACCACCGAGATCTACACTAATCTTAACACTCTTTCCCTACACGAC<br>GCTCTTCCGATC*T<br><br>SEQ ID NO: 49 Illumina Library Construction Sequencing Adapters D507<br>AATGATACGGCGACCACCGAGATCTACACCAGGACGTACACTCTTTCCCTACACGA<br>CGCTCTTCCGATC*T<br><br>SEQ ID NO: 50 Illumina Library Construction Sequencing Adapters D508<br>AATGATACGGCGACCACCGAGATCTACACGTACTGACACACTCTTTCCCTACACGAC<br>GCTCTTCCGATC*T<br><br>SEQ ID NO: 51 Illumina Library Construction Sequencing Adapters D701<br>/5Phos/GATCGGAAGAGCACACGTCTGAACTCCAGTCACATTACTCGATCTCGTATGC<br>CGTCTTCTGCTTG<br><br>SEQ ID NO: 52 Illumina Library Construction Sequencing Adapters D702<br>/5Phos/GATCGGAAGAGCACACGTCTGAACTCCAGTCACTCCGGAGAATCTCGTATGC<br>CGTCTTCTGCTTG<br><br>SEQ ID NO: 53 Illumina Library Construction Sequencing Adapters D703<br>/5Phos/GATCGGAAGAGCACACGTCTGAACTCCAGTCACCGCTCATTATCTCGTATGC<br>CGTCTTCTGCTTG<br><br>SEQ ID NO: 54 Illumina Library Construction Sequencing Adapters D704<br>/5Phos/GATCGGAAGAGCACACGTCTGAACTCCAGTCACGAGATTCCATCTCGTATGC<br>CGTCTTCTGCTTG<br><br>SEQ ID NO: 55 Illumina Library Construction Sequencing Adapters D705<br>/5Phos/GATCGGAAGAGCACACGTCTGAACTCCAGTCACATTCAGAAATCTCGTATGC<br>CGTCTTCTGCTTG<br><br>SEQ ID NO: 56 Illumina Library Construction Sequencing Adapters D706<br>/5Phos/GATCGGAAGAGCACACGTCTGAACTCCAGTCACGAATTCGTATCTCGTATGC<br>CGTCTTCTGCTTG<br><br>SEQ ID NO: 57 Illumina Library Construction Sequencing Adapters D707<br>/5Phos/GATCGGAAGAGCACACGTCTGAACTCCAGTCACCTGAAGCTATCTCGTATGC<br>CGTCTTCTGCTTG<br><br>SEQ ID NO: 58 Illumina Library Construction Sequencing Adapters D708<br>/5Phos/GATCGGAAGAGCACACGTCTGAACTCCAGTCACTAATGCGCATCTCGTATGC<br>CGTCTTCTGCTTG<br><br>SEQ ID NO: 59 Illumina Library Construction Sequencing Adapters D709<br>/5Phos/GATCGGAAGAGCACACGTCTGAACTCCAGTCACCGGCTATGATCTCGTATGC<br>CGTCTTCTGCTTG<br><br>SEQ ID NO: 60 Illumina Library Construction Sequencing Adapters D710<br>/5Phos/GATCGGAAGAGCACACGTCTGAACTCCAGTCACTCCGCGAAATCTCGTATGC<br>CGTCTTCTGCTTG<br><br>SEQ ID NO: 61 Illumina Library Construction Sequencing Adapters D711<br>/5Phos/GATCGGAAGAGCACACGTCTGAACTCCAGTCACTCTCGCGCATCTCGTATGC<br>CGTCTTCTGCTTG<br><br>SEQ ID NO: 62 Illumina Library Construction Sequencing Adapters D712<br>/5Phos/GATCGGAAGAGCACACGTCTGAACTCCAGTCACAGCGATAGATCTCGTATGC<br>CGTCTTCTGCTTG<br><br>SEQ ID NO: 63 Hg19_specific_antiHIV_random_decamer oligonucleotide<br>CTC AGC CT*C* C<br><br>SEQ ID NO: 64 Hg19_specific_antiHIV_random_decamer oligonucleotide<br>CCT CAG CC*T* C<br><br>SEQ ID NO: 65 Hg19_specific_antiHIV_random_decamer oligonucleotide<br>GCC TCA GC*C* T<br><br>SEQ ID NO: 66 Hg19_specific_antiHIV_random_decamer oligonucleotide<br>GCC TCC CA*A* A |

| E. Sequences |
|---|

SEQ ID NO: 67 Hg19_specific_antiHIV_random_decamer oligonucleotide
TCA GCC TC*C* C SEQ ID NO: 68 Hg19_specific_antiHIV_random_decamer oligonucleotide
CCT CCC AA*A* G SEQ ID NO: 69 Hg19_specific_antiHIV_random_decamer oligonucleotide
TTT GTA TT*T* T SEQ ID NO: 70 Hg19_specific_antiHIV_random_decamer oligonucleotide
TTT TGT AT*T* T SEQ ID NO: 71 Hg19_specific_antiHIV_random_decamer oligonucleotide
AGG CTG GA*G* T SEQ ID NO: 72 Hg19_specific_antiHIV_random_decamer oligonucleotide
GCT CAC TG*C* A SEQ ID NO: 73 Hg19_specific_antiHIV_random_decamer oligonucleotide
GTA GCT GG*G* A SEQ ID NO: 74 Hg19_specific_antiHIV_random_decamer oligonucleotide
TGC CTC AG*C* C SEQ ID NO: 75 Hg19_specific_antiHIV_random_decamer oligonucleotide
AGT AGC TG*G* G SEQ ID NO: 76 Hg19_specific_antiHIV_random_decamer oligonucleotide
CAG GCT GG*A* G SEQ ID NO: 77 Hg19_specific_antiHIV_random_decamer oligonucleotide
CCA AAG TG*C* T SEQ ID NO: 78 Hg19_specific_antiHIV_random_decamer oligonucleotide
CTG GAG TG*C* A SEQ ID NO: 79 Hg19_specific_antiHIV_random_decamer oligonucleotide
TGC TGG GA*T* T SEQ ID NO: 80 Hg19_specific_antiHIV_random_decamer oligonucleotide
GGC TGG AG*T* G SEQ ID NO: 81 Hg19_specific_antiHIV_random_decamer oligonucleotide
CTG CCT CA*G* C SEQ ID NO: 82 Hg19_specific_antiHIV_random_decamer oligonucleotide
GCT GGA GT*G* C SEQ ID NO: 83 Hg19_specific_antiHIV_random_decamer oligonucleotide
AAA GTG CT*G* G SEQ ID NO: 84 Hg19_specific_antiHIV_random_decamer oligonucleotide
CCT GCC TC*A* G SEQ ID NO: 85 Hg19_specific_antiHIV_random_decamer oligonucleotide
GTG CTG GG*A* T SEQ ID NO: 86 Hg19_specific_antiHIV_random_decamer oligonucleotide
AGT GCT GG*G* A SEQ ID NO: 87 Hg19_specific_antiHIV_random_decamer oligonucleotide
AAG TGC TG*G* G SEQ ID NO: 88 Hg19_specific_antiHIV_random_decamer oligonucleotide
CTC ACT GC*A* A SEQ ID NO: 89 Hg19_specific_antiHIV_random_decamer oligonucleotide
TCC TGC CT*C* A SEQ ID NO: 90 Hg19_specific_antiHIV_random_decamer oligonucleotide
TGG AGT GC*A* G SEQ ID NO: 91 Hg19_specific_antiHIV_random_decamer oligonucleotide
TCT CCT GC*C* T SEQ ID NO: 92 Hg19_specific_antiHIV_random_decamer oligonucleotide
TTT TTT GA*G* A E. Sequences SEQ ID NO: 93 Hg19_specific_antiHIV_random_decamer oligonucleotide
TTC TCC TG*C* C SEQ ID NO: 94 Hg19_specific_antiHIV_random_decamer oligonucleotide
ATT CTC CT*G* C SEQ ID NO: 95 Hg19_specific_antiHIV_random_decamer oligonucleotide
GGC CTC CC*A* A SEQ ID NO: 96 Hg19_specific_antiHIV_random_decamer oligonucleotide
TTT TTT TG*A* G SEQ ID NO: 97 Hg19_specific_antiHIV_random_decamer oligonucleotide
TTT TTT TT*G* A SEQ ID NO: 98 Hg19_specific_antiHIV_random_decamer oligonucleotide
CAG CCT CC*C* A SEQ ID NO: 99 Hg19_specific_antiHIV_random_decamer oligonucleotide
AGC CTC CC*A* A SEQ ID NO: 100 Hg19_specific_antiHIV_random_decamer oligonucleotide
GAG TAG CT*G* G SEQ ID NO: 101 Hg19_specific_antiHIV_random_decamer oligonucleotide
TCA CTG CA*A* C SEQ ID NO: 102 Hg19_specific_antiHIV_random_decamer oligonucleotide
GGA TTA CA*G* G SEQ ID NO: 103 Hg19_specific_antiHIV_random_decamer oligonucleotide
GGC TCA CT*G* C SEQ ID NO: 104 Hg19_specific_antiHIV_random_decamer oligonucleotide
ACT GCA AC*C* T SEQ ID NO: 105 Hg19_specific_antiHIV_random_decamer oligonucleotide
CTG CAA CC*T* C SEQ ID NO: 106 Hg19_specific_antiHIV_random_decamer oligonucleotide
CAC TGC AA*C* C SEQ ID NO: 107 Hg19_specific_antiHIV_random_decamer oligonucleotide
TAA TTT TT*G* T SEQ ID NO: 108 Hg19_specific_antiHIV_random_decamer oligonucleotide
GGG ATT AC*A* G SEQ ID NO: 109 Hg19_specific_antiHIV_random_decamer oligonucleotide
GGG TTT CA*C* C SEQ ID NO: 110 5' LTR from near-full length HIV proviral amplicon integration site
amplicon
CTCTCTGGGTAACCACATGCTTAAGAACAATCTATACTTTAAGAATCTGACTTACTG
GAAGGGCTAGTTTGGTCCCAGAAAAGACAAGACATCCTTGATTTGTGGGTCTACCA
CAC SEQ ID NO: 111 integration site SEQ ID NO: 110 amplicon
ACTGGAAGGGCTAGTTTGGTCCCAGAAAAGACAAGACATCCTTGATTTGTGGGTCT
ACCACAC SEQ ID NO: 112 LTR sequence generated from the larger proviral amplicon
GCATTTCATATCCCTTCCATGACAAGTATTCAGGGGGAGCCCAACAAGATTACCTT
ACTGGAAGGGCTAGTTTGGTCCCAGAAAAGACAAGACATCCTTGATTTGTGGGTCT
ACCACACA SEQ ID NO: 113 protruding host sequence and 5' LTR
TGGAAGGGCTAGTTTGGTCCCAGAAAAGACAAGACATCCTTGATTTGTGGGTCTAC
CACACA SEQ ID NO: 114 CA_NPL12 is large proviral sequence
GCCCTTAAGACCAATGACTTACAAGGGAGCTTTAGATCTTAGCCACTTTTTAAAGA
AAGGGGGGACTGGAAGGGCTAGTTTGGTCCCAGAAAAGACAAGACATCCTTGATT
TGTGGG

| E. Sequences |
|---|
| SEQ ID NO: 115 integration site SEQ D NO: 114 amplicon<br>TGGAAGGGCTAGTTTGGTCCCAGAAAAGACAAGACATCCTTGATTTGTGGG |

What is claimed is:

1. A synthetic 71 base pair, partially-double stranded DNA oligonucleotide comprising a 3'dT overhang as set forth in SEQ ID NO: 1 and/or SEQ ID NO: 39, and 14 base pair antisense strand with a 5'P and two terminal 3' C3 spacers on the antisense strand as set forth in SEQ ID NO: 2 and/or SEQ ID NO: 40.

2. A kit for detecting the presence of viral nucleic acid in an integrated site in the genome of a host comprising the synthetic oligonucleotide of claim 1.

3. A method of detecting the presence and location of a viral nucleic acid integrated into the genome of a host comprising
   a) performing a first amplification reaction and a second amplification reaction on host genomic DNA; wherein the first amplification comprises ligating an adaptor molecule to a genomic DNA fragment from the host and performing a nested PCR reaction on the adaptor molecule ligated DNA fragment; wherein the adapter molecule comprises the synthetic 71 base pair, partially-double stranded DNA oligonucleotide comprising a 3'dT overhang as set forth in SEQ ID NO: 1 and/or SEQ ID NO: 39, and comprises the 14 base pair antisense strand with a 5'P and two terminal 3' C3 spacers on the antisense strand as set forth in SEQ ID NO: 2 and/or SEQ ID NO: 40 of claim 1; wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification;
   b) sequencing and aligning the amplicons generated by the first and second amplification reactions.

4. The method of claim 3, wherein the genomic DNA fragment from the host for the first amplification are created by subjecting the genomic DNA to focused acoustic shearing prior to ligation of the adaptor molecule.

5. The method of detecting the presence and location of a viral nucleic acid integrated into the genome of a host of claim 3, further comprising
   a) performing whole genome amplification (WGA) on a genomic DNA fragment from the host generating WGA amplicons;
   b) performing a nested near full length proviral amplification on the amplicons generated by the WGA reaction;
   c) constructing a library of amplicons from WGA DNA generated in step a that were identified to contain proviruses during step b;
   d) performing a viral specific nested PCR on library; and
   e) sequencing the amplicons of step b and step d.

6. The method of claim 3, wherein the viral specific nested PCR of step d can comprise ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang as set forth in SEQ ID NO: 1, and 14 base pair antisense strand with a 5'P and two terminal 3' C3 spacers on the antisense strand as set forth in SEQ ID NO: 2 and/or SEQ ID NO: 40; wherein at least one forward primer of the nested PCR reaction of the first amplification is specific for the adaptor molecule; wherein at least one reverse primer of the nested PCR reaction of the first amplification is a viral specific primer.

7. The method of claim 5, further comprising screening the WGA reaction amplicons before constructing a library of amplicons.

8. The method of claim 3, wherein the viral nucleic acid is from a virus from the viral family Retroviridae, Herpesviridae, or Hepadnaviridae.

9. The method of claim 8, wherein the virus is a lentivirus or a deltaretrovirus.

10. The method of claim 9, wherein the virus the lentivirus comprises Human Immunodeficiency virus.

11. The method of claim 8, wherein the virus is a Hepatitis B virus.

12. The method of claim 8, wherein the virus is a from the Herpesviridae viral family and is selected from the group consisting of Herpes Simplex Virus-1, Herpes Simplex Virus-2, Varicella-zoster virus, Epstein-Barr virus, Cytomegalovirus, Human Herpes Virus 6A, Human Herpes Virus 6B, Human Herpes Virus 7, and Human Herpes Virus 8.

13. A method of diagnosing a subject with a latent viral infection, the method comprising
   a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises the synthetic 71 base pair, partially-double stranded DNA oligonucleotide of claim 1; wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification;
   b) sequencing and aligning the amplicons generated by the first and second amplification reactions; and
   c) assembling integrated proviral sequence to a known full viral sequence; wherein the identification of a viral or proviral sequence absent any truncations, mutations, deletions, or additions in the viral genome indicates a latent viral infection.

14. A method of treating a latent viral infection in a subject comprising detecting the presence of a viral or proviral nucleic acid integrated in the host genome said method comprising
   a) performing a first amplification reaction and a second amplification reaction on host genomic DNA; wherein the first amplification comprises ligating an adaptor molecule to a genomic DNA fragment from the host and performing a nested PCR reaction on the adaptor molecule ligated DNA fragment; wherein the adapter molecule comprises the synthetic 71 base pair, partially-double stranded DNA oligonucleotide comprising a 3'dT overhang (such as for example, partially-double stranded DNA oligonucleotide of claim 1; wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification;
   b) sequencing and aligning the amplicons generated by the first and second amplification reactions;
   c) aligning any aligned integrated proviral sequence to a known full viral sequence; wherein the identification of a viral or proviral sequence absent any truncations, mutations, deletions, or additions in the viral genome indicates a latent viral infection; and
   d) treating the subject with a suitable antiviral for the detected infection.

15. A method of assaying the efficacy of an antiviral treatment, the method comprising a) performing a first amplification reaction and a second amplification reaction; wherein the first amplification comprises ligating an adaptor molecule to a genomic DNA fragment from the host and performing a nested PCR reaction on the adaptor molecule ligated DNA fragment; wherein the adapter molecule comprises a synthetic 71 base pair, partially-double stranded DNA oligonucleotide comprising a 3'dT overhang as set forth in SEQ ID NO: 1, and 14 base pair antisense strand with a 5'P and two terminal 3' C3 spacers on the antisense strand as set forth in SEQ ID NO: 2 and/or SEQ ID NO: 40; wherein at least one forward primer of the nested PCR reaction of the first amplification is specific for the adaptor molecule; wherein at least one reverse primer of the nested PCR reaction of the first amplification is a viral specific primer; wherein the second amplification reaction comprises a nested near full length proviral amplification; b) sequencing and aligning the amplicons generated by the first and second amplification reactions; and c) assembling integrated proviral sequence to a known full viral sequence; wherein a reduction in the amount of functional integrated virus or provirus relative to a control or absence of integrated virus or provirus indicates that the anti-viral was efficacious.

* * * * *